(12) United States Patent
Hirao et al.

(10) Patent No.: US 8,895,712 B2
(45) Date of Patent: Nov. 25, 2014

(54) ARTIFICIAL BASE PAIR CAPABLE OF FORMING SPECIFIC BASE PAIR

(75) Inventors: Ichiro Hirao, Komae (JP); Michiko Hirao, Yokohama (JP); Shigeyuki Yokoyama, Yokohama (JP)

(73) Assignees: Riken, Wako-shi (JP); Tagcyx Biotechnologies, Yokohama-shi (JP)

( * ) Notice: Subject to any disclaimer, the term of this patent is extended or adjusted under 35 U.S.C. 154(b) by 109 days.

(21) Appl. No.: 13/500,635

(22) PCT Filed: Oct. 6, 2010

(86) PCT No.: PCT/JP2010/067560
§ 371 (c)(1),
(2), (4) Date: Apr. 5, 2012

(87) PCT Pub. No.: WO2011/043385
PCT Pub. Date: Apr. 14, 2011

(65) Prior Publication Data
US 2012/0231462 A1 Sep. 13, 2012

(30) Foreign Application Priority Data
Oct. 6, 2009 (JP) ................................. 2009-232851

(51) Int. Cl.
*C07H 21/02* (2006.01)
*C07H 21/04* (2006.01)
(52) U.S. Cl.
USPC .................. 536/23.1; 536/24.3; 435/6.11
(58) Field of Classification Search
USPC .................. 536/23.1, 24.3; 435/6.11
See application file for complete search history.

(56) References Cited

U.S. PATENT DOCUMENTS

| 5,432,272 A | 7/1995 | Benner |
| 6,140,496 A | 10/2000 | Benner |
| 6,617,106 B1 | 9/2003 | Benner |

(Continued)

FOREIGN PATENT DOCUMENTS

| EP | 1114827 A1 | 7/2001 |
| EP | 1970445 A1 | 9/2008 |

(Continued)

OTHER PUBLICATIONS

Benner, S.A., "Understanding Nucleic Acids Using Synthetic Chemistry," Acc. Chem. Res., vol. 37, No. 10, pp. 784-797, (2004).

(Continued)

*Primary Examiner* — Jezia Riley
(74) *Attorney, Agent, or Firm* — Birch, Stewart, Kolasch & Birch, LLP

(57) ABSTRACT

The present invention provides a double-stranded nucleic acid in which at least one nucleic acid strand includes an unnatural base that forms a self-complementary base pair or an unnatural base that forms a base pair with any natural base with substantially the same thermal stability. The present invention also provides a method of hybridizing a first nucleic acid strand with a second nucleic acid strand, wherein the first nucleic acid strand includes an unnatural base that forms a self-complementary base pair or an unnatural base that forms a base pair with any natural base with substantially the same thermal stability, and a method of applying the nucleic acid to SNP detection, a DNA chip, DNA/RNA computing, or an in vitro translation system. The present invention provides a method of introducing an unnatural base into a nucleic acid strand and thereby controlling the thermodynamic stability in hybridization of the nucleic acid strand.

16 Claims, 12 Drawing Sheets

(56) References Cited

U.S. PATENT DOCUMENTS

| | | |
|---|---|---|
| 6,977,161 B2 | 12/2005 | Grenier et al. |
| 2009/0286247 A1 | 11/2009 | Hirao et al. |
| 2010/0036111 A1 | 2/2010 | Hirao et al. |
| 2011/0087015 A1 | 4/2011 | Hirano et al. |

FOREIGN PATENT DOCUMENTS

| | | |
|---|---|---|
| WO | WO 01/05801 A1 | 1/2001 |
| WO | WO-2005/026187 A1 | 3/2005 |
| WO | WO-200766737 A1 | 6/2007 |

OTHER PUBLICATIONS

Sheng, P., et al., "Design of a novel molecular beacon: modification of the stem with artificially genetic alphabet," Chem. Commun., vol. 41, pp. 5128-5130, (2008).

Nolte, F.S., et al., "MultiCode-PLx System for Multiplexed Detection of Seventeen Respiratory Viruses," J. Clin. Microbiol., vol. 45, No. 9, pp. 2779-2786, (Sep. 2007).

Svarovskaia, E.S., et al., "MultiCode-RTx Real-Time PCR System for Detection of Subpopulations of K65R Human Immunodeficiency Virus Type 1 Reverse Transcriptase Mutant Viruses in Clinical Samples," J. Clin. Microbiol., vol. 44, No. 11, pp. 4237-4241, (Nov. 2006).

Prudent, J.R., "Using expanded genetic alphabets to simplify high-throughput genetic testing," Expert Rev. Mo. Diagn., vol. 6, No. 2, pp. 245-252, (2006).

Johnson, S.C., et al., "Multiplexed Genetic Analysis Using an Expanded Genetic Alphabet," Clinical Chemistry, vol. 50, No. 11, 2019-2027, (2004).

Berger, M., et al., "Universal bases for hybridization, replication and chain termination," Nucleic Acids Research, vol. 28, No. 15, pp. 2911-2914, (2000).

McMinn, D.L., et al., "Efforts toward Expansion of the Genetic Alphabet: DNA Polymerase Recognition of a Highly Stable, Self-Pairing Hydrophobic Base," J. Am. Chem. Soc., vol. 121, pp. 11585-11586, (1999).

Kimoto, M., et al., "An unnatural base pair system for efficient PCR amplification and functionalization of DNA molecules," Nucleic Acids Research, vol. 37, No. 2, pp. 1-9, (2009).

Hirao, I., et al., "An unnatural hydrophobic base pair system: site-specific incorporation of nucleotide analogs into DNA and RNA," Nature Methods, vol. 3, No. 9, pp. 729-735, (Sep. 2006).

Hirao, I., et al., "An Efficient Unnatural Base Pair for PCR Amplification," J. Am. Chem. Soc., vol. 129, No. 50, pp. 15549-15555, (2007).

Mitsui, T., et al., "An Efficient Unnatural Base Pair for a Base-Pair-Expanded Transcription System," J. Am. Chem. Soc., vol. 127, No. 24, pp. 8652-8658, (2005).

Fujiwara, T., et al., "Synthesis of 6-(2-Thienyl)purine Nucleoside Derivatives That Form Unnatural Base Pairs with Pyridin-2-one Nucleosides," Bioorg. Med. Chem. Lett., vol. 11, No. 16, pp. 2221-2223, (2001).

Hirao, I., et al., "A Two-Unnatural-Base-Pair System toward the Expansion of the Genetic Code," J. Am. Chem. Soc., vol. 126, No. 41, pp. 13298-13305, (2004).

Mitsui, T., et al., "Characterization of fluorescent, unnatural base pairs," Tetrahedron, vol. 63, pp. 3528-3537, (2007).

Extended European Search Report issued in corresponding European Patent Application 10822055.9 dated Jul. 26, 2013.

Hirao et al., "Unnatural base pairs between 2- and 6-substituted purines and 2-oxo(1H)pyridine for expansion of the genetic alphabet," Bioorganic and Medicinal Chemistry Letters, 2004, vol. 14, pp. 4887-4890.

Kimoto et al., "A Unique Fluorescent Analogue for the Expansion of the Genetic Alphabet," Journal of the American Chemical Society, 2010, vol. 132, pp. 4988-4989.

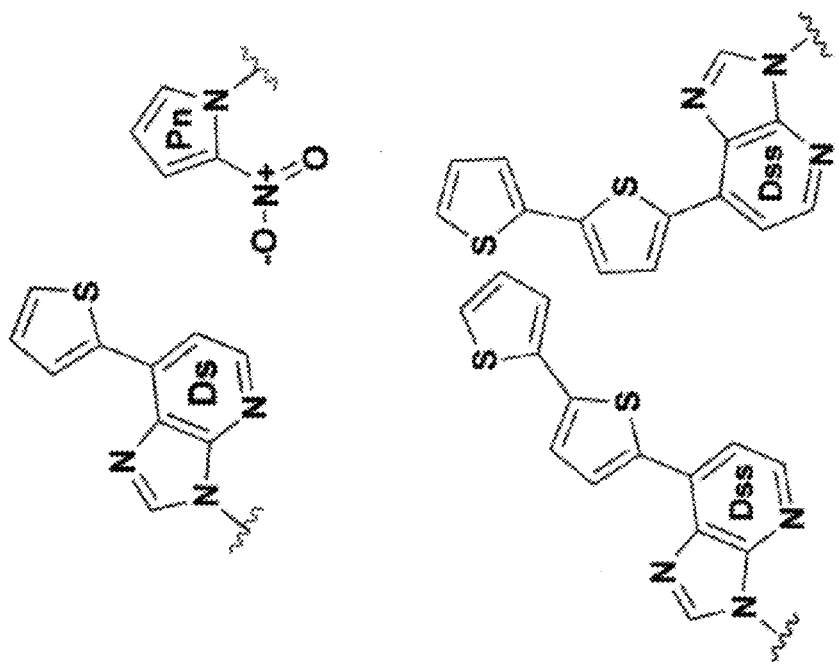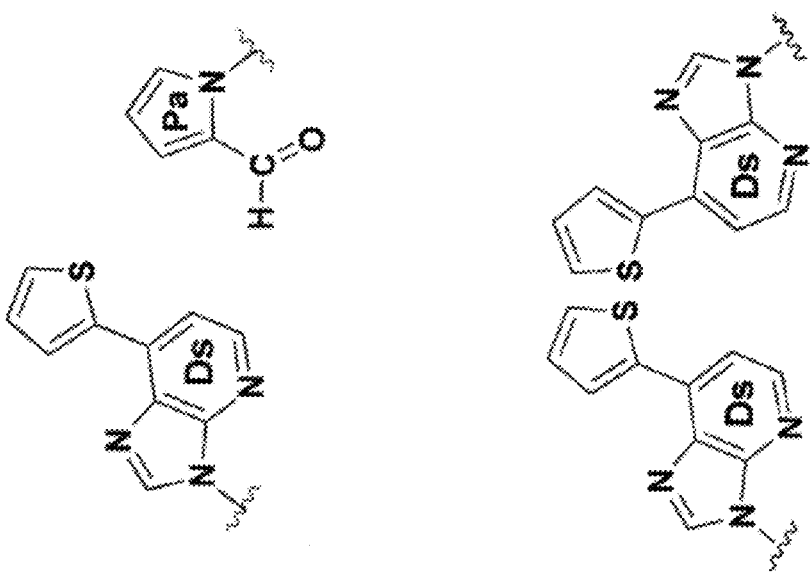
Fig. 1

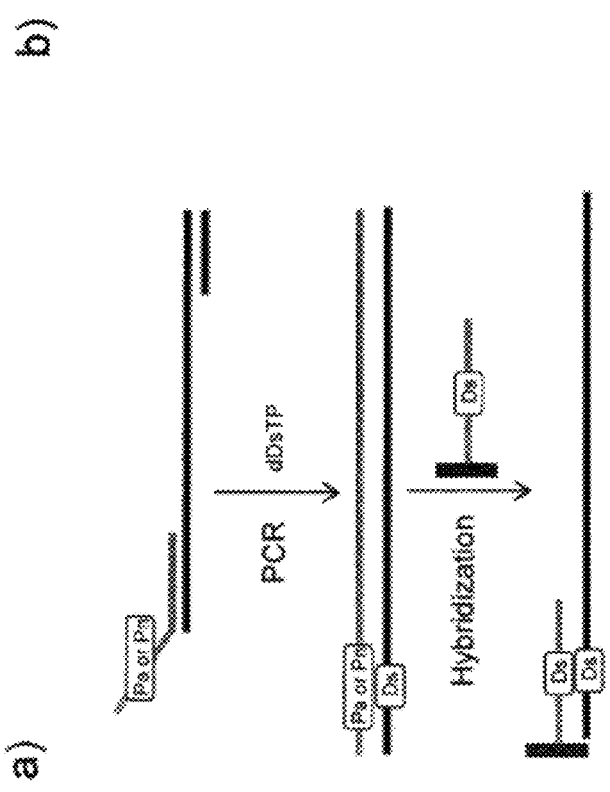
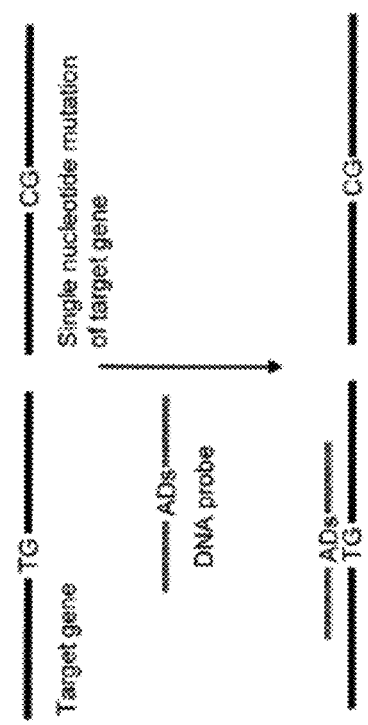
Fig. 2

Fig. 3

| X-Y | 5'-CGCAT-X-GTTACC-3'<br>3'-GCGTA-Y-CAATGG-5'<br>Tm (°C) |
|---|---|
| Dss-Dss | 53.9 |
| A-Dss | 45.3 |
| T-Dss | 43.9 |
| G-Dss | 45.9 |
| C-Dss | 44.9 |

| X-Y | 5'-CGCAT-X-GTTACC-3'<br>3'-GCGTA-Y-CAATGG-5'<br>Tm (°C) |
|---|---|
| Dss-Ds | 52.0 |
| A-Ds | 43.5 |
| T-Ds | 40.5 |
| G-Ds | 44.2 |
| C-Ds | 40.7 |
| Pa-Ds | 42.4 |
| Pn-Ds | 43.9 |
| C-G | 53.1 |
| T-A | 48.6 |
| T-G | 42.4 |
| A-G | 38.6 |
| C-A | 33.6 |

Fig. 4

5'-CGCA-N₁DsN₂-TTACC-3'
3'-GCGT-N₃DsN₄-AATGG-5'

| N₁ | | N₂ | | | |
|---|---|---|---|---|---|
| | | G | A | C | T |
| C | | 57.2 | 53.4 | - | - |
| T | | 51.6 | 48.1 | - | - |
| G | | 49.2 | 44.6 | 44.1 | - |
| A | | 46.5 | 42.5 | 41.7 | 37.7 |

5'-CGCA-N₁G N₂-TTACC-3'
3'-GCGT-N₃DsN₄-AATGG-5'

| N₁ | | N₂ | | | |
|---|---|---|---|---|---|
| | | G | A | C | T |
| C | | 49.9 | 45.3 | - | - |
| T | | 45.0 | 40.1 | - | - |
| G | | 41.1 | 36.4 | 36.8 | - |
| A | | 39.4 | 34.7 | 34.8 | 30.0 |

Tm2: 5'-CGCA-nnn-TTACC-3'
Tm3: 3'-GCGT-mmm-AATGG-5'

| No | Seq (nnn) | Tm | ΔTm |
|----|-----------|------|------|
| 1  | TCG       | 53.1 | -    |
| 2  | CDsG      | 57.2 | 4.1  |
| 3  | CDsA      | 53.4 | 0.3  |
| 4  | TDsG      | 51.8 | -1.3 |
| 5  | GDsG      | 49.2 | -3.9 |
| 6  | TDsA      | 48.1 | -5.0 |
| 7  | ADsC      | 46.5 | -6.6 |
| 8  | GDsA      | 44.6 | -8.5 |
| 9  | GDsC      | 44.1 | -9.0 |
| 10 | ADsA      | 42.5 | -10.6 |
| 11 | ADsC      | 41.7 | -11.4 |
| 12 | ADsT      | 37.7 | -15.4 |

Fig. 8

| Nearest-neighbor sequence (5'-3'/5'-3') | ΔG kcal/mol | Reference |
|---|---|---|
| AA/TT | -1 | PNAS, 1998 |
| AG/CT | -1.28 | PNAS, 1998 |
| AT/AT | -0.88 | PNAS, 1998 |
| AC/GT | -1.44 | PNAS, 1998 |
| GA/TC | -1.30 | PNAS, 1998 |
| GG/CC | -1.84 | PNAS, 1998 |
| GC/GC | -2.24 | PNAS, 1998 |
| TA/TA | -0.58 | PNAS, 1998 |
| TG/CA | -1.45 | PNAS, 1998 |
| CG/CG | -2.17 | PNAS, 1998 |
| ADs/DsT | -0.59 | (this work) |
| TDs/DsA | -1.85 | (this work) |
| CDs/DsG | -2.42 | (this work) |
| GDs/DsC | -1.03 | (this work) |

Calculation of ΔG (37°C, 0.1 M NaCl) by hyperchromicity calculation method → Correction to unified ΔG (37°C, 1 M NaCl) → Calculation of NN ΔG (37°C, 1 M NaCl)

Fig. 10

5'-CGCATDsGTTACC-3'
3'-GCGTADsCAATGG-5'   Tm = 51.5 °C

5'-CGCATDsDsGTACC-3'
3'-GCGTADsCDsAATGG-5'   Tm = 39.7 °C

5'-CGCATDsGDsTACC-3'
3'-GCGTADsCDsAATGG-5'   Tm = 45.2 °C

5'-CGCATDs G TTACC-3'
3'-GCGTADsDsAATGG-5'   Tm = 31.6 °C

5'-CGCATDsG T TACC-3'
3'-GCGTADsCDsAATGG-5'   Tm = 38.1 °C

5'-CGACDsGDsAACC-3'
3'-GCTGDsCGDsTTGG-5'   Tm = 61.8 °C

5'-CGAC G GC G AACC-3'
3'-GCTGDsCGDsTTGG-5'   Tm = 43.5 °C

5'-CGACGGCGAACC-3'
3'-GCTGCCGCTTGG-5'   Tm = 61.0 °C

5'-CGCATCGTTACC-3'
3'-GCGTAGCAATGG-5'   Tm = 53.1 °C

Fig. 11

5'-CGCAT GGTTACC-3'
3'-GCGTA̲DsCAATGG-5'    Tm = 45.5 °C

5'-CGCAA GGTTACC-3'
3'-GCGTA̲DsCAATGG-5'    Tm = 26.9 °C    ΔTm = 18.7 °C

5'-CGCAG GGTTACC-3'
3'-GCGTA̲DsCAATGG-5'    Tm = 29.3 °C    ΔTm = 16.2 °C

5'-CGCAC GGTTACC-3'
3'-GCGTA̲DsCAATGG-5'    Tm = 31.6 °C    ΔTm = 13.9 °C

5'-CGCAT GGTTACC-3'
3'-GCGTA CCAATGG-5'    Tm = 52.3 °C

5'-CGCAA GGTTACC-3'
3'-GCGTA CCAATGG-5'    Tm = 37.4 °C    ΔTm = 15.0 °C

5'-CGCAG GGTTACC-3'
3'-GCGTA CCAATGG-5'    Tm = 42.7 °C    ΔTm = 9.6 °C

5'-CGCAC GGTTACC-3'
3'-GCGTA CCAATGG-5'    Tm = 39.8 °C    ΔTm = 12.6 °C

Fig. 12

| | Ds–Ds base pair | G–Ds base pair |
|---|---|---|
| 5'--CGCAGCGGTTGCC--3'<br>3'--GCGTCGCAACGG--5'<br>Tm=62.0°C (9) | 5'--CGCADsCGTTGCC--3'<br>3'--GCGTDsGCAACGG--5'<br>Tm=52.4°C (8) | 5'--CGCA G CGTTGCC--3'<br>3'--GCGTDsGCAACGG--5'<br>Tm=43.5°C (8) |
| 5'--CGCATCGTTGCC--3'<br>3'--GCGTAGCAACGG--5'<br>Tm=60.0°C (8) | 5'--CGCATCDsTTGCC--3'<br>3'--GCGTAGDsAACGG--5'<br>Tm=53.4°C (7) | 5'--CGCATC G TTGCC--3'<br>3'--GCGTAGDsAACGG--5'<br>Tm=46.6°C (7) |
| 5'--CGCACGATTACC--3'<br>3'--GCGTGCTAATGG--5'<br>Tm=55.9°C (7) | 5'--CGCACDsATTACC--3'<br>3'--GCGTGDsTAATGG--5'<br>Tm=53.5°C (6) | 5'--CGCAC G ATTACC--3'<br>3'--GCGTGDsTAATGG--5'<br>Tm=45.3°C (6) |
| 5'--CGCATGGTTACC--3'<br>3'--GCGTACCAATGG--5'<br>Tm=52.7°C (7) | 5'--CGCATDsGTTACC--3'<br>3'--GCGTADsCAATGG--5'<br>Tm=51.6°C (6) | 5'--CGCAT G GTTACC--3'<br>3'--GCGTADsCAATGG--5'<br>Tm=45.0°C (6) |
| 5'--CGTACGGTTACC--3'<br>3'--GCATGCCAATGG--5'<br>Tm=50.1°C (7) | 5'--CGTACDsGTTACC--3'<br>3'--GCATGDsCAATGG--5'<br>Tm=50.7°C (6) | 5'--CGTAC G GTTACC--3'<br>3'--GCATGDsCAATGG--5'<br>Tm=42.7°C (6) |

SEQUENCE LISTING

```
<160> NUMBER OF SEQ ID NOS: 50

<210> SEQ ID NO 1
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for any natural bases or an unnatural
      base Ds, Pa or Pn

<400> SEQUENCE: 1
cgcatngtta cc                                                          12

<210> SEQ ID NO 2
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for any natural base or an unnatural
      base Ds, Dss

<400> SEQUENCE: 2
ggtaacnatg cg                                                          12

<210> SEQ ID NO 3
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n at position 5 may be any natural base
<220> FEATURE:
<221> NAME/KEY: misc_feature
```

```
<222> LOCATION: (6)..(6)
<223> OTHER INFORMATION: n at position 6 stands for an unnatural base Ds
<220> FEATURE:
<221> NAME/KEY: misc_feature
<222> LOCATION: (7)..(7)
<223> OTHER INFORMATION: n at position 7 stands for any natural base

<400> SEQUENCE: 3
cgcannntta cc                                                     12

<210> SEQ ID NO 4
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n at position 6 stands for any natural base
<220> FEATURE:
<221> NAME/KEY: misc_feature
<222> LOCATION: (7)..(7)
<223> OTHER INFORMATION: n at position 7 stands for an unnatural base Ds
<220> FEATURE:
<221> NAME/KEY: misc_feature
<222> LOCATION: (8)..(8)
<223> OTHER INFORMATION: n at position 8 stands for any natural base

<400> SEQUENCE: 4
ggtaannntg cg                                                     12

<210> SEQ ID NO 5
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n stands for any natural base
<220> FEATURE:
<221> NAME/KEY: misc_feature
<222> LOCATION: (7)..(7)
<223> OTHER INFORMATION: n stands for any natural base

<400> SEQUENCE: 5
cgcangntta cc                                                     12

<210> SEQ ID NO 6
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 6
cgacggcgaa cc                                                     12

<210> SEQ ID NO 7
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 7
ggttcgccgt cg                                                     12
```

<210> SEQ ID NO 8
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds

<400> SEQUENCE: 8
cgacgncgaa cc                                                          12

<210> SEQ ID NO 9
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for an unnatural base Ds

<400> SEQUENCE: 9
ggttcgncgt cg                                                          12

<210> SEQ ID NO 10
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 10
cgcatcgttg cc                                                          12

<210> SEQ ID NO 11
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 11
ggcaacgatg cg                                                          12

<210> SEQ ID NO 12
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 12
cgcatcgttg cc                                                          12

<210> SEQ ID NO 13
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 13
ggcaacggtg cg                                                          12

```
<210> SEQ ID NO 14
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n stands for an unnatural base Ds

<400> SEQUENCE: 14
cgcancgttg cc                                                          12

<210> SEQ ID NO 15
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (8)..(8)
<223> OTHER INFORMATION: n stands for an unnatural base Ds

<400> SEQUENCE: 15
ggcaacgntg cg                                                          12

<210> SEQ ID NO 16
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for an unnatural base Ds

<400> SEQUENCE: 16
cgcatcnttg cc                                                          12

<210> SEQ ID NO 17
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds

<400> SEQUENCE: 17
ggcaangatg cg                                                          12

<210> SEQ ID NO 18
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 18
cgcatcgtta cc                                                          12

<210> SEQ ID NO 19
```

```
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 19
ggtaacgatg cg                                                          12

<210> SEQ ID NO 20
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds

<400> SEQUENCE: 20
cgcatngtta cc                                                          12

<210> SEQ ID NO 21
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for an unnatural base Ds

<400> SEQUENCE: 21
ggtaacnatg cg                                                          12

<210> SEQ ID NO 22
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 22
cgtatcgtta cc                                                          12

<210> SEQ ID NO 23
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 23
ggtaacgata cg                                                          12

<210> SEQ ID NO 24
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 24
cgtactgtta cc                                                          12
```

```
<210> SEQ ID NO 25
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 25
ggtaacagta cg                                                             12

<210> SEQ ID NO 26
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds

<400> SEQUENCE: 26
cgtacngtta cc                                                             12

<210> SEQ ID NO 27
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for an unnatural base Ds

<400> SEQUENCE: 27
ggtaacngta cg                                                             12

<210> SEQ ID NO 28
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(7)
<223> OTHER INFORMATION: n stands for an unnatural base Ds

<400> SEQUENCE: 28
cgcatnngta cc                                                             12

<210> SEQ ID NO 29
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(7)
<223> OTHER INFORMATION: n stands for an unnatural base Ds

<400> SEQUENCE: 29
ggtaannatg cg                                                             12

<210> SEQ ID NO 30
<211> LENGTH: 12
<212> TYPE: DNA
```

```
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds
<220> FEATURE:
<221> NAME/KEY: misc_feature
<222> LOCATION: (8)..(8)
<223> OTHER INFORMATION: n stands for an unnatural base Ds

<400> SEQUENCE: 30
cgcatngnta cc                                                          12

<210> SEQ ID NO 31
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n stands for an unnatural base Ds
<220> FEATURE:
<221> NAME/KEY: misc_feature
<222> LOCATION: (7)..(7)
<223> OTHER INFORMATION: n stands for an unnatural base Ds

<400> SEQUENCE: 31
ggtancnatg cg                                                          12

<210> SEQ ID NO 32
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n stands for n unnatural base Ds
<220> FEATURE:
<221> NAME/KEY: misc_feature
<222> LOCATION: (8)..(8)
<223> OTHER INFORMATION: n stands for n unnatural base Ds

<400> SEQUENCE: 32
cgacngcnaa cc                                                          12

<210> SEQ ID NO 33
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (5)..(5)
<223> OTHER INFORMATION: n stands for an unnatural base Ds
<220> FEATURE:
<221> NAME/KEY: misc_feature
<222> LOCATION: (8)..(8)
<223> OTHER INFORMATION: n stands for an unnatural base Ds

<400> SEQUENCE: 33
ggttngcngt cg                                                          12

<210> SEQ ID NO 34
<211> LENGTH: 12
```

```
<212> TYPE: DNA
<213> ORGANISM: Artificial sequence
<220> FEATURE:
<223> OTHER INFORMATION: DNA fragment for testing thermostability

<400> SEQUENCE: 34
cgacggcgaa cc                                                              12

<210> SEQ ID NO 35
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 35
ggttcgccgt cg                                                              12

<210> SEQ ID NO 36
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 36
cgcatcgtta cc                                                              12

<210> SEQ ID NO 37
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 37
ggtaacgatg cg                                                              12

<210> SEQ ID NO 38
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 38
cgcatggtta cc                                                              12

<210> SEQ ID NO 39
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 39
cgcaaggtta cc                                                              12

<210> SEQ ID NO 40
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 40
```

-continued

```
cgcagggtta cc                                                       12

<210> SEQ ID NO 41
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 41
cgcacggtta cc                                                       12

<210> SEQ ID NO 42
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 42
ggtaaccatg cg                                                       12

<210> SEQ ID NO 43
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 43
cgcagcgttg cc                                                       12

<210> SEQ ID NO 44
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 44
ggcaacgctg cg                                                       12

<210> SEQ ID NO 45
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 45
cgcacgatta cc                                                       12

<210> SEQ ID NO 46
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 46
ggtaatcgtg cg                                                       12

<210> SEQ ID NO 47
<211> LENGTH: 12
<212> TYPE: DNA
<213> ORGANISM: Artificial sequence
```

```
<220> FEATURE:
<223> OTHER INFORMATION: DNA fragment for testing thermostability
<220> FEATURE:
<221> NAME/KEY: misc_feature
<222> LOCATION: (6)..(6)
<223> OTHER INFORMATION: n stands for an unnatural base Ds

<400> SEQUENCE: 47
cgcagnatta cc                                                             12

<210> SEQ ID NO 48
<211> LENGTH: 12
<212> TYPE: DNA
<213> ORGANISM: Artificial sequence
<220> FEATURE:
<223> OTHER INFORMATION: DNA fragment for testing thermostability
<220> FEATURE:
<221> NAME/KEY: misc_feature
<222> LOCATION: (7)..(7)
<223> OTHER INFORMATION: n stands for an unnatural base Ds

<400> SEQUENCE: 48
ggtaatngtg cg                                                             12

<210> SEQ ID NO 49
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 49
cgtacggtta cc                                                             12

<210> SEQ ID NO 50
<211> LENGTH: 12
<212> TYPE: DNA
<213> ORGANISM: Artificial sequence
<220> FEATURE:
<223> OTHER INFORMATION: DNA fragment for testing thermostability

<400> SEQUENCE: 50
ggtaaccgta cg                                                             12
```

ARTIFICIAL BASE PAIR CAPABLE OF FORMING SPECIFIC BASE PAIR

This application is the National Stage under 35 USC §371 of International Application Number PCT/JP2010/067560 filed on Oct. 6, 2010, which claims priority under 35 USC §119(a)-(d) of Application Number 2009-232851 filed on Oct. 6, 2009 in Japan.

TECHNICAL FIELD

The present invention relates to a double-stranded nucleic acid in which at least one nucleic acid strand includes an unnatural base that forms a self-complementary base pair or an unnatural base that forms a base pair with any natural base with substantially the same thermal stability. The present invention also relates to a method of hybridizing a first nucleic acid strand with a second nucleic acid strand, wherein the first nucleic acid strand includes an unnatural base that forms a self-complementary base pair or an unnatural base that forms a base pair with any natural base with substantially the same thermal stability. The present invention further relates to a method of applying a nucleic acid including an unnatural base that forms a self-complementary base pair or an unnatural base that forms with any natural base with substantially the same thermal stability to SNP detection, a DNA chip, DNA/RNA computing, or an in vitro translation system. Furthermore, the present invention relates to a method of introducing an unnatural base that forms a self-complementary base pair or an unnatural base that forms a base pair with any natural base with substantially the same thermal stability into a nucleic acid strand and thereby controlling the thermodynamic stability in hybridization of the nucleic acid strand.

BACKGROUND ART

DNAs form a double-stranded structure though base pairs A-T and G-C. The formation of a double strand by hybridization of DNAs due to complementarity of base pairs is applied to various fields such as a DNA tag for detecting DNA, a DNA probe for, for example, Southern hybridization, a DNA array, a zip-code of DNA, real-time PCR technologies such as TaqMan, a molecular beacon, a DNA affinity column for isolating DNA having a specific sequence, and also a DNA computer. The number of sequences composed of four types of bases, A, G, C, and T, is enormous, e.g., about $10^6$ ($=4^{10}$) even in the case of a DNA consisting of only 10 bases. However, even if a wrong base pair other than A-T or G-C (mismatched base pair such as G-T) is present at one position of the 10-base DNA, a double strand may be formed (mishybridization) under some conditions, which may lead to incorrect DNA detection. In particular, since a G-C base pair is thermally stable than an A-T base pair, the stability of double-stranded DNAs varies depending on a difference in content of the G-C base pairs even if the DNAs have the same length. A double-stranded DNA having a high G-C content, even if the DNA has one mismatched base pair, the stability thereof tends to be higher than that of a double-stranded DNA having a low G-C content. Hybridization in practical technologies is performed under the same temperatures and the same conditions. Accordingly, in order to use a plurality of DNA tags or probes, it is important that the respective double-stranded DNAs have the same thermal stability. Mishybridization in such a method using a plurality of DNA tags or probes can be reduced if the variation of base pairs is increased by using a novel unnatural base pair in addition to base pairs, A-T and G-C, and a constant thermal stability is achieved regardless of the G-C contents of different double-stranded DNAs having the same length by using the novel unnatural base pair. The accuracy in each practical technology can be thereby enhanced. Furthermore, the accuracy of a method such as SNP analysis can be enhanced if a probe that can selectively distinguish between match and mismatch with a target DNA at a single-base mutation level is produced.

The technology for expanding genetic information of DNA by unnaturally forming novel base pairs has two possible applications having high versatility, and unnatural base pairs have been actively being developed. One of the applications is formation of an unnatural base pair that functions in replication, transcription, or translation to produce DNA, RNA, or protein containing a novel constituent. The other application is formation of a double-stranded nucleic acid by incorporating an unnatural base pair into DNA or RNA to increase the number of nucleic acid fragment probe sequences, which can be applied to a multiplex by real-time PCR and a DNA computer and further can be used in a novel codon and anticodon in introduction of an unnatural amino acid into protein by translation.

S. A. Benner, et al. produced base pairs such as isoG-isoC by modifying the combination of hydrogen bond patterns in natural base pairs and found that these unnatural base pairs selectively form base pairs in a double-stranded DNA (Patent Documents 1 to 3 and Non-Patent Documents 1 and 2). J. R. Prudent, et al. have produced a novel DNA probe using an isoG-isoC base pair and have designed a multiplex PCR method (Patent Document 4 and Non-Patent Documents 3 to 6). However, these base pairs have hydrogen bonding substituents; hence, amidite reagents in which protecting groups are introduced to the substituents of the bases are necessary to be prepared for DNA synthesis. The present inventors have intensively developed the third, unnatural base pairs (unnatural base pairs) for expanding genetic information of DNA and have successfully developed several unnatural base pairs that function in replication or transcription, such as an s-y base pair (s: 2-amino-6-thienylpurine, y: pyridin-2-one), a v-y base pair (v: 2-amino-6-thiazolyl purine), an s-Pa base pair (Pa: pyrrole-2-carbaldehyde), a Ds-Pa base pair (Ds: 7-(2-thienyl)-imidazo[4,5-b]pyridine), and a Ds-Pn base pair (Pn: 2-nitropyrrole) (Patent Document 5 and Non-Patent Documents 9 and 10). However, since these unnatural bases are utilized as base pairs, amidite reagents of two types of bases are necessary to be prepared.

In order to overcome these disadvantages, if a base not having hydrogen binding substituents self-complementarily forms a base pair, a preparation of only one amidite reagent may be sufficient, which significantly facilitates the use of the bases. F. E. Romesberg, et al. have developed such a self-complementary base pair (Non-Patent Documents 7 and 8). Their self-complementary base pair (7-propynyl isocarbostyril) is more stable than the G-C base pair, and the stability of a base pair with a natural base is reduced by 7 to 11° C. Though this unnatural base is self-complementarily incorporated into DNA by replication, the replication stopped after formation of the self-complementary base pair.

Further, in unnatural base pairs that have been already developed, thermal stability of DNA in each combination of an unnatural base pair and a natural base pair adjacent to each other has not been comprehensively investigated.

CITATION LIST

Patent Document

Patent Document 1: U.S. Pat. No. 5,432,272
Patent Document 2: U.S. Pat. No. 6,140,496

Patent Document 3: U.S. Pat. No. 6,617,106
Patent Document 4: U.S. Pat. No. 6,977,161
Patent Document 5: International Publication No. WO07/66737

Non-Patent Document

Non-Patent Document 1: S. A. Benner, Acc. Chem. Res., 37, 784-797 (2004).
Non-Patent Document 2: P. Sheng, et al., Chem. Commun., 5128-5130 (2008).
Non-Patent Document 3: F. S. Nolte, et al., J. Clin. Microbiol., 45, 2779-2786 (2007).
Non-Patent Document 4: E. S. Svarovskaia, et al., J. Clin. Microbiol., 44, 4237-4241 (2006).
Non-Patent Document 5: J. R. Prudent, Expert. Rev. Mol. Diagn., 6, 245-252 (2006).
Non-Patent Document 6: S. C. Johnson, et al., Clin. Chem., 50, 2019-2027 (2004).
Non-Patent Document 7: M. Berger, et al., Nucleic Acids Res., 28, 2911-2914 (2000).
Non-Patent Document 8: D. L. McMinn, et al., J. Am. Chem. Soc., 121, 11585-11586 (1999).
Non-Patent Document 9: M. Kimoto, et al, Nucleic Acids Res., 37, e14 (2009).
Non-Patent Document 10: I. Hirao, et al., Nature Methods, 3, 729-735 (2006).

SUMMARY OF INVENTION

Technical Problem

It is an object of the present invention to provide a double-stranded nucleic acid in which at least one nucleic acid strand includes an unnatural base that forms a self-complementary base pair or an unnatural base that forms a base pair with any natural base with substantially the same thermal stability. It is another object of the present invention to provide a method of hybridizing a first nucleic acid strand with a second nucleic acid strand, wherein the first nucleic acid strand includes an unnatural base that forms a self-complementary base pair or an unnatural base that forms a base pair with any natural base with substantially the same thermal stability; a method of applying a nucleic acid including an unnatural base that forms a self-complementary base pair or an unnatural base that forms a base pair with any natural base with substantially the same thermal stability to SNP detection, a DNA chip, DNA/RNA computing, or an in vitro translation system; and a method of introducing an unnatural base that forms a self-complementary base pair or an unnatural base that forms a base pair with any natural base with substantially the same thermal stability into a nucleic acid strand and thereby controlling the thermodynamic stability in hybridization of the nucleic acid strand.

Solution to Problem

The present inventors, who have diligently studied to solve the above-mentioned problems, have found the following facts: An unnatural base Ds (7-(2-thienyl)-imidazo[4,5-b]pyridine) self-complementarily forms a stable base pair (Ds-Ds) in a double-stranded DNA (FIG. 1); the stability of the Ds-Ds base pair in a double-stranded DNA depends on the types of natural base pairs on both sides thereof; the dependence on both adjacent base pairs has a regularity, which is different from a preconceived idea that the stability of a double-stranded DNA containing the Ds-Ds base pair is high when the double-stranded DNA includes a large number of G-C base pairs; though the stability of a base pair of Ds and a natural base is less than that of the Ds-Ds base pair, Ds has properties as a universal base that forms a base pair with any natural base with substantially the same stability; an unnatural base Dss (7-(2,2'-bithiophen-5-yl)imidazo[4,5-b]pyridine), where a thiophene group is further linked to the thiophene moiety of Ds, also has similar properties; and if a mismatched base pair of natural bases is present at a position adjacent to a base pair of this Ds and a natural base in a double-stranded DNA, the thermal stability of the double-stranded DNA is significantly reduced.

This self-complementary Ds-Ds base pair can be used as a base pair of the third generation in various fields, for example, production of a novel DNA tag for hybridization, use in imaging technology such as a molecular beacon, use in replication or transcription in a combination with a Ds-Pa or Ds-Pn base pair, use in a DNA or RNA computer, and use as a novel codon or anticodon for incorporating a non-natural amino acid into protein. Furthermore, the inventors have found that a base pair of Ds and a natural base can be used in a DNA probe that can selectively identify a single-base mutation of a target gene.

The present inventors have also designed a method for estimating a melting temperature (Tm) value serving as an index of thermal stability of a double-stranded DNA containing a Ds-Ds base pair by a simple nearest-neighbor method. This method enables production of a DNA tag or probe of which mishybridization is reduced. The present inventors have also found that a base pair of Ds and a natural base (e.g., Ds-G base pair) in a double-stranded DNA reduces the stability of an adjacent mismatched base pair.

For comprehension of the present invention, the background to the present invention has been described above. The scope of the present invention, however, should not be limited to the above description, but be defined by the attached claims.

The present invention provides the following embodiments 1 to 20 as one aspect.

Embodiment 1: A double-stranded nucleic acid comprising a first nucleic acid strand and a second nucleic acid strand, wherein
the first nucleic acid strand contains a nucleotide or nucleotides each having an unnatural base represented by Formula I:

[Formula 1]

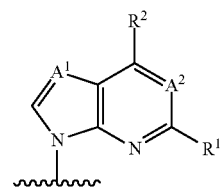

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]

or a derivative thereof as the base, and the second nucleic acid strand may or may not contain a nucleotide or nucleotides each having an unnatural base represented by Formula I or a derivative thereof as the base; and the unnatural base represented by Formula I or the derivative thereof in the first nucleic acid strand forms a base pair with any natural base or the unnatural base represented by Formula I or the derivative thereof in the second nucleic acid strand.

Embodiment 2: The double-stranded nucleic acid according to Embodiment 1, wherein
the unnatural base represented by Formula I is an unnatural base in which,
$A^1$ represents N;
$A^2$ represents CH;
$R^1$ represents hydrogen; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group.

Embodiment 3: The double-stranded nucleic acid according to Embodiment 1, wherein the unnatural base represented by Formula I or the derivative thereof is
a 7-(2-thienyl)imidazo[4,5-b]pyridin-3-yl group (Ds);
a 7-(2,2'-bithien-5-yl)imidazo[4,5-b]pyridin-3-yl group (Dss); or
a derivative thereof.

Embodiment 4: The double-stranded nucleic acid according to Embodiment 1, wherein the derivative of an unnatural base represented by Formula I is a derivative where the substituent shown as $R^2$ in Formula I is further modified by addition of a substituent.

Embodiment 5: The double-stranded nucleic acid according to any one of Embodiments 1 to 4, wherein the first nucleic acid strand contains a plurality of nucleotides each having an unnatural base represented by Formula I or a derivative thereof as the bases in such a manner that the nucleotides each having the unnatural base or its derivative as the base are not adjacent to each other in the first nucleic acid strand.

Embodiment 6: The double-stranded nucleic acid according to any one of Embodiments 1 to 5, wherein the first nucleic acid strand is a strand where the nucleotide adjacent to the 5' side of the nucleotide having an unnatural base represented by Formula I or a derivative thereof as the base is cytosine (C) or thymine (T) and/or the nucleotide adjacent to the 3' of the nucleotide having the unnatural base or its derivative is guanine (G).

Embodiment 7: A method of hybridizing a nucleic acid containing an unnatural base comprising:
hybridizing a first nucleic acid strand containing a nucleotide having an unnatural base represented by Formula I:

[Formula 2]

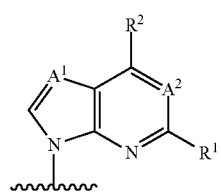

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base with a second nucleic acid strand which contains or which does not contain a nucleotide having an unnatural base represented by Formula I or a derivative thereof as the base, wherein
the unnatural base represented by Formula I or the derivative thereof in the first nucleic acid strand forms a base pair with any natural base or the unnatural base represented by Formula I or the derivative thereof in the second nucleic acid strand.

Embodiment 8: The method according to Embodiment 7, wherein the first nucleic acid strand is a probe, tag, or primer for hybridization.

Embodiment 9: The method according to Embodiment 7, wherein the first nucleic acid strand and the second nucleic acid strand are computation devices for a DNA computer.

Embodiment 10: The method according to Embodiment 7, wherein the first nucleic acid strand and the second nucleic acid strand are integrated devices for DNA or RNA origami.

Embodiment 11: The method according to any one of Embodiments 7 to 10, wherein hybridization is performed in a multiplex form.

Embodiment 12: A method of identifying a single-base mutation, comprising the steps of:
(a) preparing a probe complementary to a sequence containing a single-base mutation site to be identified in a target nucleic acid, wherein the probe includes a nucleotide having an unnatural base represented by Formula I:

[Formula 3]

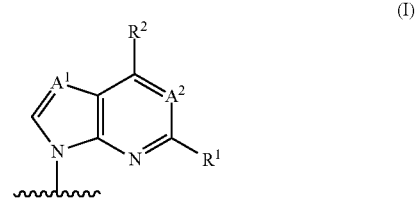

(I)

[wherein,
$A^1$ and $A^2$ each independently represent N or CH;
$R^1$ represents hydrogen or an amino group; and
$R^2$ represents, a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base at a position adjacent to the nucleotide complementary to the single-base mutation site to be identified;
(b) hybridizing a target nucleic acid strand with the probe of (a); and
(c) identifying that a target nucleic acid hybridized with the probe has a base complementary to the probe at the single-base mutation site to be identified.

Embodiment 13: A method of identifying a single-base mutation, comprising the steps of:

(a) preparing a primer complementary to a sequence containing a single-base mutation site to be identified in a target nucleic acid, wherein the primer includes a nucleotide having an unnatural base represented by Formula I:

[Formula 4]

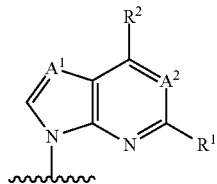

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-ter-thien-5-yl group]
or a derivative thereof as the base at a position adjacent to the nucleotide complementary to the single-base mutation site to be identified;
(b) performing PCR employing a target nucleic acid as the template and using the primer of (a), a nucleotide substrate having an unnatural base represented by Formula I or a derivative thereof as the base, a natural nucleotide substrate, and a DNA polymerase; and
(c) identifying that a target nucleic acid amplified by the PCR has a base complementary to the primer at a single-base mutation site to be identified.

Embodiment 14: A method of capturing a nucleic acid using a probe containing an unnatural base, comprising the steps of:
(a) preparing a probe containing a nucleotide having an unnatural base represented by Formula I:

[Formula 5]

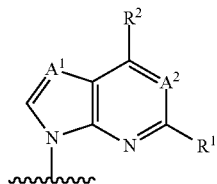

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-ter-thien-5-yl group]
or a derivative thereof as the base, and immobilizing the probe to a solid phase;
(b) adding a tag composed of a sequence complementary to the probe of (a) to a nucleic acid to be captured, wherein the tag includes a nucleotide having an unnatural base represented by Formula I or a derivative thereof as the base at a position complementary to the nucleotide having the unnatural base represented by Formula I or the derivative thereof as the base in the probe; and
(c) capturing a nucleic acid by hybridizing the probe immobilized to the solid phase in (a) with the nucleic acid provided with the tag in (b).

Embodiment 15: The method according to Embodiment 14, wherein the solid phase is a DNA chip substrate or a bead.

Embodiment 16: A method of DNA or RNA computing, comprising the steps of:
(a) preparing a plurality of nucleic acid strands as computation devices each containing a nucleotide having an unnatural base represented by Formula I:

[Formula 6]

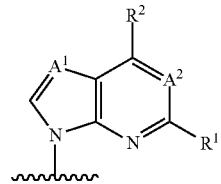

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-ter-thien-5-yl group]
or a derivative thereof as the base, where a part of one computation device is complementary to a part of another computation device, and the nucleotide having an unnatural base represented by Formula I or a derivative thereof as the base is arranged so that the complementary sites of the computation devices form a base pair; and
(b) hybridizing a part of one computation device with a part of another computation device.

Embodiment 17: In an embodiment, the present invention relates to a method of forming a DNA or RNA origami, comprising:
(a) preparing a plurality of nucleic acid strands as integrated devices each containing a nucleotide having an unnatural base represented by Formula I:

[Formula 7]

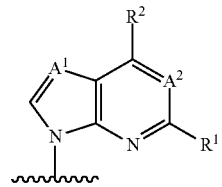

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base, where a part of one integrated device is complementary to a part of another integrated device, and the nucleotide having an unnatural base represented by Formula I or a derivative thereof as the base is arranged so that the complementary sites of the integrated devices form a base pair; and
(b) hybridizing a part of one integrated device with a part of another integrated device.

Embodiment 18: A method of synthesizing a peptide by an in vitro translation system, comprising the steps of:
(a) preparing a transfer RNA containing a nucleotide having an unnatural base represented by Formula I:

[Formula 8]

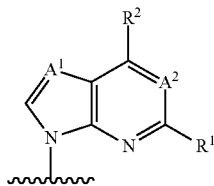

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base at an anticodon position;
(b) preparing a messenger RNA containing a nucleotide having an unnatural base represented by Formula I or a derivative thereof as the base in a coding sequence, where the nucleotide having an unnatural base represented by Formula I or a derivative thereof as the base in the messenger RNA is arranged as a codon corresponding to the anticodon position of the transfer RNA containing the unnatural base so that the nucleotides each having an unnatural base represented by Formula I or a derivative thereof as the base form a base pair in hybridization between codon and anticodon; and
(c) synthesizing a peptide by in vitro translation using the transfer RNA of (a), the messenger RNA of (b), and ribosome.

Embodiment 19: A method of controlling thermodynamic stability in nucleic acid hybridization, comprising:
substituting a nucleotide in a nucleic acid strand by a nucleotide having an unnatural base represented by Formula I:

[Formula 9]

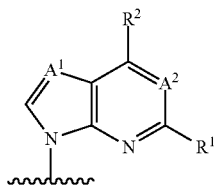

(I)

[wherein,
$A^1$ and $A^2$ each independently represent N or CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base.

Embodiment 20: The method according to Embodiment 19, wherein the nucleic acid strand is a probe, a primer, or an intramolecularly hybridizing single-stranded nucleic acid.

Advantageous Effects of Invention

The present inventors have found unnatural base pairs that can be synthesized easier than conventional unnatural bases (e.g., amidite reagents for DNA synthesis), and that shows stability comparable to that of a G-C base pair, such as a Ds-Ds self-complementary unnatural base pair. The present inventors also have found that the unnatural bases (unnatural bases represented by Formula I or derivatives thereof) such as Ds can form base pairs with any natural base with substantially the same stability and thereby show a property specific to a universal base. The unnatural bases such as a Ds base can be used as DNA tags for hybridization as the fifth base. The unnatural bases such as a Ds base can be introduced into DNA or RNA by complementing to unnatural bases such as Pa and Pn by replication or transcription using polymerase. Accordingly, for example, Ds can be introduced into a specific position in DNA or RNA using a Ds-Pa or Ds-Pn base pair that functions in replication and transcription. In addition, DNA or RNA as a target can be selectively detected by hybridization using a Ds-Ds base pair having high thermal stability or a base pair between Ds and a natural base, which shows a unique property.

BRIEF DESCRIPTION OF DRAWINGS

FIG. 1 schematically illustrates self-complementary Ds-Ds and Dss-Dss base pairs that form stable base pairs in double-stranded DNAs, and Ds-Pa and Ds-Pn base pairs that function in replication.

FIG. 2 schematically illustrates an example of application of nucleic acid having an unnatural base of the present invention, wherein (a): example of a DNA chip including a combination of a Ds-Pa or Ds-Pn base pair which functions in replication or transcription, and a self-complementary Ds-Ds base pair (multiplex is also possible), and (b): SNP analysis of a target gene using a DNA probe containing Ds. The stability of double strand formation between a probe and a target gene having a single-base mutation is considerably reduced by incorporating Ds into the probe, and thereby the target gene can be selectively identified.

FIG. 3 shows the results of investigation of thermal stability of double-stranded DNA fragments containing unnatural bases.

FIG. 4 shows the results of investigation of thermal stability of double-stranded DNAs by changing the natural base pairs adjacent to a complementary unnatural base pair Ds-Ds or a base pair of Ds and a natural base (G).

FIG. 8 schematically illustrates a method for estimating a Tm value from a sequence of a double-stranded DNA containing Ds, and includes a table showing the free energy ΔG of each nearest-neighbor sequence (incorporation of a Ds-Ds base pair by a known Nearest-neighbor method).

FIG. 10 shows thermal stability of double-stranded DNAs each containing a plurality of Ds-Ds base pairs.

FIG. 11 shows recognition ability of a mismatched pair of a natural base by a G-Ds base pair.

FIG. 12 shows neutralization of thermal stability, which depends on the GC contents in double-stranded DNAs, by a G-Ds base pair (each number in parentheses shows the number of G-C base pairs).

DESCRIPTION OF EMBODIMENTS

Figure 5:
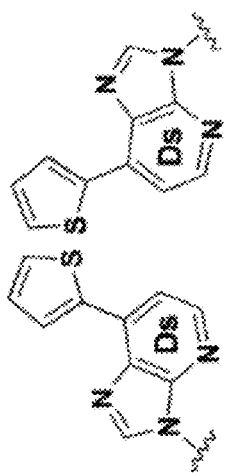
FIG. 5 shows changes in thermal stability of a double-stranded DNA depending on the natural base pairs on both sides of the Ds-Ds base pair in double-stranded DNA. The table in FIG. 5 shows the summary of the results shown in the upper table in FIG. 4.

The present invention will now be described in more detail.

DEFINITION

Unless otherwise specifically defined throughout the specification, the scientific terms and technical terms used in relation to the present invention are intended to have the same meanings as those generally used by those skilled in the art.

Throughout the specification, the term "nucleoside" refers to a glycosylated compound where a nucleic acid base and a reducing group of a carbohydrate are linked to each other by a glycoside bond. Here, the nucleic acid base is a concept including natural bases, i.e., adenine, guanine, cytosine, thymine, and uracil; modifications and analogs of the natural bases; and unnatural bases. The unnatural base refers to a functional group that is not a natural base, which can form a base pair with a natural base or another unnatural base in a nucleic acid in which the base is incorporated. Examples of the type of the unnatural base include, but not limited to, substituted or unsubstituted 2-aminopurine, substituted or unsubstituted imidazo[4,5-b]pyridine, substituted or unsubstituted pyrrolo[2,3-b]pyridine, substituted or unsubstituted pyridin-2-one, substituted or unsubstituted pyrrole-2-carbaldehyde, and substituted or unsubstituted 2-nitropyrrole, isoguanine, isocytosine, xanthosine, 2,4-diaminopyrimidine, 4-methylbenzimidazole, difluorotoluene, propynyl isocarbostyril, and 7-azaindole. The unnatural base may be a derivative of a natural base.

Throughout the specification, the term "nucleotide" refers to an ester compound formed of the carbohydrate moiety of the nucleoside and phosphoric acid. The nucleotide is more preferably a mono-, di-, or tri-phosphate ester.

The carbohydrate moiety of a nucleoside or a nucleotide may be ribofuranosyl, 2'-deoxyribofuranosyl, or 2'-substituted ribofuranosyl having a substituent such as a halogen on the 2'-position. In the phosphate moiety, the hydroxyl group at the γ-position of the phosphate is preferably, but not limited, replaced with a group selected from the group consisting of amino groups, methylamino groups, dimethylamino groups, mercapto groups, and fluoro groups. The carbohydrate moiety of a nucleoside or a nucleotide and the phosphate moiety of a nucleotide are only required to have structures recognized in known nucleoside, nucleotide, and derivatives thereof. The ribonucleotide having a carbohydrate moiety of ribofuranosyl is a constituent of ribonucleic acid (RNA), and the deoxyribonucleotide having a carbohydrate moiety of 2'-deoxyribofuranosyl is a constituent of deoxyribonucleic acid (DNA).

Throughout the specification, examples of the derivative of the nucleoside or the nucleotide include phosphoramidite derivatives and H-phosphonate derivatives.

The phosphoramidite derivative is a nucleoside in which one or more substituents are modified with protecting groups and is used in chemical synthesis of a nucleic acid (for example, Sambrook et al., Molecular Cloning: A Laboratory Manual, 3rd Edition, Cold Spring Harbor Laboratory, NY: Cold Spring Harbor (2001), 10.42-10.46). Specifically, the 5'-hydroxyl group of (deoxy)ribose can be protected by a 5'-position protecting group that is used in nucleic acid synthesis, such as a dimethoxytrityl group (DMT), a monomethoxytrityl group, or a levulinyl group. This is because the 5'-hydroxyl group is prevented from reacting with phosphoramidite nucleoside that is fed for chemical synthesis of a nucleic acid. The tri-valent phosphate group linked to the (deoxy)ribose residue of the phosphoramidite nucleoside to be fed can be protected by, for example, a diisopropylamino group for activation by, for example, tetrazole during bond formation. The tri-valent phosphate group can be also linked to, for example, a cyanoethyl or methoxy for suppressing the reaction of a side chain. Furthermore, the amino group of a purine ring of a base can be protected by, for example, a phenoxyacetyl group or an isobutyryl group for protecting the nucleophilic function of an exocyclic amino group. The phosphoramidite derivative of the present invention has these protecting groups introduced at one or more positions. Preferably, protecting groups are introduced to all the positions described above.

Throughout the specification, the term "nucleic acid" refers to a molecule of a nucleic acid strand where one or more nucleotides are linked to each other in the 5'→3' direction. The nucleic acids of the present invention include single-stranded and double-stranded RNAs and DNAs. The double strand may be DNA/DNA, RNA/RNA, or DNA/RNA. The DNAs include cDNA formed by reverse transcription using RNA as a template. Furthermore, nucleic acid can form a triple strand and a quadruple strand, for example.

Throughout the specification, the term "universal base" refers to a base analog that forms a base pair with any natural base with substantially the same stability.

Double-Stranded Nucleic Acid Including Unnatural Base

In an embodiment, the present invention provides a double-stranded nucleic acid including a first nucleic acid strand and a second nucleic acid strand, wherein the first nucleic acid strand contains a nucleotide or nucleotides each having an unnatural base represented by Formula I:

[Formula 10]

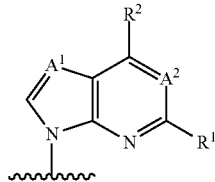

(I)

[wherein, $A^1$ and $A^2$ each independently represent N or CH;

$R^1$ represents hydrogen or an amino group; and $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]

or a derivative thereof as the base, and the second nucleic acid strand may or may not contain a nucleotide or nucleotides each having an unnatural base represented by Formula I or a derivative thereof as the base; and the unnatural base represented by Formula I or the derivative thereof in the first nucleic acid strand forms a base pair with any natural base or the unnatural base represented by Formula I or the derivative thereof in the second nucleic acid strand.

The unnatural base represented by Formula I or the derivative thereof can form a self-complementary base pair with an unnatural base represented by Formula I or a derivative thereof. In addition, the unnatural base represented by Formula I or the derivative thereof can form a base pair with any of the natural bases: adenine, guanine, cytosine, and thymine, with substantially the same stability and thus has properties as a universal base.

Accordingly, in the case of a second nucleic acid strand containing a nucleotide having an unnatural base represented by Formula I or a derivative thereof as the base, the unnatural base or its derivative is incorporated at the position complementary to the position of the nucleotide having an unnatural base represented by Formula I or a derivative thereof as the base in first nucleic acid strand. As a result, each of the unnatural bases represented by Formula I and the derivatives thereof of the first nucleic acid strand forms a base pair with a natural base or the unnatural base represented by Formula I or the derivative thereof of the second nucleic acid strand.

The first nucleic acid strand and the second nucleic acid strand may be completely complementary to each other. Alternatively, the double-stranded nucleic acid formed of a first nucleic acid strand and a second nucleic acid strand may include one or more mismatched base pairs.

The unnatural base represented by Formula I or a derivative thereof of the present invention is preferably an unnatural base represented by Formula I:

[Formula 11]

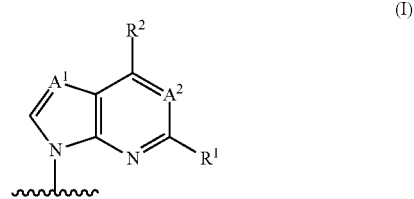

(I)

[wherein, $A^1$ represents N; $A^2$ represents CH;

$R^1$ represents hydrogen; and $R^2$ is selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]

or a derivative thereof.

More preferably, the unnatural base represented by Formula I or the derivative thereof may be an unnatural base selected from the group consisting of:

a 7-(2-thienyl)imidazo[4,5-b]pyridin-3-yl group (Ds);
a 7-(2,2'-bithien-5-yl)imidazo[4,5-b]pyridin-3-yl group (Dss);
a 7-(2,2',5',2"-terthien-5-yl)imidazo[4,5-b]pyridin-3-yl group (Dsss);
a 2-amino-6-(2-thienyl)purin-9-yl group (s);
a 2-amino-6-(2,2'-bithien-5-yl)purin-9-yl group (ss);
a 2-amino-6-(2,2',5',2"-terthien-5-yl)purin-9-yl group (sss);
a 4-(2-thienyl)-pyrrolo[2,3-b]pyridin-1-yl group (dDsa);
a 4-(2,2'-bithien-5-yl)-pyrrolo[2,3-b]pyridin-1-yl group (Dsas);
a 4-[2-(2-thiazolyl)thien-5-yl]pyrrolo[2,3-b]pyridin-1-yl group (Dsav);
a 4-(2-thiazolyl)-pyrrolo[2,3-b]pyridin-1-yl group (dDva);
a 4-[5-(2-thienyl)thiazol-2-yl]pyrrolo[2,3-b]pyridin-1-yl group (Dvas); and
a 4-(2-imidazolyl)-pyrrolo[2,3-b]pyridin-1-yl group (dDia).

More preferably, the unnatural base represented by Formula I or the derivative thereof may be a 7-(2-thienyl)imidazo[4,5-b]pyridin-3-yl group (Ds) or a 7-(2,2'-bithien-5-yl)imidazo[4,5-b]pyridin-3-yl group (Dss), or a derivative thereof.

Throughout the specification, the derivative of an unnatural base represented by Formula I may be any unnatural base having the skeletal structure represented by Formula I. For example, the derivative may be an unnatural base derivative where the substituent shown as $R^2$ in Formula I is further modified by addition of a substituent, such as a $C_1$-$C_3$ alkyl group, a $C_1$-$C_3$ alkenyl group, or a $C_1$-$C_3$ alkynyl group. Alternatively, derivatives where the functional groups of the unnatural bases of the present invention are modified with protecting groups are also included in the derivatives of an unnatural base of the present invention. Specific examples of the appropriate protecting group for protecting the amino group of the unnatural base of the present invention include a phenoxyacetyl group, an isobutyryl group, and a dimethyl formamidyl group.

In another embodiment, the first nucleic acid strand in the double-stranded nucleic acid of the present invention may contain a plurality of nucleotides each having an unnatural base represented by Formula I or a derivative thereof as the base. In such a case, if the unnatural bases represented by Formula I or the derivatives thereof are adjacent to each other in the first nucleic acid nucleotide strand, the thermal stability of the double-stranded nucleic acid decreases. The plurality of nucleotides in the first nucleic acid strand are preferably not adjacent to each other in the nucleotide strand.

In the case of a first nucleic acid strand containing a plurality of nucleotides each having an unnatural base represented by Formula I or a derivative thereof as the base, the second nucleic acid strand may or may not contain a plurality of nucleotides each having an unnatural base or a derivative thereof as the base. In the case of a second nucleic acid strand containing a nucleotide having an unnatural base represented by Formula I or a derivative thereof as the base, the nucleotide having an unnatural base or its derivative as the base is incorporated at the position complementary to the position of a nucleotide having an unnatural base represented by Formula I or a derivative thereof as the base of the first nucleic acid strand. As a result, the unnatural bases represented by Formula I or the derivatives thereof of the first nucleic acid strand each form a base pair with a natural base or the unnatural base represented by Formula I or the derivative thereof of the second nucleic acid strand.

In the case of forming a double-stranded nucleic acid by hybridization between a first nucleic acid strand containing a nucleotide having an unnatural base represented by Formula I or a derivative thereof as the base and a second nucleic acid strand, the thermal stability varies depending on the nucleotides adjacent to the nucleotide having an unnatural base represented by Formula I or a derivative thereof as the base in the first nucleic acid strand. That is, the order of stability from the highest to the lowest is: 5'-CDsG-3'>5'-CDsA-3'>5'-TDsG-3'>5'-GDsG-3'>5'-TDsA-3'>5'-ADsG-3'>5'-GDsA-3'>5'-GDsC-3'>5'-ADsA-3'>5'-ADsC-3'>5'-ADsT-3'. Accordingly, in a preferred embodiment, the first nucleic acid strand in a double-stranded nucleic acid of the present invention has a cytosine (C) or thymine (T) nucleotide so as to be adjacent to the 5' side of a nucleotide having an unnatural base represented by Formula I or a derivative thereof as the base, and/or a guanine (G) nucleotide so as to be adjacent to the 3' side of the nucleotide.

The unnatural base represented by Formula I or the derivative thereof forms a self-complementary base pair with an unnatural base represented by Formula I or a derivative thereof through a hydrophobic interaction. It is believed that since the base pair formation is not achieved by hydrogen bonding, the unnatural base represented by Formula I or the derivative thereof can form a stable base pair with any of the natural bases: adenine, guanine, cytosine, and thymine, with substantially the same stability and thus has properties as a universal base. Accordingly, a bulky hydrophobic unnatural base, for example, an unnatural base composed of a functional group containing a nine or more membered aryl group or heteroaryl group, also probably has the characteristics of the unnatural base represented by Formula I or the derivative thereof, such as a property of forming a self-complementary base pair and a property as a universal base.

Accordingly, the present invention also provides a double-stranded nucleic acid including a first nucleic acid strand and a second nucleic acid strand, wherein the first nucleic acid strand contains at least a nucleotide including a functional group containing a nine or more membered aryl group or heteroaryl group as an unnatural base; the second nucleic acid strand may or may not contain a nucleotide or nucleotides each having an unnatural base represented by Formula I or a derivative thereof as the base; and the unnatural base in the first nucleic acid strand forms a base pair with any natural base or the unnatural base in the second nucleic acid strand.

Examples of the functional group containing a nine or more membered aryl group or heteroaryl group include, but not limited to, functional groups in the following Groups 1 to 7:

Group 1

Unnatural bases, which are functional groups represented by the formula:

[Formula 12]

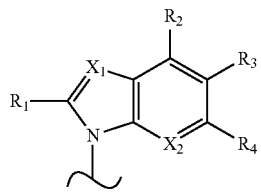

[wherein, $X_1$ and $X_2$ are each independently selected from the group consisting of CH, CF, and N; and $R_1$, $R_2$, $R_3$, and $R_4$ are each independently selected from the group consisting of hydrogen, Cl, F, $CH_3$, phenyl, and $NO_2$] or derivatives thereof.

Examples of the unnatural base belonging to Group 1 include:

4-Methylindole (in the formula above, $X_1=X_2=CH$, $R_1=R_3=R_4=H$, $R_2=CH_3$) which is described by Guckian, et al. (J. Am. Chem. Soc., 118: 8182-8183 (1996));

D base (in the formula above, $X_1=X_2=CH$, $R_1=R_3=H$, $R_2=R_4=CH_3$) which is described by Schweitzer, et al. (J. Org. Chem., 59: 7238-7242 (1994));

Q base (in the formula above, $X_1=X_2=N$, $R_1=R_3=R_4=H$, $R_2=CH_3$) which is described by Morales, et al. (J. Am. Chem. Soc., 121: 2323-2324 (1999));

Z base (in the formula above, $X_1=N$, $X_2=CH$, $R_1=R_3=R_4=H$, $R_2=CH_3$) which is described by Guckian, et al. (J. Org. Chem., 63: 9652-9656 (1998));

A base (in the formula above, $X_1=X_2=CH$, $R_1=C_1$, $R_2=F$, $R_3=R_4=H$) and a base (in the formula above, $X_1=N$, $X_2=CH$, $R_1=C_1$, $R_2=CH_3$, $R_3=R_4=H$) which are described by Taniguchi, et al. (J. Am. Chem. Soc., 129: 8836-8844 (2007));

$^F$I base (in the formula above, $X_1=CH$, $X_2=CF$, $R_1=H$, $R_2=R_3=R_4=F$) which is described by Lai, et al. (J. Am. Chem. Soc., 126: 3040-3041 (2004));

An indole base (in the formula above, $X_1=X_2=CH$, $R_1=R_2=R_3=R_4=H$) which is described by Girgis, et al. (J. Heterocycl. Chem., 25: 361-366 (1988));

5-nitroindole base (in the formula above, $X_1=X_2=CH$, $R_1=R_2=R_4=H$, $R_3=NO_2$) which is described by Loakes, et al. (Nucleic Acids Res., 22: 4039-4043 (1994));

5-PhI base (in the formula above, $X_1=X_2=CH$, $R_1=R_2=R_4=H$, $R_3$=phenyl) which is described by Krueger, et al. (Curr. Opin. Chem. Biol., 11: 588-594 (2007)); and DNB base (in the formula above, $X_1=N$, $X_2=CH$, $R_1=R_2=H$, $R_3=R_4=NO_2$) which is described by Krueger, et al. (Chem. Biol., 16: 242-248 (2009)).

Group 2

Unnatural bases, which are functional groups represented by the formula:

[Formula 13]

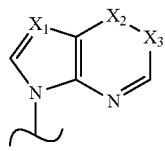

[wherein, $X_1$, $X_2$, and $X_3$ each independently represent CH or N]

or derivatives thereof.

Examples of the unnatural base belonging to Group 2 include:

PP base (in the formula above, $X_1=X_3=CH$, $X_2=N$) and ImPy base (in the formula above, $X_1=N$, $X_2=X_3=CH$) which are described by Wu, et al. (J. Am. Chem. Soc., 122: 7621-7632 (2000));

Neb base (in the formula above, $X_1=X_3=N$, $X_2=CH$) which is described by Leconte, et al. (J. Am. Chem. Soc., 130: 2336-2343 (2008)); and 7AI base (in the formula above, $X_1=X_2=X_3=CH$) which is described in Ogawa, et al. (J. Am. Chem. Soc., 122: 3274-3287 (2000)).

Group 3

Unnatural bases, which are functional groups represented by the formula:

[Formula 14]

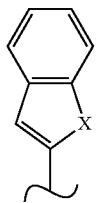

[wherein, X is selected from NH, O, and S), or derivatives thereof; or

Unnatural bases, which are a functional group (BTz base) represented by the formula:

[Formula 15]

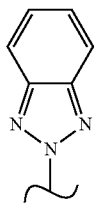

or derivatives thereof.

Examples of the unnatural base belonging to Group 3 include BTp base (in the formula above, X=S), BFr base (in the formula above, X=O), IN base (in the formula above, X=NH), and BTz base which are described by Matsuda, et al. (J. Am. Chem. Soc., 125: 6134-6139 (2003)).

Group 4

Unnatural bases, which are functional groups represented by the formula:

[Formula 16]

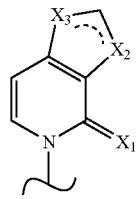

[wherein, $X_1$ represents O or S; and $X_2$ and $X_3$ are selected from CH, O, and S], or derivatives thereof.

Examples of the unnatural base represented by the formula above include:

7OFP base (in the formula above, $X_1=X_2=O$, $X_3=CH$), 4TFP base (in the formula above, $X_1=S$, $X_2=CH$, $X_3=O$), 4OFP base (in the formula above, $X_1=O$, $X_2=CH$, $X_3=O$), 7OTP base (in the formula above, $X_1=O$, $X_2=5$, $X_3=CH$), 4OTP base (in the formula above, $X_1=O$, $X_2=CH$, $X_3=S$), and 7TFP base (in the formula above, $X_1=S$, $X_2=O$, $X_3=CH$) which are described by Henry, et al. (J. Am. Chem. Soc., 125: 9638-9646 (2003)).

Alternatively, the unnatural base belonging to Group 4 may be an unnatural base represented by the following formula:

[Formula 17]

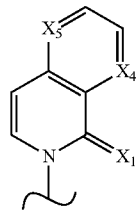

[wherein, $X_1$ represents O or S; and $X_4$ and $X_5$ are CH or N], or a derivative thereof.

Examples of the unnatural base represented by the formula above include:

NICS base (in the formula above, $X_1=O$, $X_4=CH$, $X_5=N$), SNICS base (in the formula above, $X_1=S$, $X_4=CH$, $X_5=N$), and SICS base (in the formula above, $X_1=S$, $X_4=X_5=CH$) which are described by Yu, et al. (Angew. Chem. Int. Ed., 41: 3841-3844 (2002);

ICS base (in the formula above, $X_1=O$, $X_4=X_5=CH$) which is described by Ogawa, et al. (J. Am. Chem. Soc., 122: 324-3287 (2000)); and oNICS base (in the formula above, $X_1=O$, $X_4=N$, $X_5=CH$) and SoNICS base (in the formula above, $X_1=S$, $X_4=N$, $X_5=CH$) which are described by Leconte, et al. (J. Am. Chem. Soc., 130: 2336-2343 (2008)).

Group 5
Unnatural bases, which are functional groups represented by the formula:

[Formula 18]

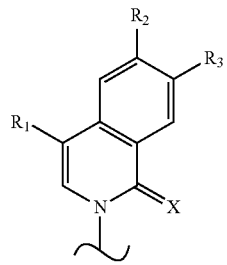

[wherein, X represents O or S; and
R$_1$, R$_2$, and R$_3$ each independently represent H, CH$_3$, or —C≡C—CH$_3$]
or derivatives thereof.

Examples of the unnatural base belonging to Group 5 include:
PICS base (in the formula above, X=O, R$_1$=—C≡C—CH$_3$, R$_2$=R$_3$=H) which is described by McMinn, et al. (J. Am. Chem. Soc., 121: 11585-11586 (1999)); and
5SICS base (in the formula above, X=S, R$_1$=H, R$_2$=—CH$_3$, R$_3$=H) and 4SICS base (in the formula above, X=S, R$_1$=H, R$_2$=H, R$_3$=CH$_3$) which are described by Leconte, et al. (J. Am. Chem. Soc., 130: 2336-2343 (2008)).

Group 6
Unnatural bases, which are functional groups represented by the formula:

[Formula 19]

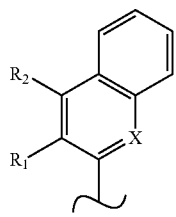

[wherein, X represents CH, C—CH$_3$, or N; and
R$_1$ and R$_2$ each independently represent H, CH$_3$, or —OCH$_3$]
or derivatives thereof.

Examples of the unnatural base belonging to Group 6 include:
2Np base (in the formula above, X=CH, R$_1$=R$_2$=H) which is described by Ren, et al. (J. Am. Chem. Soc., 118, 7671-7678 (1996));
2MN base (in the formula above, X=CH, R$_1$=CH$_3$, R$_2$=H) and DMN base (in the formula above, X=C—CH$_3$, R$_1$=H, R$_2$=CH$_3$) which are described by Ogawa, et al. (J. Am. Chem. Soc., 122: 3274-3287 (2000));
3MN base (in the formula above, X=CH, R$_1$=H, R$_2$=CH$_3$) which is described by Ogawa, et al. (J. Am. Chem. Soc., 122: 8803-8804 (2000));
NaM base (in the formula above, X=CH, R$_1$=OCH$_3$, R$_2$=H) which is described by Seo, et al. (J. Am. Chem. Soc., 131: 3246-3252 (2009)); and
QL base (in the formula above, X=N, R$_1$=R$_2$=H) which is described by'Hari, et al. (ChemBioChem, 9: 2769-2799 (2008)).

Others
Examples of the bulky hydrophobic unnatural base also include unnatural bases which are functional groups such as naphthalene bases, phenanthrene bases, pyrene bases, benzopyrene bases, perylene bases, and oxyperylene bases which are described by Ren, et al. (J. Am. Chem. Soc., 118: 7671-7678 (1996)), Gao, et al. (J. Am. Chem. Soc., 126: 12748-12749 (2004)), or Gao, et al. (J. Am. Chem. Soc., 124: 11590-11591 (2002)), or derivatives thereof.

[Formula 20]

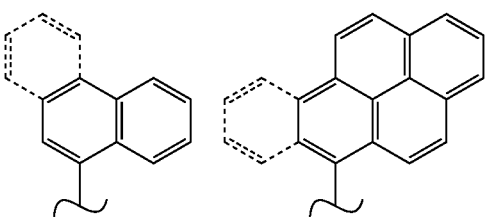

12. naphthalene
13. phenanthrene
14. pyrene
15. benzopyrene

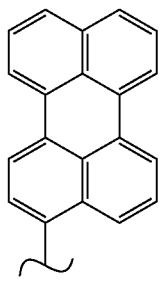 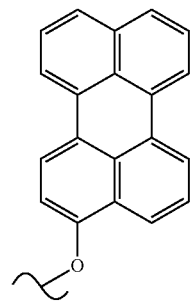

16. perylene
17. oxoperylene

Examples of the bulky hydrophobic unnatural base also include a coumarin base:

[Formula 21]

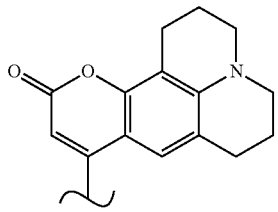

or derivatives thereof, described by Coleman, et al. (J. Org. Chem., 63: 5700-5703 (1998)).

Production of Nucleic Acid of the Present Invention
A nucleotide having an unnatural base represented by Formula I or a derivative thereof as the base can be introduced into the first nucleic acid strand or the second nucleic acid strand of a double-stranded nucleic acid of the present invention by utilizing a method of replication, transcription, or reverse transcription, or chemical synthesis, thereby introducing a nucleotide having the unnatural base represented by Formula I or a derivative thereof as a base.

(A) Method by Replication, Transcription, and Reverse Transcription
In a method of introducing a nucleotide having an unnatural base represented by Formula I or a derivative thereof as the base into the first or the second nucleic acid strand by replication, transcription, or reverse transcription, a nucleic acid containing a nucleotide having a base represented by Formula II (hereinafter referred to as Pa derivative):

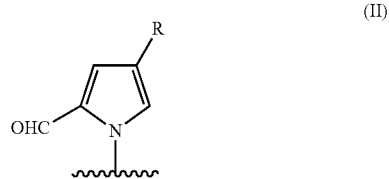

(II)

[wherein, R is selected from the group consisting of hydrogen and substituted or unsubstituted alkyl, alkenyl, and alkynyl groups, wherein
the substituent of the substituted alkyl, alkenyl, or alkynyl group is a functional group or a fluorescent functional group] is used as a template;
replication, transcription, or reverse transcription of a nucleic acid is performed by using deoxyribonucleoside 5'-triphosphate or ribonucleoside 5'-triphosphate including an unnatural base represented by Formula I as a replication substrate; and
a nucleic acid containing a base pair of the base Pa derivative and the unnatural base represented by Formula I is generated and a nucleotide having the unnatural base represented by Formula I is introduced into DNA or RNA.

The unnatural base of the present invention can form a base pair with another unnatural base, i.e., a Pa derivative. The Pa derivative, which is a complementary base of the unnatural base of the present invention, is incorporated into a template strand DNA; and the unnatural base of the present invention is incorporated into DNA or RNA by complementation of the unnatural base of the present invention to the Pa derivative of the template DNA by nucleic acid replication using a DNA polymerase, an RNA polymerase, or a reverse transcriptase. That is, the unnatural base of the present invention can be selectively introduced into a specific site of DNA or RNA by complementing to Pa in the template DNA.

The replication, transcription, and reverse transcription of nucleic acid in the method can be performed by known methods. Those skilled in the art can appropriately determine reaction conditions, such as selection of enzyme, selection of substrate concentration, and selection of annealing conditions, and such determination is within a range of matter that is routinely performed by those skilled in the art. However, the concentration ratio of an unnatural base to a nucleotide substrate during replication, transcription, or reverse transcription of nucleic acid is preferably lower than that of each natural base to a nucleotide substrate, for performing efficient replication, transcription, and reverse transcription of nucleic acid. For example, the concentration ratio of an unnatural base to the nucleotide substrate is ½ or less, ⅕ or less, 1/10 or less, 1/20 or less, or 1/100 or less of that of each natural base to the nucleotide substrate.

Examples of the DNA polymerase that can be used for introduction of a nucleoside having an unnatural base represented by Formula I or a derivative thereof as the base into the first or the second nucleic acid strand by the above-described method include the Klenow fragment of *Escherichia coli*, T4 DNA polymerase, Phi29 DNA polymerase, Bst DNA polymerase, and heat-resistant polymerases such as Pfu, DeepVent, Vent, Titanium Taq, and KlenTaq. The nucleotide having the unnatural base of the present invention that can be used as a substrate in this case is deoxyribonucleoside-5'-triphosphate.

Examples of the RNA polymerase that can be used for introduction of a nucleotide having an unnatural base represented by Formula I or a derivative thereof as the base into the first or the second nucleic acid strand by the above-described method include phage-derived RNA polymerases such as T7 RNA polymerase, T3 RNA polymerase, and SP6 RNA polymerase; and RNA-dependent RNA polymerases such as Qβ replicase. The nucleotide having the unnatural base of the present invention that can be used as a substrate in this case is ribonucleoside-5'-triphosphate.

Examples of the reverse transcriptase that can be used for introduction of a nucleotide having an unnatural base represented by Formula I or a derivative thereof as the base into the first or the second nucleic acid strand by the above-described method include reverse transcriptases derived from HIV, AMV, or MMLV. The nucleotide having the unnatural base of the present invention that can be used as a substrate in this case is deoxyribonucleoside-5'-triphosphate.

(B) Method by Chemical Synthesis

A nucleotide having an unnatural base represented by Formula I or a derivative thereof as the base can be introduced into the first or second nucleic acid strand by chemical synthesis utilizing DNA or RNA synthesis using a phosphoramidite, H-phosphonate, or triphosphate derivative of a nucleoside having an unnatural base represented by Formula I or a derivative thereof.

The method of synthesizing DNA or RNA using a phosphoramidite, H-phosphonate, or triphosphate derivative of a nucleoside is known to those skilled in the art. Those skilled in the art can determine reaction conditions suitable for an unnatural base or a derivative thereof of the present invention.

Method of Hybridizing Nucleic Acid Containing Unnatural Base

The unnatural base represented by Formula I or a derivative thereof of the present invention can form a self-complementary base pair with an unnatural base represented by Formula I or a derivative thereof. In addition, the unnatural base represented by Formula I or a derivative thereof can form a base pair with any of the natural bases: adenine, guanine, cytosine, and thymine, with substantially the same stability.

The present invention provides a method of hybridizing a nucleic acid containing an unnatural base by utilizing the above-described properties of the unnatural base represented by Formula I or a derivative thereof. That is, the present invention provides a method of hybridizing a nucleic acid containing an unnatural base, and the method comprising:
hybridizing a first nucleic acid strand containing a nucleotide having an unnatural base represented by Formula I:

[Formula 23]

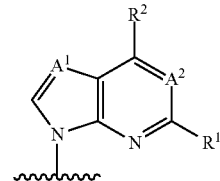

(I)

[wherein,
$A^1$ and $A^2$ each independently represent N or CH;
$R^1$ represents hydrogen or an amino group; and R² represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base with a second nucleic acid strand which contains or which does not contain a nucleotide having an unnatural base represented by Formula I or a derivative thereof as the base, wherein
the unnatural base represented by Formula I or the derivative thereof in the first nucleic acid strand forms a base pair with any natural base or the unnatural base represented by Formula I or the derivative thereof in the second nucleic acid strand.

In the case of hybridization of nucleic acid composed of natural bases, the thermal stability of double-stranded DNAs varies depending on a difference in content of GC even if the double-stranded DNAs have the same length. That is, the thermal stability of a double-stranded DNA increases with the GC content. Consequently, in the case of multiplex detection at a constant temperature using a plurality of fragments having different GC contents, a probe having a high GC content tends to cause mishybridization. In contrast to this, the nucleotide having an unnatural base represented by Formula I or a derivative thereof as the base of the present invention can control the thermodynamic stability in hybridization of the first and second nucleic acid strands by introducing the nucleotide introduced into the nucleic acid strand(s). Accordingly, even in the case of a plurality of pairs of first nucleic acid strand and second nucleic acid strand having different GC contents, the thermodynamic stability in hybridization of each nucleic acid pair can be controlled to be constant by introducing a nucleotide having an unnatural base represented by Formula I or a derivative thereof as the base into the nucleic acid strands. Consequently, in the method of the present invention, multiplex hybridization is possible.

In a preferred embodiment, the first nucleic acid strand in the method of the present invention can be a probe, tag, or primer for hybridization.

In another preferred embodiment, the first and second nucleic acid strands in the method of the present invention can be computation devices for a DNA computer.

The method of the present invention can be applied to various technical fields utilizing hybridization of nucleic acid, for example, SNP detection, a probe of DNA chip, a DNA tag, imaging technologies such as a molecular beacon, DNA/RNA computing, and introduction to translation systems such as codon/anticodon.

Application to Single Nucleotide Polymorphism Detection

The present inventors have found that the unnatural base represented by Formula I or a derivative thereof forms also a base pair with any natural base with a certain stability. Further, the present inventors have found that the stability of a double-stranded DNA is considerably reduced if the base pair adjacent to a base pair of an unnatural base represented by Formula I or a derivative thereof and a natural base is a mismatched pair (a combination other than A-T and G-C pairs). Specifically, the present inventors have found that the difference between the Tm value of a nucleic acid pair not containing a mismatched pair adjacent to a base pair of an unnatural base represented by Formula I or a derivative thereof and a natural base and that of a nucleic acid pair containing the mismatched pair is larger than the difference between the Tm value of nucleic acid pairs of only natural bases which is completely complementary and that of a pair containing a mismatched base pair. Thereby the present inventors have found that the single nucleotide polymorphism (SNP) can be detected using the first nucleic acid strand for hybridization of the present invention as a probe for hybridization or a primer for PCR.

(A) SNP Detection by Hybridization

In an embodiment, the present invention provides a method of identifying a single-base mutation, the method comprising the following steps of:

(a) preparing a probe complementary to a sequence containing a single-base mutation site to be identified in a target nucleic acid, wherein the probe includes a nucleotide having an unnatural base represented by Formula I:

[Formula 24]

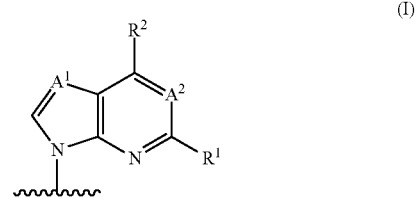

(I)

[wherein,
A¹ and A² each independently represent N or CH;
R¹ represents hydrogen or an amino group; and
R² represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof as the base so as to be adjacent to the nucleotide complementary to the single-base mutation site to be identified;

(b) hybridizing the target nucleic acid with the probe of (a); and (c) identifying that a target nucleic acid hybridized with the probe has a base complementary to the probe at the single-base mutation site to be identified.

In the above method, the temperature for hybridization is set to be lower than the Tm in the case where the probe comprising the unnatural base represented by Formula I or derivative thereof and a target nucleic acid which do not include a mismatched base pair at the position adjacent to a nucleotide having the unnatural base represented by Formula I or a derivative thereof of the probe, and is set to be higher than the Tm in the case where the probe comprising the unnatural base represented by Formula I or derivative thereof and a target nucleic acid which includes a mismatched base pair at the position adjacent to the nucleotide having the unnatural base represented by Formula I or derivative thereof of the probe. As a result, SNP can be identified by detecting a pair not containing a mismatched base pair.

The Tm value when a probe containing an unnatural base represented by Formula I or a derivative thereof is hybridized with a target nucleic acid can be determined based on the index described below. Alternatively, the Tm also can be confirmed by hybridization experiment.

FIG. 2(b) is a schematic diagram illustrating this embodiment.

(B) SNP Detection by PCR

In another embodiment, the present invention provides a method of identifying a single-base mutation, the method comprising the following steps of:

(a) preparing a primer complementary to a sequence containing a single-base mutation site to be identified in a target nucleic acid, wherein the primer includes a nucleotide having an PO unnatural base represented by Formula I:

[Formula 25]

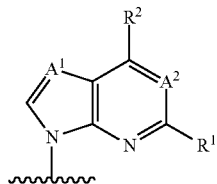

(I)

[wherein,
A$^1$ and A$^2$ each independently represent N or CH;
R$^1$ represents hydrogen or an amino group; and
R$^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]
or a derivative thereof as the base so as to be adjacent to the nucleotide complementary to the single-base mutation site to be identified;

(b) performing PCR employing a target nucleic acid as the template and using the primer of (a), a nucleotide substrate having an unnatural base represented by Formula I or a derivative thereof, a natural nucleotide substrate, and a DNA polymerase; and (c) identifying that a target nucleic acid amplified by the PCR has a base complementary to the primer at a single-base mutation site to be identified.

PCR can be performed by a method known to those skilled in the art. The nucleotide substrate may be a nucleoside 5'-triphosphate. When the template strand is a nucleic acid containing a nucleotide having an unnatural base represented by Formula I or a derivative thereof as the base, a nucleotide substrate having an unnatural base represented by Formula I or a derivative thereof is introduced at the position complementary to the unnatural base represented by Formula I or the derivative thereof.

Application to DNA Chip

In another embodiment, the present invention provides a method of capturing a nucleic acid using a probe containing an unnatural base, the method comprising the following steps of:

(a) preparing a probe containing a nucleotide having an unnatural base represented by Formula I:

[Formula 26]

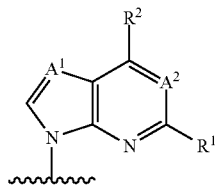

(I)

[wherein,
A$^1$ and A$^2$ each independently represent N or CH;
R$^1$ represents hydrogen or an amino group; and
R$^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]
or a derivative thereof as the base, and immobilizing the probe to a solid phase;

(b) adding a tag composed of a sequence complementary to the probe of (a) to a nucleic acid to be captured, wherein the tag includes a nucleotide having an unnatural base represented by Formula I or a derivative thereof as the base at the position complementary to the nucleotide having the unnatural base represented by Formula I or the derivative thereof as the base in the probe; and (c) capturing the nucleic acid by hybridizing the probe immobilized to the solid phase in (a) with the nucleic acid provided with the tag in (b).

In a preferred embodiment, the solid phase is a DNA chip substrate or a bead.

The thermal stability of a double-stranded nucleic acid composed of a probe and a tag can be controlled by introducing a nucleotide having an unnatural base represented by Formula I or a derivative thereof of the present invention into the probe or the tag. Accordingly, the hybridization of the probe and the tag is low in mishybridization and is therefore suitable for multiplex analysis.

The probe can be immobilized to the solid phase by a method known to those skilled in the art.

The tag can be added to a nucleic acid to be captured by, for example, utilizing PCR using formation of a base pair of an unnatural base represented by Formula I or a derivative thereof and a Pa base (Pa: pyrrole-2-carbaldehyde) or a Pn base (Pn: 2-nitropyrrole). Specifically, a strand complementary to the target nucleic acid to be captured is employed as a template, and PCR is performed using a primer having a Pa base or a Pn base, a natural nucleotide substrate and a nucleotide substrate including an unnatural base represented by Formula I or a derivative thereof as the base, and a DNA polymerase. Since a nucleotide substrate containing an unnatural base represented by Formula I or a derivative thereof as the base is introduced to the position complementary to the Pa base or Pn base, a tag containing an unnatural base represented by Formula I or a derivative thereof as the base can be introduced into the nucleic acid to be captured (see schematic diagram shown in FIG. 2(a)).

The temperature for hybridizing the probe with the tag can be appropriately set by those skilled in the art. Preferably, it is near the Tm of the double-stranded nucleic acid composed of the probe containing an unnatural base represented by Formula I or a derivative thereof and the tag. The Tm value when the probe containing an unnatural base represented by Formula I or a derivative thereof is hybridized with the tag can be determined based on the index described below. Alternatively, the Tm also can be confirmed by hybridization experiment.

Application to DNA or RNA Computing

In another embodiment, the present invention provides a method of DNA or RNA computing, the method comprising the following steps of:

(a) preparing a plurality of nucleic acid strands as computation devices each containing a nucleotide having an unnatural base represented by Formula I:

[Formula 27]

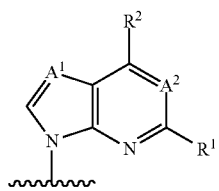

[wherein,
A¹ and A² each independently represent N or CH;
R¹ represents hydrogen or an amino group; and
R² represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]
or a derivative thereof as the base, where a part of one computation device is complementary to a part of another computation device, and the nucleotide having an unnatural base represented by Formula I or a derivative thereof as the base is arranged so that the complementary sites of the computation devices form a base pair; and
(b) hybridizing a part of one computation device with a part of another computation device.

DNA computing is a computation technique using DNA as a computation device, proposed by Adleman in 1994. In an example thereof, each choice in a matching question is expressed as a base sequence of DNA; these DNAs are hybridized and then amplified by, for example, PCR; an amplification product is selected from the resulting amplification products on the basis of indices such as an optimum length and a specific sequence that should be possessed; and an optimum solution of the matching question is obtained by sequence analysis of the selected amplification product.

The unnatural base represented by Formula I or a derivative thereof of the present invention provides a novel base pair that is different from that of natural bases. Accordingly, the variation of computation devices for the DNA computing can be increased.

The computation devices of the DNA computating may be not only DNA, but also RNA. In the case using RNA as a computation device, it is called RNA computating.

Application to DNA or RNA Origami

In another embodiment, the present invention provides a method of forming a DNA or RNA origami, the method comprising the following steps of:
(a) preparing a plurality of nucleic acid strands as integrated devices each containing a nucleotide having an unnatural base represented by Formula I:

[Formula 28]

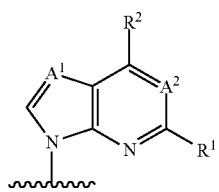

[wherein,
A¹ and A² each independently represent N or CH;
R¹ represents hydrogen or an amino group; and
R² represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]
or a derivative thereof as the base, where a part of one integrated device is complementary to a part of another integrated device, and the nucleotide having an unnatural base represented by Formula I or a derivative thereof is arranged so that the complementary sites of the integrated devices form a base pair; and
(b) hybridizing a part of one integrated device with a part of another integrated device.

DNA origami is a collective term of nano-scale folded structures for creating any two- or three-dimensional structure of nano-scales using DNA as integrated devices. DNA origami provides a useful nano-scale structure through interaction between complementary base sequences. In the case using RNA as an integrated device, it is called RNA origami.

Application to Translation System

In another embodiment, the present invention provides a method of synthesizing a peptide by an in vitro translation system, the method comprising the following steps of:
(a) preparing a transfer RNA containing a nucleotide having an unnatural base represented by Formula I:

[Formula 29]

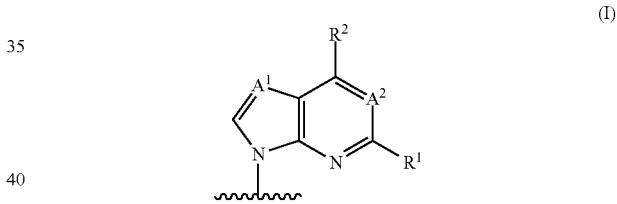

[wherein,
A¹ and A² each independently represent N or CH;
R¹ represents hydrogen or an amino group; and
R² represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]
or a derivative thereof as the base at an anticodon position;
(b) preparing a messenger RNA containing a nucleotide having an unnatural base represented by Formula I or a derivative thereof as the base in a coding sequence, where the nucleotide having an unnatural base represented by Formula I or a derivative thereof as the base in the messenger RNA is arranged as a codon corresponding to the anticodon position of the transfer RNA containing the unnatural base so that the nucleotides each having an unnatural base represented by Formula I or a derivative thereof as the base form a base pair in hybridization between codon and anticodon; and
(c) synthesizing a peptide by in vitro translation using the transfer RNA of (a), the messenger RNA of (b), and ribosome.

The transfer RNA containing a nucleotide having an unnatural base represented by Formula I or a derivative thereof as the base at an anticodon position and/or the messenger RNA containing a nucleotide having an unnatural base represented by Formula I or a derivative thereof may be prepared by chemical synthesis or transcription.

The ribosome used in the in vitro translation can be prepared by a method known to those skilled in the art.

Control of Thermodynamic Stability in Hybridization of Nucleic Acid

In another embodiment, the present invention provides a method of controlling thermodynamic stability in nucleic acid hybridization, the method comprising:

substituting a nucleotide in a nucleic acid strand by a nucleotide having an unnatural base represented by Formula I:

[Formula 30]

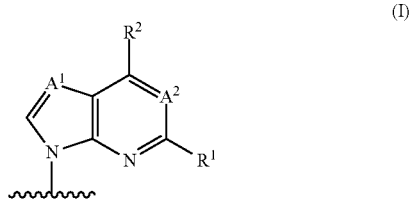

(I)

[wherein, $A^1$ and $A^2$ each independently represent N or CH;

$R^1$ represents hydrogen or an amino group; and $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group]

or a derivative thereof as the base.

The nucleic acid strand for controlling the thermodynamic stability in nucleic acid hybridization may be a probe, a primer, or an intramolecularly hybridizing single-stranded nucleic acid.

The present inventors have found that in a nucleic acid, the thermal stability of a double-stranded nucleic acid varies depending on the natural base pair adjacent to the unnatural base pair of the present invention and thereby that the thermal stability of a double-stranded nucleic acid can be controlled not to vary depending on the GC content in the double-stranded nucleic acid by introducing a nucleotide having an unnatural base represented by Formula I or a derivative thereof as the base into the nucleic acid.

Specifically, in a double-stranded nucleic acid having a nucleic acid strand containing a nucleotide having an unnatural base represented by Formula I or a derivative thereof as the base, the thermal stability is decreased depending on the natural base adjacent to the 5' side of unnatural base or its derivative in the order of C>T>G>A. Accordingly, for example, in order to considerably change the thermal stability of a double-stranded nucleic acid composed of natural bases, the base adjacent to the 3' side of a G or A base is replaced with an unnatural base represented by Formula I or a derivative thereof. In order to slightly change the thermal stability of a double-stranded nucleic acid composed of natural bases, the base adjacent to the 3' side of a C or T base is replaced with an unnatural base represented by Formula I or a derivative thereof.

Based on the above-described indices, thermal stability of a plurality of double-stranded nucleic acids can be controlled to be constant indepening of the GC content. Thus, the unnatural base represented by Formula I or the derivative thereof can control the thermal stability of a double-stranded nucleic acid, i.e., the Tm value, and is therefore useful in production of a probe for multiplex analysis involving simultaneous hybridization of a plurality of nucleic acid pairs.

The Tm value can be determined by a method known to those skilled in the art, for example, by calculation from a change in absorbance of a double-stranded nucleic acid.

Figure 9:
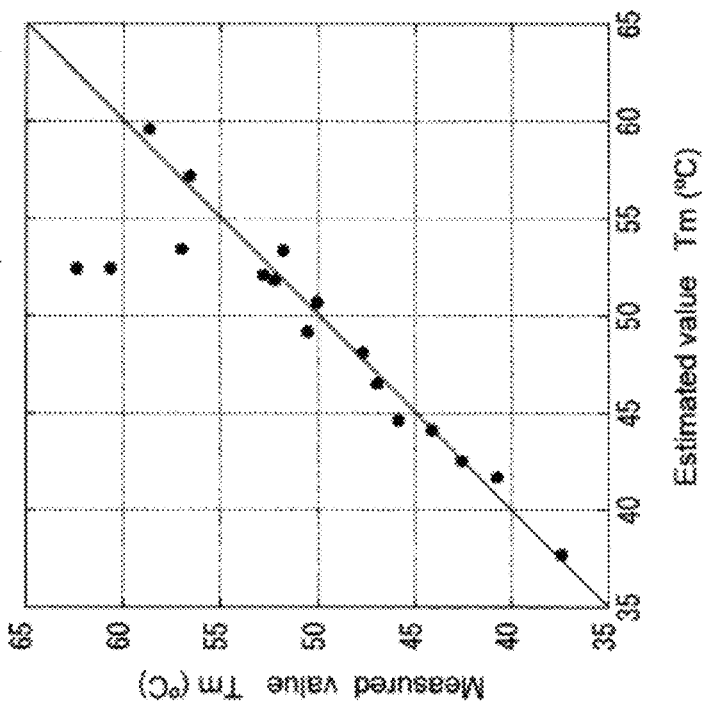
FIG. 9 is a graph of comparison between measured values and estimated values by the present invention of thermal stability of double-stranded DNAs containing a Ds-Ds base pair.

Incidentally, regarding Ds (7-(2-thienyl)imidazo[4,5-b]pyridin-3-yl group), as shown in FIG. 8, the present inventors calculated the free energy ΔG value necessary for estimating (estimation by Nearest-neighbor method) the Tm value of a double-stranded DNA containing Ds from the sequence thereof. The Tm values of double-stranded DNAs containing Ds estimated from calculated ΔG values show good correlation with experimental values (FIG. 9).

Accordingly, the Tm value of a double-stranded DNA containing Ds can be estimated from the ΔG value, and those skilled in the art can determine the position to which Ds is introduced in a nucleic acid in order to obtain a nucleic acid having a desired Tm value.

EXAMPLES

The present invention will be more specifically described by the following examples below, which are not intended to limit the technical scope of the present invention. Those skilled in the art can easily add modifications or changes to the present invention on the basis of the description of this specification, and such modifications and changes are included in the technical scope of the present invention.

Reagent, Solvent, and Other Components

Reagents and solvents were purchased from typical suppliers and were used without further purification. $^1$H-NMR (300 MHz, 270 MHz) and $^{31}$P-NMR (121 MHz) spectra were recorded on a BRUKER AV300 or JEOL nuclear magnetic resonance spectrometer. Synthesized nucleoside derivatives and nucleoside 5'-triphosphate were purified with a Gilson HPLC system using a fractionation column (Waters Microbond Sphere, C18, 19 mm×150 mm, flow rate: 10 mL/min) and a fractionation column (PEGASIL C8, Senshu Scientific Co., Ltd., 10 mm×150 mm, flow rate: 6 ml/min), respectively. Electrospray-ionization mass spectra (ESI-MS) were recorded on a Waters ZMD 4000 mass system equipped with a Waters 2690 LC system. Fluorescence spectra were measured with a JASCO FP6500 fluorescence spectrometer, and fluorescence quantum yields were determined using quinine sulfate as a standard.

Example 1

Synthesis of nucleoside and nucleotide having a 7-(2-thienyl)imidazo[4,5-b]pyridin-3-yl group (Ds) as the base A nucleoside and nucleotide having a 7-(2-thienyl)imidazo [4,5-b]pyridin-3-yl group (Ds) as the base, for example:

7-(2-thienyl)-3-(2-deoxy-β-D-ribofuranosyl)imidazo[4,5-b]pyridine (dDs);

7-(2-thienyl)-3-(β-D-ribofuranosyl)imidazo[4,5-b]pyridine (rDs);

7-(2-thienyl)-3-[2-deoxy-5-O-(4,4'-dimethoxytrityl)-β-D-ribofuranosyl]imidazo[4,5-b]pyridine 2-cyanoethyl-N,N-diisopropylaminophosphoramidite (phosphoramidite derivative of a deoxyribonucleoside having Ds as the base);

7-(2-thienyl)-3-(2-deoxy-β-D-ribofuranosyl)imidazo[4,5-b]pyridine 5'-triphosphate (dDsTP); and 7-(2-thienyl)-3-(β-D-ribofuranosyl)imidazo[4,5-b]pyridine 5'-triphosphate (rDsTP) were synthesized by a known method, for example, the method described in WO07/066,737.

Example 2

Synthesis of nucleoside; synthesis of 7-(2,2'-bithien-5-yl)-3-(2-deoxy-β-D-ribofuranosyl)imidazo[4,5-b]pyridine (dDss) and 7-(2,2',5',2''-terthien-5-yl)-3-(2-deoxy-β-D-ribofuranosyl)imidazo[4,5-b]pyridine (dDsss)

[Formula 31]

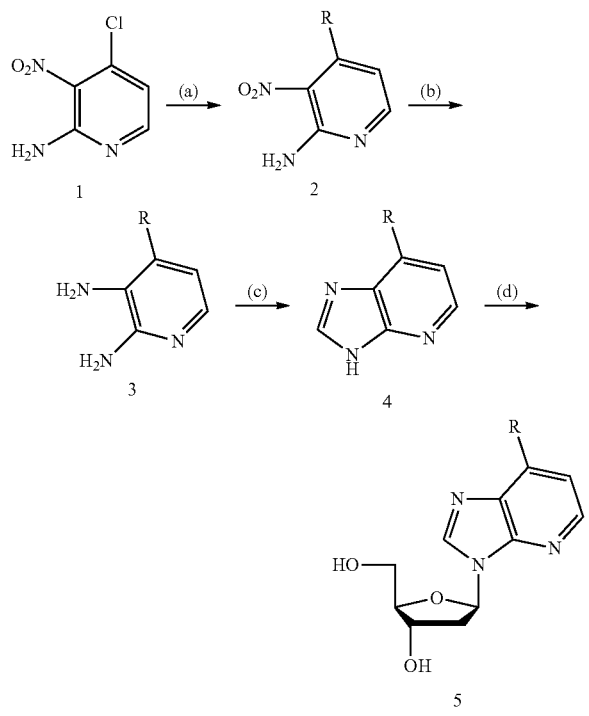

Conditions:
(a) 5-tributylstannyl-2,2'-bithiophene or 5-tributylstannyl-2,2',5',2''-terthiophene, Pd(PPh$_3$)$_2$Cl$_2$, and DMF;
(b) Pd/C, NaBH$_4$, pyridine, and H$_2$O;
(c) HCOOH; and
(d) NaH, 2-deoxy-3,5-di-O-p-toluoyl-α-D-erythro-pentofuranosyl chloride, and CH$_3$CN, and then NaOMe, MeOH, and CH$_2$Cl$_2$.
R represents a 2,2'-bithien-5-yl group or a 2,2',5',2''-terthien-5-yl group.

(2-1) Synthesis of 4-(2,2'-bithien-5-yl)-3-nitropyridine-2-amine and 4-(2,2',5',2''-terthien-5-yl)-3-nitropyridine-2-amine Normal-butyllithium (1.57 M solution in hexane: 3.2 mL, 5.0 mmol) was added to a solution of 2,2'-bithiophene (830 mg, 5.0 mmol) in THF (50 mL) at −78° C. This solution was stirred at −78° C. for 30 min, and then tributylstannyl chloride (1.5 mL) was added thereto. The reaction solution was stirred at room temperature for 30 min and was then separated between water and ethyl acetate. The organic layer was washed with saturated brine and dried over anhydrous sodium sulfate. The organic layer was concentrated and was then added to a solution of 2-amino-3-nitro-4-chloropyridine (519 mg, 3.0 mmol) and dichlorobis(triphenylphosphine)palladium (105 mg, 0.15 mmol) in DMF (18 mL). This solution was stirred at 100° C. for 5 hr and was then separated between ethyl acetate and water. The organic layer was washed with water, dried over anhydrous sodium sulfate, and concentrated under reduced pressure. 4-(2,2'-Bithien-5-yl)-3-nitropyridine-2-amine (809 mg, 89%) was obtained through purification by silica gel column chromatography (elution with a solution of 2% ethyl acetate in methylene chloride).

4-(2,2',5',2''-Terthiophen-5-yl)-3-nitropyridine-2-amine (250 mg, yield: 22%) was synthesized using 2,2',5',2''-terthiophene (1.24 g, 5.0 mmol) by the same reaction.

4-(2,2'-Bithien-5-yl)-3-nitropyridine-2-amine: $^1$H NMR (300 MHz, DMSO-d$_6$) δ 8.19 (d, 1H, J=5.1 Hz), 7.60 (dd, 1H, J=1.1, 5.1 Hz), 7.41 (dd, 1H, J=1.2, 3.6 Hz), 7.35 (d, 1H, J=3.8 Hz), 7.20 (d, 1H, J=3.9 Hz), 7.14 (dd, 1H, J=3.6, 5.1 Hz), 6.97 (bs, 1H), 6.80 (d, 1H, J=5.1 Hz). HRMS (FAB, 3-NBA matrix) for C$_{13}$H$_{10}$N$_3$O$_2$S$_2$, (M+H)$^+$ calculated value: 304.0214, observed value: 304.0172.

4-(2,2',5',2''-Terthien-5-yl)-3-nitropyridine-2-amine: $^1$H NMR (300 MHz, DMSO-d$_6$) δ 8.19 (d, 1H, J=5.0 Hz), 7.57 (dd, 1H, J=1.1, 5.1 Hz), 7.40 (m, 3H), 7.32 (d, 1H, J=3.8 Hz), 7.22 (d, 1H, J=3.9 Hz), 7.13 (dd, 1H, J=3.7, 5.1 Hz), 6.99 (bs, 2H), 6.80 (d, 1H, J=5.0 Hz).

(2-2) Synthesis of 4-(2,2'-bithien-5-yl)pyridine-2,3-diamine and 4-(2,2',5',2''-terthien-5-yl)pyridine-2,3-diamine One mole of NaBH$_4$ (7.5 mL) was added to a solution of 4-(2,2'-bithien-5-yl)-3-nitropyridine-2-amine (760 mg, 2.5 mmol) and palladium (10% carbon) in pyridine (25 mL) at 0° C. The solution was stirred at 0° C. for 30 min, and an aqueous 5% ammonium chloride solution was added thereto. The solution was stirred for 5 min and was then filtered. The filtrate was separated between methylene chloride and water, and the organic layer was dried over anhydrous sodium sulfate and concentrated. 4-(2,2'-Bithien-5-yl)pyridine-2,3-diamine (448 mg, 65%) was obtained through purification by silica gel column chromatography (elution with a solution of 5% methanol in methylene chloride).

4-(2,2',5',2''-Terthien-5-yl)pyridine-2,3-diamine (103 mg, yield: 45%) was synthesized using 4-(2,2',5',2''-terthien-5-yl)-3-nitropyridine-2-amine (250 mg, 0.65 mmol) by the same reaction.

4-(2,2'-Bithien-5-yl)pyridine-2,3-diamine: $^1$H NMR (300 MHz, DMSO-d$_6$) δ 7.54 (dd, 1H, J=7.54 Hz), 7.36-7.32 (m, 4H), 7.12 (dd, 1H, J=3.6, 5.1 Hz), 6.51 (d, 1H, J=5.3 Hz), 5.70 (bs, 2H), 4.77 (bs, 2H). HRMS (FAB, 3-NBA matrix) for C$_{13}$H$_{12}$N$_3$S$_2$, (M+H)$^+$ calculated value: 274.0473, observed value: 274.0470.

4-(2,2',5',2''-Terthien-5-yl)pyridine-2,3-diamine: NMR (300 MHz, DMSO-d$_6$) δ 7.55 (dd, 1H, J=1.1, 5.1 Hz), 7.39-7.29 (m, 6H), 7.12 (dd, 1H, J=3.6, 5.1 Hz), 6.52 (d, 1H, J=5.3 Hz), 5.71 (bs, 2H), 4.79 (bs, 2H).

(2-3) Synthesis of 7-(2,2'-bithien-5-yl)-3H-imidazo[4,5-b]pyridine and 7-(2,2',5',2''-terthien-5-yl)-3H-imidazo[4,5-b]pyridine A solution of 4-(2,2'-bithien-5-yl)pyridine-2,3-diamine (273 mg, 1.0 mmol) in formic acid (3.0 mL) was refluxed at 140° C. for 12 hr. The reaction solution was cooled to 0° C. and was then added to 28% aqueous ammonia (5.0 mL). This solution was separated between ethyl acetate and water, and the organic layer was washed with water, dried over anhydrous sodium sulfate, and dried under reduced pressure to yield 7-(2,2'-bithien-5-yl)-3H-imidazo[4,5-b]pyridine (272 mg, 96%).

7-(2,2',5',2"-Terthien-5-yl)-3H-imidazo[4,5-b]pyridine (106 mg, yield: 99%) was synthesized using 4-(2,2',5',2"-terthien-5-yl)pyridine-2,3-diamine (100 mg, 0.29 mmol) by the same reaction.

7-(2,2'-Bithien-5-yl)-3H-imidazo[4,5-b]pyridine: $^1$H NMR (300 MHz, DMSO-d$_6$) δ 13.25 (bs, 1H), 8.50 (s, 1H), 8.32 (s, 1H, J=5.2 Hz), 8.22 (d, 1H, J=3.9 Hz), 7.61 (d, 1H, J=5.0H), 7.59 (dd, 1H, J=5.0, 6.2 Hz), 7.47 (dd, 1H, J=1.1, 3.6 Hz), 7.45 (d, 1H, J=4.1 Hz), 7.15 (dd, 1H, J=3.6, 5.1 Hz). HRMS (FAB, 3-NBA matrix) for C$_{14}$H$_{10}$N$_3$S$_2$, (M+H)$^+$ calculated value: 284.0316, observed value: 284.0365.

7-(2,2',5',2"-Terthien-5-yl)-3H-imidazo[4,5-b]pyridine: $^1$H NMR (300 MHz, DMSO-d$_6$) δ 13.25 (bs, 1H), 8.51 (s, 1H), 8.33 (d, 1H, J=5.2 Hz), 8.23 (d, 1H, J=4.0 Hz), 7.62 (d, 1H, J=5.3H), 7.57 (dd, 1H, J=1.2, 5.1 Hz), 7.50 (d, 1H, J=3.9 Hz), 7.44 (d, 1H, J=3.8 Hz), 7.40 (dd, 1H, J=1.2, 3.6 Hz), 7.34 (d, 1H, J=3.8 Hz), 7.13 (dd, 1H, J=3.6, 5.1).

(2-4) Synthesis of 7-(2,2'-bithien-5-yl)-3-(2-deoxy-β-D-ribofuranosyl)imidazo[4,5-b]pyridine (dDss) and 7-(2,2',5',2"-terthien-5-yl)-3-(2-deoxy-β-D-ribofuranosyl)imidazo[4,5-b]pyridine (dDsss)

NaH (24 mg, 0.6 mmol, 60% dispersion in mineral oil) was added to a solution of 7-(2,2'-bithien-5-yl)-3H-imidazo[4,5-b]pyridine (142 mg, 0.5 mmol) in CH$_3$CN (10 mL). The reaction solution was stirred at room temperature for 30 min and then at 40° C. for 30 min, and 2-deoxy-3,5-di-O-p-toluoyl-α-D-erythro-pentofuranosyl chloride (233 mg, 0.6 mmol) was added thereto at room temperature. This reaction solution was stirred at room temperature for 12 hr and was separated between ethyl acetate and water. The organic layer was washed with saturated brine, dried over anhydrous sodium sulfate, and concentrated under reduced pressure. 7-(2,2'-Bithien-5-yl)-3-(2-deoxy-3,5-di-O-toluoyl-β-D-ribofuranosyl)imidazo[4,5-b]pyridine (227 mg, 0.36 mmol) was obtained through purification by silica gel column chromatography (elution with a solution of 2% methanol in methylene chloride). A solution of 28% NaOCH$_3$ in methanol (208 mg) was added to a solution of 7-(2,2'-bithien-5-yl)-3-(2-deoxy-3,5-di-O-toluoyl-β-D-ribofuranosyl)imidazo[4,5-b]pyridine (227 mg, 0.36 mmol) in methylene chloride (3.5 mL) and methanol (3.5 mL), followed by stirring at room temperature for 30 min. The reaction solution was separated between ethyl acetate and an aqueous saturated ammonium chloride solution, and the organic layer was washed with water, dried over anhydrous sodium sulfate, and concentrated under reduced pressure. 7-(2,2'-Bithien-5-yl)-3-(2-deoxy-β-D-ribofuranosyl)imidazo[4,5-b]pyridine (90 mg, 45%, second-stage yield) was obtained through purification by silica gel column chromatography (elution with a solution of 2% methanol in methylene chloride) and then by RP-HPLC.

7-(2,2',5',2"-Terthien-5-yl)-3-(2-deoxy-β-D-ribofuranosyl)imidazo[4,5-b]pyridine (22 mg, 17%, second-stage yield) was synthesized using 7-(2,2',5',2"-terthien-5-yl)-3H-imidazo[4,5-b]pyridine (100 mg, 0.27 mmol) by the same reaction (excepting that NaH was added and reflux was performed for 12 hr).

7-(2,2'-Bithien-5-yl)-3-(2-deoxy-β-D-ribofuranosyl)imidazo[4,5-b]pyridine: $^1$H NMR (300 MHz, DMSO-d$_6$) δ 8.77 (s, 1H), 8.35 (d, 1H, J=5.2 Hz), 8.23 (d, 1H, J=3.9 Hz), 7.68 (d, 1H, J=5.2 Hz), 7.60 (dd, 1H, J=1.0, 5.1 Hz), 7.48-7.45 (m, 2H), 7.15 (dd, 1H, J=3.7, 5.1 Hz), 6.54 (t, 1H, J=6.8 Hz), 5.34 (d, 1H, J=4.1 Hz), 5.11 (t, 1H, J=5.8 Hz), 4.47 (m, 1H), 3.92 (m, 1H), 3.69-3.52 (m, 2H), 2.81 (m, 1H), 2.36 (ddd, 1H, J=3.3, 6.2, 13.2 Hz). $^{13}$C NMR (75 MHz, DMSO-d$_6$) β 147.06, 144.01, 143.65, 140.02, 136.11, 135.50, 131.45, 130.82, 129.95, 128.56, 126.24, 124.74, 124.55, 113.51, 87.89, 83.77, 70.78, 61.71, 39.39. HRMS (FAB, 3-NBA matrix) for C$_{19}$H$_{18}$N$_3$O$_3$S$_2$, (M+H)$^+$ calculated value: 400.0790, observed value: 400.0815.

7-(2,2',5',2"-Terthien-5-yl)-3-(2-deoxy-β-D-ribofuranosyl)imidazo[4,5-b]pyridine: $^1$H NMR (300 MHz, DMSO-d$_6$) δ 8.77 (s, 1H), 8.36 (d, 1H, J=5.2 Hz), 8.24 (d, 1H, J=4.0 Hz), 7.70 (d, 1H, J=5, 2 Hz), 7.57 (dd, 1H, J=1,1, 5,1 Hz), 7.51 (d, 1H, J=3, 9 Hz), 7.45 (d, 1H, J=3.8 Hz), 7.40 (dd, 1H, J=1, 1, 3.6 Hz), 7.34 (d, 1H, J=3.8 Hz), 7.13 (dd, 1H, J=3.6, 5.1 Hz), 6.54 (t, 1H, J=6.8 Hz), 5.34 (d, 1H, J=2.4 Hz), 5.11 (t, 1H, J=5.3 Hz), 4.46 (m, 1H), 3.92 (m, 1H), 3.60 (m, 2H), 2.81 (m, 1H), 2.36 (ddd, 1H, J=3.3, 6.2, 13.2 Hz).

Example 3

Synthesis of nucleoside; synthesis of 2-amino-6-(2,2'-bithien-5-yl)-9-(2-deoxy-β-D-ribofuranosyl)purine (dss) and 2-amino-6-(2,2',5',2"-terthien-5-yl)-9-(2-deoxy-β-D-ribofuranosyl)purine (dsss)

[Formula 32]

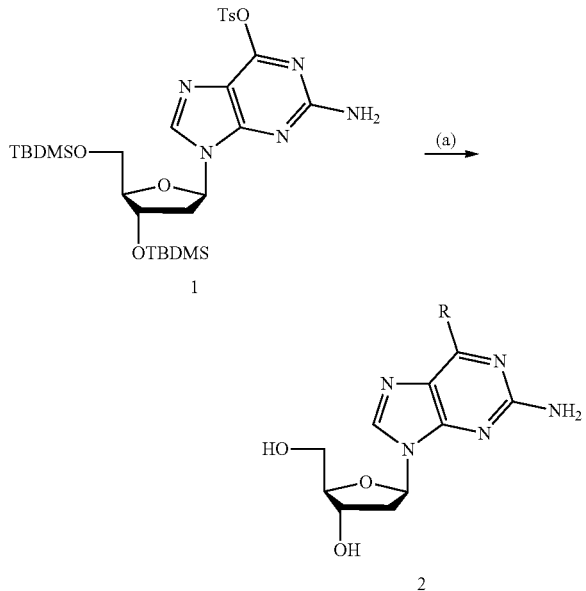

Conditions: (a) 5-tributylstannyl-2,2'-bithiophene or 5-tributylstannyl-2,2',5',2"-terthiophene, Pd(PPh$_3$)$_4$, LiCl, and dioxane, and then TBAF and THF. R represents a 2,2'-bithien-5-yl group or a 2,2',5',2"-terthien-5-yl group.

A solution of 6-O-tosyl-3',5'-di-O-tert-butyldimethylsilyl-deoxyguanosine (650 mg, 1.0 mmol), tetrakis(triphenylphosphine)palladium (58 mg, 0.05 mmol), lithium chloride (84 mg, 2.0 mmol), and 5-tributylstannyl-2,2'-bithiophene (5.0 mmol) in dioxane was refluxed at 120° C. for 4.5 hr. The reaction solution was separated between ethyl acetate and water, and the organic layer was washed with water, dried over anhydrous sodium sulfate, and concentrated under reduced pressure. 2-Amino-6-(2,2'-bithien-5-yl)-9-(2-deoxy-3,5-di-O-tert-butyldimethylsilyl-β-D-ribofuranosyl) purine (550 mg, 86%) was purified by silica gel column chromatography (elution with a solution of 1% methanol in methylene chloride). A solution of 1 M of tetrabutylammonium fluoride in THF (2.6 mL) was added to a solution of 2-amino-6-(2,2'-bithien-5-yl)-9-(2-deoxy-3,5-di-O-tert-butyldimethylsilyl-β-D-ribofuranosyl)purine (550 mg) in THF (8.6 mL), followed by stirring at room temperature for 1 hr. The reaction solution was concentrated, and then 2-amino-6-(2,2'-bithien-5-yl)-9-(2-deoxy-β-D-ribofuranosyl)purine (264 mg, 64%, second stage yield) was obtained through purification by silica gel column chromatography and RP-HPLC.

2-Amino-6-(2,2',5',2''-terthien-5-yl)-9-(2-deoxy-β-D-ribofuranosyl)purine (dsss) (405 mg, 81%, second stage yield) was synthesized using 5-tributylstannyl-2,2',5',2''-terthiophene (5.0 mmol) by the same reaction.

2-Amino-6-(2,2'-bithien-5-yl)-9-(2-deoxy-β-D-ribofuranosyl)purine (dss): $^1$H NMR (300 MHz, DMSO-$d_6$) δ 8.45 (d, 1H, J=3.9 Hz), 8.38 (s, 1H), 7.61 (dd, 1H, J=1.1, 5.1 Hz), 7.48-7.46 (m, 2H), 7.16 (dd, 1H, J=3.7, 5.1 Hz), 6.57 (bs, 2H), 6.29 (t, 1H, J=7.4 Hz), 5.30 (d, 1H, J=4.1 Hz), 4.98 (t, 1H, J=5.5 Hz), 4.40 (m, 1H), 3.85 (m, 1H), 3.58 (m, 2H), 2.66 (m, 1H), 2.28 (m, 1H).

2-Amino-6-(2,2',5',2''-terthien-5-yl)-9-(2-deoxy-β-D-ribofuranosyl)purine (dsss): $^1$H NMR (270 MHz, DMSO-$d_6$) δ 8.44 (d, 1H, J=4 Hz), 8.37 (s, 1H), 7.56 (dd, 1H, J=1.1, 4.9 Hz), 7.49 (d, 1H, J=4.0 Hz), 7.43 (d, 1H, J=4.0 Hz), 7.39 (dd, 1H, J=1.0, 3.6 Hz), 7.32 (d, 1H, J=4.0 Hz), 7.12 (dd, 1H, J=3.6, 4.9 Hz), 6.56 (bs, 2H), 6.28 (t, 1H, J=6.9 Hz), 5.29 (d, 1H, J=4.0 Hz), 4.96 (t, 1H, J=5.6 Hz), 4.38 (m, 1H), 3.85 (m, 1H), 3.55 (m, 2H), 2.65 (m, 1H), 2.28 (m, 1H).

Example 4

Synthesis of nucleoside; synthesis of 1-[2-deoxy-β-D-ribofuranosyl]-4-(2-thienyl)-pyrrolo[2,3-b]pyridine (dDsa), 1-[2-deoxy-β-D-ribofuranosyl]-4-(2-thiazolyl)-pyrrolo[2,3-b]pyridine (dDva), 1-[2-deoxy-β-D-ribofuranosyl]-4-(2-imidazolyl)-pyrrolo[2,3-b]pyridine (dDia), 1-[2-deoxy-β-D-ribofuranosyl]-4-(2,2'-bithien-5-yl)-pyrrolo[2,3-b]pyridine (dDsas), 1-[2-deoxy-β-D-ribofuranosyl]-4-[2-(2-thiazolyl)thien-5-yl]pyrrolo[2,3-b]pyridine (dDsav), and 1-[2-deoxy-β-D-ribofuranosyl]-4-[5-(2-thienyl)thiazol-2-yl]pyrrolo[2,3-b]pyridine (dDvas)

[Formula 33]

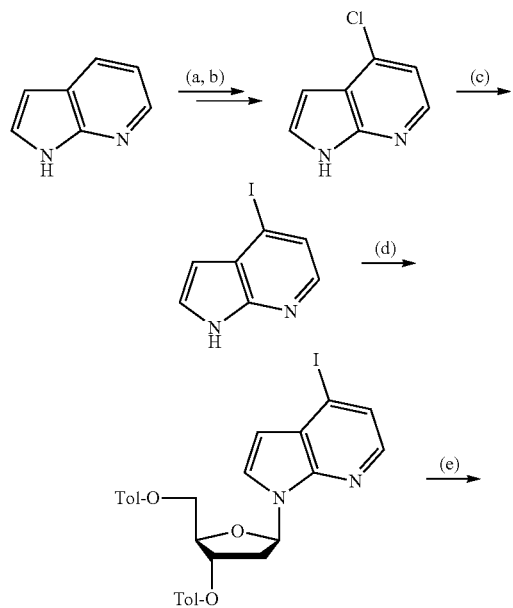

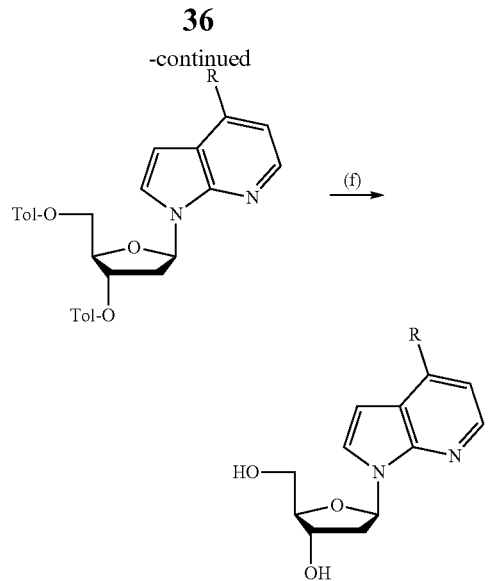

R represents a 2-thienyl group, a 2-thiazolyl group, a 2-imidazolyl group, a 2,2'-bithien-5-yl group, a 2-(2-thiazolyl)thien-5-yl group, or a 5-(2-thienyl)thiazol-2-yl group.

Reagents and Abbreviations:
(a) mCPBA, EtOAc, and then methanesulfonyl chloride and DMF;
(b) NaI, CH$_3$COCl, and CH$_3$CN;
(c) NaH, 2-deoxy-3,5-di-O-p-toluoyl-α-D-erythro-pentofuranosyl chloride, and CH$_3$CN;
(d) dichlorobis(triphenylphosphine)palladium, a tributylstannyl derivative, and DMF; and
(e) NH$_3$, methanol or NaOMe, and methanol.

(4-1) Synthesis of 4-iodo-1H-pyrrolo[2,3-b]pyridine

A solution of meta-chlorobenzoic acid (14 g, 54 mmol) in ethyl acetate (30 mL) was dropwise added to a solution of 1H-pyrrolo[2,3-b]pyridine (5.3 g, 45 mmol) in ethyl acetate (45 mL) over 1 hr with stirring at 0° C. After completion of the dropping, the mixture was stirred at room temperature for 3 hr, followed by leaving to stand at 0° C. The resulting crystals were collected by filtration, washed with ethyl acetate, and then dried under reduced pressure. The crystals were dissolved in water (30 mL), and then 30% K$_2$CO$_3$ was added until the pH of the solution reached 10. The solution was left to stand at room temperature for 1 hr and then at 0° C. for 1 hr. The resulting precipitate was collected by filtration and was washed with ether to yield 3.5 g (58%) of N-oxide. The N-oxide (3.0 g, 22 mmol) was dissolved in DMF (16 mL). The resulting solution was heated at 50° C., and a solution of methanesulfonyl chloride (4.7 mL, 60 mmol) in DMF (6.4 mL) was dropwise added to the solution at 70° C. This reaction solution was stirred at 75° C. for 2 hr. The reaction solution was added to ice and was neutralized with 10 N NaOH at 0° C., followed by stirring at room temperature for 1 hr. The resulting precipitate was collected by filtration, washed with water, and dried at 60° C. under reduced pressure to yield 2.7 g (80%) of the target 4-chloro-1H-pyrrolo[2,3-b]pyridine. 4-Chloro-1H-pyrrolo[2,3-b]pyridine (2.7 g, 18 mmol) and NaI (13 g, 88 mmol) were dissolved in acetonitrile (28 mL), and CH$_3$COCl (3.5 mL, 50 mmol) was added thereto with stirring at room temperature. The reaction solution was heated at 85° C. for 12 hr and then cooled to room temperature, and 10% Na$_2$CO$_3$ (28 mL) and 10% NaHSO$_3$ (28 mL) were added thereto, followed by stirring at room temperature for 15 min. Ethyl acetate was added thereto for separation, and the organic layer was washed with saturated brine. The organic layer was dried over anhydrous sodium sulfate, concentrated, and purified with a silica gel column to yield 4-iodo-1-N-acetyl-pyrrolo[2,3-b]pyridine (2.0 g) and 4-iodo-1H-pyrrolo[2,3-b]pyridine (2.3 g). 4-Iodo-1-N-acetyl-pyrrolo[2,3-b]pyridine (2.0 g, 7.0 mmol) was dissolved in ethanol (70 mL) and refluxed in methanol containing 28% sodium methoxide (1.4 mL, 7.0 mmol) for 1 hr. The reaction solution was concentrated and separated between ethyl acetate and an aqueous saturated ammonium chloride solution. The organic layer was washed with an aqueous saturated ammonium chloride solution, dried over anhydrous sodium sulfate, concentrated, and then combined with 4-iodo-1H-pyrrolo[2,3-b]pyridine (2.3 g) obtained above. The mixture was recrystallized from ethanol to yield 4-iodo-1H-pyrrolo[2,3-b]pyridine (4.0 g, 92%). 4-Iodo-1H-pyrrolo[2,3-b]pyridine: $^1$H NMR (500 MHz, DMSO-$d_6$) δ 12.01 (s, 1H), 7.89 (d, 1H, J=5.0 Hz), 7.59 (t, 1H, J=3.1 Hz), 7.51 (d, 1H, J=5.0 Hz), 6.27 (d, 1H, J=3.4 Hz).

(4-2) Synthesis of 1-[2-deoxy-3,5-di-O-(toluoyl)-β-D-ribofuranosyl]-4-iodo-pyrrolo[2,3-b]pyridine NaH (156 mg, 60% dispersion in oil, 3.9 mmol) was added to a solution of 4-iodo-1H-pyrrolo[2,3-b]pyridine (950 mg, 3.9 mmol) in acetonitrile (39 mL). The mixture was stirred at room temperature for 1 hr, and 2-deoxy-3,5-di-O-p-toluoyl-α-D-erythropentofuranosyl chloride (1.8 g, 1.2 equivalent) was added thereto, followed by stirring at room temperature for 1.5 hr. The reaction solution was separated between ethyl acetate and an aqueous saturated ammonium chloride solution. The organic layer was washed with an aqueous saturated ammonium chloride solution and saturated brine, dried over anhydrous sodium sulfate, concentrated, and purified with a silica gel column to yield 1.8 g (77%) of 1-[2-deoxy-3,5-di-O-(toluoyl)-β-D-ribofuranosyl]-4-iodo-pyrrolo[2,3-b]pyridine.

(4-3) Synthesis of 1-(2-deoxy-β-D-ribofuranosyl)-4-(2-thienyl)-pyrrolo[2,3-b]pyridine (dDsa) and 1-(2-deoxy-β-D-ribofuranosyl)-4-(2-thiazolyl)-pyrrolo[2,3-b]pyridine (dDva)

2-(Tributylstannyl)thiophene (601 μL, 1.8 mmol) was added to a solution of 1-[2-deoxy-3,5-di-O-(toluoyl)-β-D-ribofuranosyl]-4-iodo-pyrrolo[2,3-b]pyridine (715 mg, 1.2 mmol) and dichlorobis(triphenylphosphine)palladium (42 mg, 0.06 mmol) in DMF (12 mL), followed by stirring at 100° C. for 1 hr. The reaction solution was separated between ethyl acetate and water. The organic layer was washed with water and saturated brine, dried over anhydrous sodium sulfate, concentrated, and purified with a silica gel column to yield 586 mg (88%) of a toluoyl form. Methanolic ammonia (50 mL) was added to 1-(2-deoxy-β-D-ribofuranosyl)-4-(2-thienyl)-pyrrolo[2,3-b]pyridine (580 mg) to perform deprotection of the toluoyl group at room temperature for 12 hr. After purification with a silica gel column, HPLC was performed as final purification to yield 304 mg (91%) of 1-(2-deoxy-β-D-ribofuranosyl)-4-(2-thienyl)-pyrrolo[2,3-b]pyridine. dDva was synthesized as described above using 2-(tributylstannyl) thiazole to yield 1-(2-deoxy-3,5-di-O-(toluoyl)-β-D-ribofuranosyl)-4-(2-thiazolyl)-pyrrolo[2,3-b]pyridine (449 mg, 81%) and 1-(2-deoxy-β-D-ribofuranosyl)-4-(2-thiazolyl)-pyrrolo[2,3-b]pyridine (245 mg, 97%).

dDsa: NMR (300 MHz, DMSO-$d_6$) δ 8.27 (d, 1H, J=5.1 Hz), 7.87 (d, 1H, J=3.8 Hz), 7.83 (d, 1H, J=3.6 Hz), 7.79 (d, 1H, J=5.1 Hz), 7.41 (d, 1H, J=5.0 Hz), 7.28 (dd, 1H, J=3.7 and 5.0 Hz), 6.93 (d, 1H, J=3.8 Hz), 6.76 (dd, 1H, J=6.0 and 8.2 Hz), 5.28 (d, 1H, J=4.1 Hz), 5.02 (t, 1H, J=5.6 Hz), 4.39 (m, 1H), 3.85 (m, 1H), 3.56 (m, 2H), 2.57 (m, 1H), 2.26 (m, 1H).

dDva: NMR (300 MHz, DMSO-$d_6$) δ 8.38 (d, 1H, J=5.1 Hz), 8.13 (d, 1H, J=3.2 Hz), 8.01 (d, 1H, J=3.2 Hz), 7.96 (d, 1H, J=3.7 Hz), 7.72 (d, 1H, J=5.1 Hz), 7.15 (d, 1H, J=3.7 Hz), 6.79 (dd, 1H, J=6.1 and 8.0 Hz), 5.29 (d, 1H, J=4.0 Hz), 4.50 (t, 1H, J=5.5 Hz), 4.40 (m, 1H), 3.86 (m, 1H), 3.57 (m, 2H), 2.58 (m, 1H), 2.26 (m, 1H).

(4-4) Synthesis of 1-(2-deoxy-β-D-ribofuranosyl)-4-(2-imidazolyl)-pyrrolo[2,3-b]pyridine (dDia)

N-Dimethylaminosulfonyl-2-(tributylstannyl)imidazole (930 mg, 2.0 mmol) was added to a solution of 1-[2-deoxy-3,5-di-O-(toluoyl)-β-D-ribofuranosyl]-4-iodo-pyrrolo[2,3-b]pyridine (596 mg, 1.0 mmol), lithium chloride (42 mg, 1.0 mmol), and tetrakis(triphenylphosphine)palladium (58 mg, 0.05 mmol) in dioxane (10 mL), followed by stirring at 120° C. for 4 hr. The reaction solution was concentrated and was then purified with a silica gel column, and methanolic ammonia (30 mL) was added thereto. The resulting mixture was stirred at room temperature for 24 hr. The reaction solution was concentrated and purified with a silica gel column and then with HPLC to yield 218 mg (54%, second stage yield) of 1-(2-deoxy-β-D-ribofuranosyl)-4-(N-dimethylaminosulfonyl-2-imidazolyl)-pyrrolo[2,3-b]pyridine. 1-(2-Deoxy-β-D-ribofuranosyl)-4-(N-dimethylaminosulfonyl-2-imidazolyl)-pyrrolo[2,3-b]pyridine (200 mg, 0.49 mmol) was dissolved in 80% acetic acid, followed by stirring at 60° C. for 3 hr. The reaction solution was concentrated, and aqueous ammonia was added thereto for further concentration. Subsequently, 1-(2-deoxy-β-D-ribofuranosyl)-4-(2-imidazolyl)-pyrrolo[2,3-b]pyridine (dDia: 109 mg, 74%) was obtained through purification by HPLC.

dDia: $^1$H NMR (300 MHz, DMSO-$d_6$) δ 12.81 (s, 1H), 8.30 (d, 1H, J=5.1 Hz), 7.79 (d, 1H, J=3.7 Hz), 7.60 (d, 1H, J=5.1 Hz), 7.39 (s, 1H), 7.30 (d, 1H, J=3.7 Hz), 7.22 (s, 1H), 7.74 (dd, 1H, J=5.9 Hz), 5.27 (d, 1H, J=4.1 Hz), 5.03 (t, 1H, J=5.6 Hz), 4.38 (m, 1H), 3.84 (m, 1H), 3.57 (m, 2H), 2.55 (m, 1H), 2.22 (m, 1H).

(4-5) Synthesis of 1-[2-deoxy-β-D-ribofuranosyl]-4-(2,2'-bithien-5-yl)-pyrrolo[2,3-b]pyridine (dDsas)

A solution of 2-tributylstannyl-5,2-bithiophene (0.3 mmol), 1-[2-deoxy-3,5-di-O-(toluoyl)-β-D-ribofuranosyl]-4-iodo-pyrrolo[2,3-b]pyridine (120 mg, 0.2 mmol), and dichlorobistriphenylphosphine palladium (7 mg) in DMF (2 mL) was stirred at 100° C. for 1 hr. The reaction solution was separated between ethyl acetate and water, and the organic layer was washed with saturated brine, dried over anhydrous sodium sulfate, concentrated, and purified with a silica gel column to yield 1-[2-deoxy-3,5-di-O-(toluoyl)-β-D-ribofuranosyl]-4-(2,2'-bithien-5-yl)-pyrrolo[2,3-b]pyridine. This was dissolved in methylene chloride (10 mL) and methanol (2 mL), and 28% sodium methylate (0.12 mL) was added thereto, followed by stirring at room temperature for 30 min. 1-[2-Deoxy-β-D-ribofuranosyl]-4-(2,2'-bithien-5-yl)-pyrrolo[2,3-b]pyridine (dDsas, 54 mg, 68%) was obtained by purification with a silica gel column and by HPLC.

$^1$H NMR (300 MHz, DMSO-$d_6$) δ 8.26 (d, 1H, J=5.1 Hz), 7.88 (d, 1H, J=3.8 Hz), 7.80 (d, 1H, J=3.9 Hz), 7.58 (dd, 1H, J=1.1, 5.1 Hz), 7.44 (m, 3H), 7.14 (dd, 1H, J=3.7, 5.1 Hz), 6.96 (d, 1H, J=3.8 Hz), 6.75 (dd, 1H, J=6.1, 8.1 Hz), 5.26 (d, 1H, J=4.1 Hz), 5.00 (t, 1H, J=5.6 Hz), 4.39 (m, 1H), 3.84 (m, 1H), 3.56 (m, 2H), 2.59 (m, 1H), 2.23 (m, 1H).

(4-6) Synthesis of 1-[2-deoxy-β-D-ribofuranosyl]-4-[2-(2-thiazolyl)thien-5-yl]pyrrolo[2,3-b]pyridine (dDsav)

2-Tributylstannylthiophene (3.5 mL, 11 mmol) was added to a solution of 2-bromothiazole (0.9 mL, 10 mmol) and dichlorobistriphenylphosphine palladium (350 mg) in DMF (50 mL), followed by stirring at 90° C. for 3 hr. The reaction solution was concentrated and was separated between ethyl acetate and water. The organic layer was washed with saturated brine and dried over anhydrous sodium sulfate. The organic layer was concentrated and then purified with a silica gel column to yield 2,2'-thienylthiazole (1.4 g, 87%). A solution of 2,2'-thienylthiazole (251 mg, 1.5 mmol) in THF (15 mL) was cooled to −78° C., and n-butyllithium (0.96 mL, 1.5 mmol, 1.57 M solution in hexane) was added thereto, followed by stirring at −78° C. for 30 min. Trimethylsilyl chloride (1.5 mmol, 0.19 mL) was added thereto, followed by stirring at −78° C. for 30 min. Furthermore, n-butyllithium (0.96 mL, 1.5 mmol, 1.57 M solution in hexane) was added thereto, followed by stirring at −78° C. for 30 min, and then tributylstannyl chloride (0.45 mL, 1.6 mmol) was added thereto, followed by stirring at room temperature for 30 min. The reaction solution was separated between ethyl acetate and water, and the organic layer was washed with saturated brine, dried over anhydrous sodium sulfate, concentrated, and purified with a silica gel column to yield 2-tributylstannyl-5-(5'-trimethylsilyl-2-thienyl)thiophene (735 mg). 2-Tributylstannyl-5-(5'-trimethylsilyl-2-thienyl)thiophene (397 mg, 0.75 mmol) was added to a solution of 1-[2-deoxy-3,5-di-O-(toluoyl)-β-D-ribofuranosyl]-4-iodo-pyrrolo[2,3-b]pyridine (298 mg, 0.5 mmol) and dichlorobistriphenylphosphine palladium (18 mg, 0.025 mmol) in DMF (5 mL), followed by stirring at 100° C. for 1 hr. The reaction solution was separated between ethyl acetate and water, and the organic layer was washed with saturated brine, dried over anhydrous sodium sulfate, concentrated, and purified with a silica gel column to yield 1-[2-deoxy-3,5-di-O-(toluoyl)-β-D-ribofuranosyl]-4-(2-(5-(5'-trimethylsilyl-2-thienyl)thiophene)-pyrrolo[2,3-b]pyridine (335 mg). This was dissolved in methylene chloride (5 mL) and methanol (5 mL), and 28% sodium methylate (290 mg, 1.5 mmol) was added thereto, followed by stirring at room temperature for 30 min. Ammonium chloride (80 mg) was added to the reaction solution. After concentration, 1-[2-deoxy-β-D-ribofuranosyl]-4-[2-(2-thiazolyl)thien-5-yl]-pyrrolo[2,3-b]pyridine (dDsav, 112 mg) and 1-[2-deoxy-β-D-ribofuranosyl]-4-[2-(2-thienyl)thiazol-5-yl]pyrrolo[2,3-b]pyridine (dDv' as, 26 mg) were obtained by purification with a silica gel column and by HPLC.

dDsav: $^1$H NMR (300 MHz, DMSO-$d_6$) δ 8.30 (d, 1H, J=5.1 Hz), 7.91 (d, 1H, J=3.8 Hz), 7.87 (m; 2H), 7.79 (m, 2H), 7.48 (d, 1H, J=5.1 Hz), 6.96 (d, 1H, J=3.8 Hz), 6.76 (dd, 1H, 6.1, 8.0 Hz), 5.27 (d, 1H, J=4.1 Hz), 4.99 (t, 1H, J=5.6 Hz), 4.38 (m, 1H), 3.85 (m, 1H), 3.56 (m, 2H), 2.56 (m, 1H), 2.24 (m, 1H).

dDv' as: $^1$H NMR (300 MHz, DMSO-$d_6$) δ 8.51 (s, 1H), 8.30 (d, 1H, J=5.1 Hz), 7.93 (d, 1H, J=3.8 Hz), 7.79 (m, 2H), 7.47 (d, 1H, J=5.1 Hz), 7.22 (dd, 1H, J=4.0, 4.9 Hz), 7.94 (d, 1H, J=3.8 Hz), 6.75 (dd, 1H, J=6.2, 7.9 Hz), 5.27 (d, 1H, J=4.1 Hz), 4.99 (t, 1H, J=5.6 Hz), 3.38 (m, 1H), 3.59 (m, 2H), 2.57 (m, 1H), 2.24 (m, 1H).

(4-7) Synthesis of 1-[2-deoxy-β-D-ribofuranosyl]-4-[5-(2-thienyl)thiazol-2-yl]pyrrolo[2,3-b]pyridine (dDvas)

A solution of 5-(2-thienyl)thiazole (0.4 mmol) in diethyl ether was cooled to −78° C., and n-butyllithium (0.4 mmol, 1.57 M solution in hexane) was added thereto, followed by stirring at −78° C. for 30 min. Furthermore, tributylstannyl chloride was added thereto, followed by stirring at room temperature for 30 min. The reaction solution was separated between ethyl acetate and water. The organic layer was washed with saturated brine and concentrated, and 1-[2-deoxy-3,5-di-O-(toluoyl)-β-D-ribofuranosyl]-4-iodo-pyrrolo[2,3-b]pyridine (120 mg, 0.2 mmol), chlorobistriphenylphosphine palladium (5% mol), and DMF (2 mL) were added thereto, followed by stirring at 100° C. for 1 hr. The reaction solution was separated between ethyl acetate and water, and the organic layer was washed with saturated brine and water, dried over anhydrous sodium sulfate, and concentrated. After purification with a silica gel column and addition of sodium methoxide (1.6 mL), the resulting mixture was stirred at room temperature for 30 min. dDvas nucleoside (34 mg) was purified with a silica gel column and by HPLC.

dDvas: $^1$H NMR (300 MHz, DMSO-$d_6$) δ 8.37 (d, 1H, J=5.1 Hz), 8.31 (s, 1H), 7.96 (d, 1H, J=3.8 Hz), 7.68 (m, 2H), 7.54 (dd, 1H, J=1.1, 3.6 Hz), 7.19 (dd, 1H, 3.7, 5.1 Hz), 7.15 (d, 1H, J=3.7 Hz), 6.77 (dd, 1H, J=6.1, 8.0 Hz), 5.28 (d, 1H, J=4.1 Hz), 4.98 (t, 1H, J=5.5 Hz), 4.38 (m, 1H), 3.85 (m, 1H), 3.56 (m, 2H), 2.57 (m, 1H), 2.49 (m, 1H).

Example 5

Amidite Synthesis (dDss and dss)

[Formula 34]

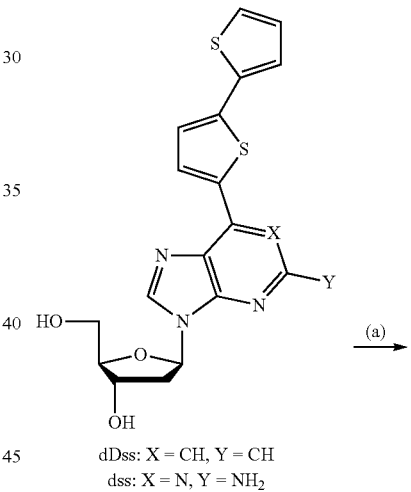

dDss: X = CH, Y = CH
dss: X = N, Y = NH$_2$

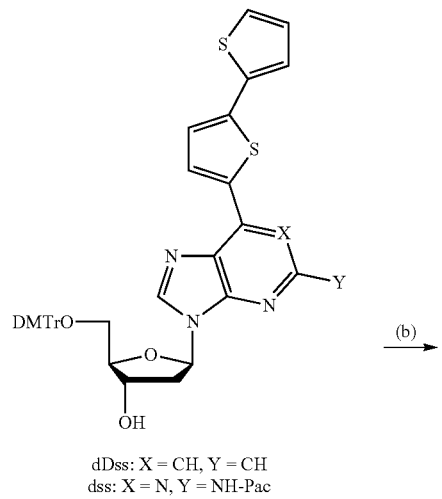

dDss: X = CH, Y = CH
dss: X = N, Y = NH-Pac

-continued

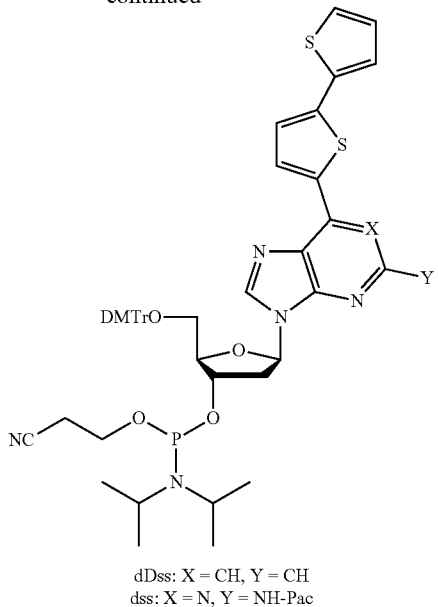

dDss: X = CH, Y = CH
dss: X = N, Y = NH-Pac

Conditions:
(a) DMTr-Cl, pyridine for dDss, trimethylsilyl chloride, phenoxyacetyl chloride, hydroxybenzotriazole, pyridine, and $CH_3CN$, and then DMTr-Cl and pyridine
(b) 2-cyanoethyl N,N-diisopropylaminochlorophosphoramidite, diisopropylamine, and THF.

(5-1) Synthesis of 7-(2,2'-bithien-5-yl)-3-(2-deoxy-5-O-(4,4'-dimethoxytrityl)-β-D-ribofuranosyl)imidazo[4,5-b]pyridine 7-(2,2'-Bithien-5-yl)-3-(2-deoxy-β-D-ribofuranosyl)imidazo[4,5-b]pyridine (dDss) (262 mg, 0.66 mmol) was azeotropically dried with pyridine three times and was then dissolved in pyridine (7.0 mL), and 4,4'-dimethoxytrityl chloride (367 mg, 0.79 mmol) was added thereto. The resulting mixture was stirred at room temperature for 1 hr and was then separated between ethyl acetate and an aqueous 5% sodium hydrogen carbonate solution. The organic layer was washed with saturated brine, dried over anhydrous sodium sulfate, and then concentrated under reduced pressure. 7-(2,2'-Bithien-5-yl)-3-(2-deoxy-5-O-(4,4'-dimethoxytrityl)-β-D-ribofuranosyl)imidazo[4,5-b]pyridine (408 mg, 89%) was obtained through purification by silica gel column chromatography (elution with a solution of 1% methanol in methylene chloride).

$^1$H NMR (300 MHz, DMSO-$d_6$) δ 8.66 (s, 1H), 8.30 (d, 1H, J=5.2 Hz), 8.22 (d, 1H, J=3.9 hz), 7.67 (d, 1H, J=5.2 Hz), 7.60 (dd, 1H, J=1.1, 5.1 Hz), 7.48-7.46 (m, 2H), 7.34-7.31 (m, 2H), 7.24-7.14 (m, 8H), 6.80 (d, 2H, J=9.0 Hz), 6.75 (d, 2H, J=9.0 Hz), 6.55 (t, 1H, J=6.3 Hz), 5.39 (d, 1H, J=4.6 Hz), 4.51 (m, 1H), 3.70 and 3.67 (s, s, 6H), 3.19 (m, 2H), 2.96 (m, 1H), 2.41 (m, 1H).

HRMS (FAB, 3-NBA matrix) for $C_{40}H_{35}N_3O_5S_2Na$, (M+Na)$^+$ calculated value: 724.1916, observed value: 724.1978.

(5-2) Synthesis of 7-(2,2'-bithien-5-yl)-3-(2-deoxy-5-O-(4,4'-dimethoxytrityl)-β-D-ribofuranosyl)imidazo[4,5-b]pyridine 2-cyanoethyl-N,N-diisopropylaminophosphoramidite 7-(2,2'-Bithien-5-yl)-3-(2-deoxy-5-O-(4,4'-dimethoxytrityl)-β-D-ribofuranosyl)imidazo[4,5-b]pyridine (203 mg, 0.29 mmol) was azeotropically dried with pyridine three times and with THF three times. To this, diisopropylethylamine (76 μL, 0.43 mmol) and THF (1.5 mL) were added, and 2-cyanoethyl-N,N-diisopropylaminochlorophosphoramidite (78 μL, 0.35 mmol) was lastly added. The resulting mixture was stirred at room temperature for 1 hr. Methanol (50 μL) was added to the reaction solution, and the resulting mixture was diluted with EtOAc:TEA (20:1, v/v, 20 mL), washed with an aqueous 5% sodium hydrogen carbonate solution and saturated brine, and then dried over anhydrous sodium sulfate. The organic layer was concentrated under reduced pressure. 7-(2,2'-Bithien-5-yl)-3-(2-deoxy-5-O-(4,4'-dimethoxytrityl)-β-D-ribofuranosyl)imidazo[4,5-b] pyridine 2-cyanoethyl-N,N-diisopropylaminophosphoramidite (260 mg, 99%) was obtained through purification by silica gel column chromatography (elution with a solution of methylene chloride containing 2% triethylamine:hexane (2:3)).

$^1$H NMR (300 MHz, CDCl$_3$) δ 8.33-8.30 (m, 2H), 8.11 (d, 1H, J=3.9 Hz), 7.47-7.41 (m, 3H), 7.35-7.17 (m, 10H), 7.07 (dd, 1H, J=3.6, 5.1 Hz), 6.82-6.76 (m, 4H), 6.62 (m, 1H), 4.80 (m, 1H), 4.34 (m, 1H), 3.91-3.78 (m, 10H), 3.49-3.32 (m, 2H), 2.94 (m, 1H), 2.73 (m, 1H), 2.64 (t, 1H, J=6.5 Hz), 2.48 (t, 1H, J=6.4 Hz), 1.23-1.12 (m, 12H).

$^{31}$P NMR (121 MHz, CDCl$_3$) δ 149.47 and 149.29 (diastereoisomer).

HRMS (FAB, 3-NBA matrix) for $C_{49}H_{52}N_5O_6S_2PNa$ (M+Na)$^+$ calculated value: 924.2994, observed value: 924.3328.

(5-3) Synthesis of 2-phenoxyacetylamino-6-(2,2'-bithien-5-yl)-9-(2-deoxy-β-D-ribofuranosyl)purine 2-Amino-6-(2,2'-bithien-5-yl)-9-(2-deoxy-β-D-ribofuranosyl)purine (ss) (208 mg, 0.5 mmol) was azeotroped with pyridine three times and was dissolved in pyridine (2.5 mL), and trimethylsilyl chloride (476 μL, 3.8 mmol) was added thereto, followed by stirring at room temperature for 30 min (solution A). 1-Hydrorxybenzotriazole (122 mg, 0.9 mmol) was azeotroped with pyridine three times and was then dissolved in pyridine (0.25 mL) and acetonitrile (0.25 mL). The resulting solution was cooled to 0° C., and phenoxyacetyl chloride (104 μL, 0.75 mmol) was added thereto, followed by stirring for 5 min (solution B). Solution A was added to solution B at 0° C., and the mixture was stirred at room temperature for 12 hr. The reaction solution was cooled to 0° C., and 14% aqueous ammonia (0.5 mL) was added thereto, followed by stirring for 10 min. The reaction solution was separated between ethyl acetate and water, and the organic layer was dried over anhydrous sodium sulfate and was then concentrated. 2-Phenoxyacetylamino-6-(2,2'-bithien-5-yl)-9-(2-deoxy-β-D-ribofuranosyl)purine (246 mg, 89%) was obtained through purification by silica gel column chromatography (elution with a solution of 5% methanol in methylene chloride).

$^1$H NMR (300 MHz, DMSO) δ 10.77 (s, 1H), 8.74 (s, 1H), 8.55 (d, 1H, J=4.0 Hz), 7.65 (dd, 1H, J=1.1, 5.1 Hz), 7.54 (d, 1H, J=3.9 Hz), 7.51 (dd, 1H, J=1.1, 3.6 Hz), 7.34-7.29 (m, 2H), 7.17 (dd, 1H, J=5.7, 5.1 Hz), 7.01-6.94 (m, 3H), 6.41 (t, 1H, J=6.8 Hz), 5.35 (d, 1H, J=4.1 Hz), 5.10 (s, 2H), 4.93 (t, 1H, J=5.5 Hz), 4.46 (m, 1H), 3.89 (m, 1H), 3.59 (m, 2H), 2.79 (m; 1H), 2.35 (m, 1H).

(5-4) Synthesis of 2-phenoxyacetylamino-6-(2,2'-bithien-5-yl)-9-(2-deoxy-5-O-dimethoxytrityl-β-D-ribofuranosyl) purine 2-Phenoxyacetylamino-6-(2,2'-bithien-5-yl)-9-(2-deoxy-β-D-ribofuranosyl)purine (240 mg, 0.44 mmol) was azeotropically dried with pyridine and was then dissolved in pyridine (4.4 mL), and 4,4'-dimethoxytrityl chloride (163 mg, 0.48 mmol) was added thereto. The resulting mixture was stirred at room temperature for 1 hr and was then separated between ethyl acetate and an aqueous 5% sodium hydrogen carbonate solution. The organic layer was washed with saturated brine, dried over anhydrous sodium sulfate, and then concentrated under reduced pressure. 2-Phenoxyacetylamino-6-(2,2'-bithien-5-yl)-9-(2-deoxy-5-O-dimethoxytrityl-β-D-ribofuranosyl)purine (314 mg, 84%) was obtained through purification by silica gel column chromatography (elution with a solution of 5% methanol in methylene chloride).

¹H NMR (300 MHz, DMSO) δ 10.72 (s, 1H), 8.64 (s, 1H), 8.56 (d, 1H, J=4.0 Hz), 7.65 (dd, 1H, J=1.1, 5.1 Hz), 7.55 (d, 1H, J=3.9 Hz), 7.52 (dd, 1H, J=1.1, 3.6 Hz), 7.34-7.27 (m, 4H), 7.19-7.12 (m, 8H), 7.00-6.95 (m, 3H), 6.75 (d, 2H, J=8.9 Hz), 6.69 (d, 2H, J=8.9 Hz), 6.45 (t, 1H, J=5.8 Hz), 5.33 (d, 1H, J=4.7 Hz), 5.05 (m, 2H), 4.55 (m, 1H), 4.01 (m, 1H), 3.67, 3.64 (s, s, 6H), 3.30 (m, 1H, overlapping with H₂O signal peak), 3.12 (m, 1H), 2.95 (m, 1H), 2.40 (m, 1H).

(5-5) Synthesis of 2-phenoxyacetylamino-6-(2,2'-bithien-5-yl)-9-(2-deoxy-5-β-dimethoxytrityl-β-D-ribofuranosyl)purine 2-cyanoethyl-N,N-diisopropylaminophosphoramidite 2-Phenoxyacetylamino-6-(2,2'-bithien-5-yl)-9-(2-deoxy-5-O-dimethoxytrityl-β-D-ribofuranosyl)purine (310 mg, 0.36 mmol) was azeotropically dried with pyridine three times and with THF three times. To this, diisopropylethylamine (95 μL, 0.55 mmol) and THF (1.8 mL) were added, and 2-cyanoethyl-N,N-diisopropylaminochlorophosphoramidite (98 μL, 0.44 mmol) was then added. The mixture was stirred at room temperature for 1 hr. Methanol (50 μL) was added to the reaction solution, and the resulting mixture was diluted with EtOAc:TEA (20:1, v/v, 20 mL), washed with an aqueous 5% sodium hydrogen carbonate solution and saturated brine, and then dried over anhydrous sodium sulfate. The organic layer was concentrated under reduced pressure. 2-Phenoxyacetylamino-6-(2,2'-bithien-5-yl)-9-(2-deoxy-5-O-dimethoxytrityl-β-D-ribofuranosyl)purine 2-cyanoethyl-N,N-diisopropylaminophosphoramidite (370 mg, 97%) was obtained through purification by silica gel column chromatography (elution with a solution of methylene chloride containing 2% triethylamine:hexane (2:3)).

¹H NMR (300 MHz, CDCl₃) δ 8.59, 8.58 (s, s, 1H), 8.22 (d, 1H, J=4.4 Hz), 7.39-7.17 (m, 14H), 7.13-7.05 (m, 4H), 6.82-6.75 (m, 4H), 6.50 (t, 1H, J=6.6 Hz), 4.94 (bs, 2H), 4.80 (m, 1H), 4.34 (m, 1H), 3.94-3.55 (m, 4H), 3.77 (s, 6H), 3.45-3.40 (m, 2H), 2.93 (m, 1H), 2.80-2.66 (m, 1H), 2.65 (t, 1H, J=6.4 Hz), 2.48 (t, 1H, J=6.4 Hz), 1.22-1.11 (m, 12H).

³¹P NMR (121 MHz, CDCl₃) δ 149.57.

Example 6

Synthesis of Amidites of Azaindole Nucleosides (dDsa, dDva, and dDia)

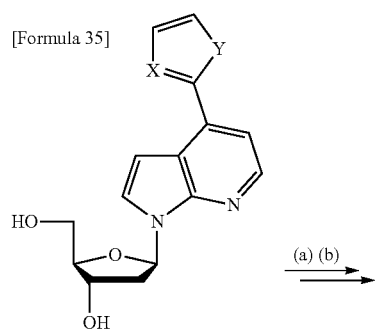

[Formula 35]

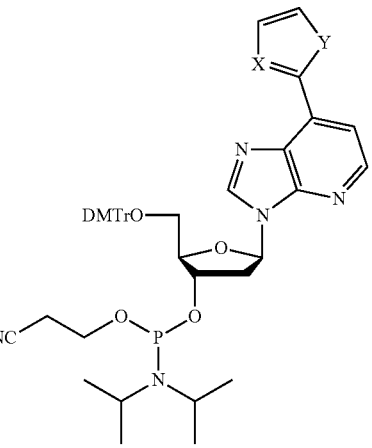

dDsa amidite: X=CH, Y=S
dDva amidite: X=N, Y=S
dDia amidite: X=N, Y=NH dDsa (300 mg, 0.9 mmol) was azeotropically dried with pyridine three times and was dissolved in pyridine (9.0 mL), and 4,4'-dimethoxytrityl chloride (386 mg, 1.1 mmol) was added thereto, followed by stirring at room temperature for 1 hr. The reaction solution was separated between ethyl acetate and an aqueous 5% sodium hydrogen carbonate solution. The organic layer was washed with saturated brine, dried over anhydrous sodium sulfate, and then concentrated under reduced pressure. The dimethoxytrityl form of dDsa (570 mg, 97%) was obtained through purification by silica gel column chromatography (elution with a solution of 20% ethyl acetate in methylene chloride). The dimethoxytrityl form of dDva (424 mg, 99%) and the dimethoxytrityl form of dDia (200 mg, 95%) were obtained by the same method.

The dimethoxytrityl form of dDsa (290 mg, 0.47 mmol) was azeotropically dried with pyridine three times and with THF three times. To this, diisopropylethylamine (123 μL, 0.7 mmol) and THF (2.4 mL) were added, and 2-cyanoethyl-N,N-diisopropylaminochlorophosphoramidite (115 μL, 0.52 mmol) was then added. The resulting mixture was stirred at room temperature for 1 hr. Methanol (50 μL) was added to the reaction solution, and the mixture was diluted with EtOAc:TEA (20:1, v/v, 20 mL), washed with an aqueous 5% sodium hydrogen carbonate solution and saturated brine, and then dried over anhydrous sodium sulfate. The organic layer was concentrated under reduced pressure. The phosphoramidite form of dDsa (dDsa amidite: 345 mg, 90%) was obtained through purification by silica gel column chromatography (elution with a solution of methylene chloride containing 2% triethylamine:hexane (2:3)). The dDva amidite (227 mg, 86%) and the dDia amidite (125 mg, 93%) were synthesized by the same method.

dDsa amidite: ¹H NMR (300 MHz, DMSO-d₆) δ 8.26 (d, 1H, J=5.1 Hz), 7.83 (d, 1H, J=3.6 Hz), 7.79 (d, 1H, J=5.1 Hz), 7.72 (d, 1H, J=3.8 Hz), 7.43 (d, 1H, J=5.1 Hz), 7.37 (m, 2H), 7.29-7.18 (m, 8H), 6.93 (d, 1H, J=3.6 Hz), 6.85-6.79 (m, 4H), 7.75 (t, 1H, J=7.0 Hz), 4.69 (m, 1H), 4.13-4.06 (m, 1H), 3.82-3.59 (m, 10H), 3.31-3.16 (m, 2H), 2.83 (m, 1H), 2.78 (t, 1H, J=5.9 Hz), 2.68 (t, 1H, J=5.9 Hz), 1.17-1.04 (m, 12H). ³¹P NMR (121 MHz, DMSO-d₆) δ 148.82, 148.21.

dDva amidite: ¹H NMR (300 MHz, DMSO-d₆) δ 8.36 (d, 1H, J=5.1 Hz), 8.13 (d, 1H, J=3.2 Hz), 8.01 (d, 1H, J=3.2 Hz), 7.81 (d, 1H, J=3.7 Hz), 7.73 (d, 1H, J=5.0 Hz), 7.37 (m, 1H), 7.29-7.19 (m, 7H), 7.14 (d, 1H, J=3.7 Hz), 6.85-6.75 (m, 5H), 4.70 (m, 1H), 4.13-4.07 (m, 1H), 3.82-3.52 (m, 10H), 3.31-3.15 (m, 2H), 2.85 (m, 1H), 2.78 (t, 1H, J=5.9 Hz), 2.69 (t, 1H, J=5.9 Hz), 2.49 (m, 1H), 1.17-1.06 (m, 12H). ³¹P NMR (121 MHz, DMSO-d₆) δ 148.85, 148.22.

dDia amidite: ¹H NMR (270 MHz, CDCl₃) δ 9.79 (bs, 1H), 8.34 (m, 1H), 7.56-7.20 (m, 12H), 6.98 (m, 1H), 6.87 (m, 1H), 6.76 (m, 4H), 4.75 (m, 1H), 4.24 (m, 1H), 3.84-3.40 (m, 13H), 2.71 (m, 1H), 2.60 (t, 1H, J=6.6 Hz), 2.44 (t, 1H, J=6.6 Hz) 1.19-1.07 (m, 12H). ³¹P NMR (109 MHz, CDCl₃) δ 149.22, 149.05.

Example 7

Synthesis of deoxyribonucleoside 5'-triphosphate (dDssTP)

[Formula 36]

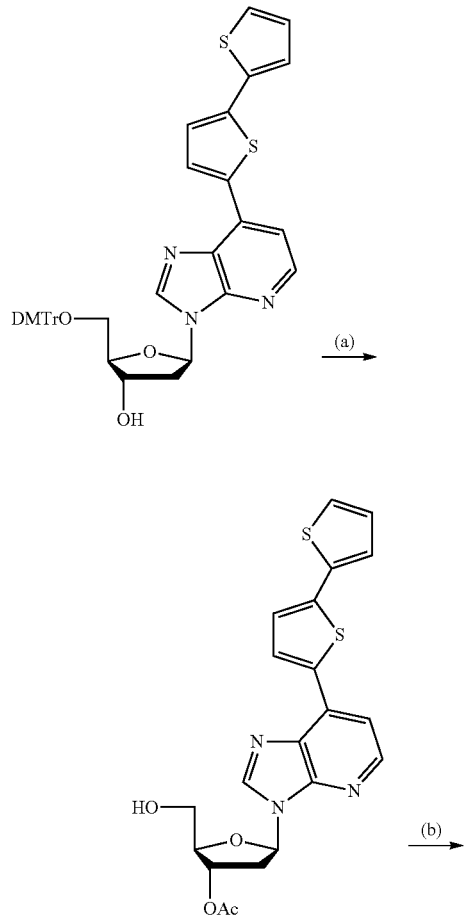

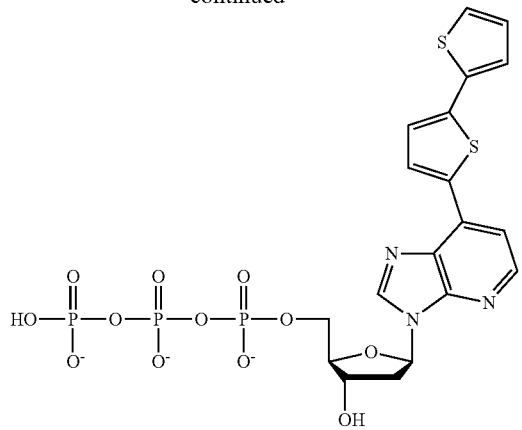

Conditions:
(a) acetic anhydride and pyridine, and then dichloroacetic acid and $CH_2Cl_2$;
(b) chloro-1,3,2-benzodioxaphosphorin-4-one, dioxane, pyridine, tri-n-butylamine, bis(tributylammonium)pyrophosphate, $I_2$, $H_2O$, 28% $NH_4OH$.

(7-1) Synthesis of 7-(2,2'-bithien-5-yl)-3-(2-deoxy-3-O-acetyl-β-D-ribofuranosyl)imidazo[-4,5-b]pyridine 7-(2,2'-Bithien-5-yl)-3-(2-deoxy-5-O-(4,4'-dimethoxytrityl)-β-D-ribofuranosyl)imidazo[4,5-b]pyridine (195 mg, 0.28 mmol) was azeotropically dried with pyridine three times and was dissolved in pyridine (2.8 mL), and acetic anhydride (105 μL, 1.1 mmol) was added thereto, followed by stirring at room temperature for 12 hr. The reaction solution was separated between ethyl acetate and an aqueous 5% sodium hydrogen carbonate solution. The organic layer was washed with saturated brine, dried over anhydrous sodium sulfate, and then concentrated under reduced pressure. The residue was azeotropically dried with toluene and was then dissolved in methylene chloride (28 mL), and dichloroacetic acid (280 μL) was added thereto at 0° C., followed by stirring for 15 min. The reaction solution was separated with 5% sodium hydrogen carbonate. The organic layer was washed with an aqueous 5% sodium hydrogen carbonate solution and saturated brine, dried over anhydrous sodium sulfate, and then concentrated under reduced pressure. 7-(2,2'-Bithien-5-yl)-3-(2-deoxy-3-β-acetyl-β-D-ribofuranosyl)imidazo[4,5-b]pyridine (115 mg, 93%) was obtained through purification by silica gel column chromatography (elution with a solution of 1% methanol in methylene chloride).

¹H NMR (300 MHz, DMSO-d₆) δ 8.79 (s, 1H), 8.37 (d, 1H, J=4.7 Hz), 8.24 (d, 1H, J=3.9 Hz), 7.71 (d, 1H, J=5.2 Hz), 7.60 (dd, 1H, J=1.1, 5.1 Hz), 7.48 (m, 2H), 7.16 (dd, 1H, J=3.7, 5.1 Hz), 6.55 (dd, 1H, J=5.9, 8.7 Hz), 5.41 (d, 1H, J=5.8 Hz), 5.31 (t, 1H, J=5.2 Hz), 4.13 (m, 1H), 3.71-3.63 (m, 10H), 3.71-3.63 (m, 2H), 3.06 (m 1H), 2.53 (m, 1H), 2.11 (s, 3H).

HRMS (FAB, 3-NBA matrix) for $C_{21}H_{20}N_3O_4S_2$ $(M+H)^+$ calculated value: 442.0895, observed value: 442.0869.

(7-2) Synthesis of 7-(2,2'-bithien-5-yl)-3-(2-deoxy-β-D-ribofuranosyl)imidazo[4,5-b]pyridine 5'-triphosphate 7-(2,2'-Bithien-5-yl)-3-(2-deoxy-3-O-acetyl-β-D-ribofuranosyl)imidazo[4,5-b]pyridine (44 mg, 0.1 mmol) was azeotropically dried with pyridine and was then dissolved in pyridine (100 μL) and dioxane (100 μL). A solution of 1 M 2-chloro-1,3,2-benzodioxaphosphorin-4-one in dioxane (110 μL, 0.11 mmol) was added thereto, followed by stirring for 10 min. To this solution, a solution of tributylamine (1004) and a solution of bis(tributylammonium)pyrophosphate in 0.5 M DMF (300 μL, 0.15 mmol) was added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 μL) was added thereto. Water (5.0 mL) was further added thereto, followed by stirring for 30 min. Then, 28% aqueous ammonia (20 mL) was added thereto, followed by stirring at room temperature for 4 hr. The reaction solution was concentrated under reduced pressure, and 7-(2,2'-bithien-5-yl)-3-(2-deoxy-β-D-ribofuranosyl)imidazo[4,5-b]pyridine 5'-triphosphate (33 μmol, 33%) was obtained through purification by DEAE Sephadex (A-25) column chromatography (elution with a solution of 50 mM to 1.0 M TEAB) and C18-HPLC (elution with 0% to 50% acetonitrile in 100 mM TEAA).

$^{1}$H NMR (300 MHz, D$_2$O) δ 8.49 (s, 1H), 8.08 (d, 1H, J=5.4 Hz), 7.58 (d, 1H, J=4.0 Hz), 7.33-7.30 (m, 2H), 7.06 (dd, 1H, J=1.1, 4.7 Hz), 6.99 (dd, 1H, J=3.7, 5.1 Hz), 6.91 (d, 1H, J=3.9 Hz), 6.29 (t, 1H, J=6.9 Hz), 4.68 (m, 1H, overlapping with D$_2$O), 4.18 (m, 1H), 4.10-4.02 (m, 2H), 3.05 (q, 22H, J=7.3 Hz), 2.68 (m, 1H), 2.41 (m, 1H), 1.14 (t, 34H, J=7.3 Hz).

$^{31}$P NMR (121 MHz, D$_2$O) δ -9.71 (d, 1P, J=19.8 Hz), -10.72 (d, 1P, J=19.8 Hz), -22.54 (t, 1P, J=20.0 Hz).

UV-vis spectral data in 10 mM sodium phosphate buffer (pH 7.0): λmax=264 nm (ε9900), 368 nm (ε31400).

ESI-MS (C$_{19}$H$_{20}$N$_3$O$_{12}$S$_2$P$_3$); calculated value: 637.96 (M−H)$^−$, observed value: 637.87 (M−H)$^−$.

Example 8

Synthesis of ribonucleoside 5'-triphosphate (DssTP)

[Formula 37]

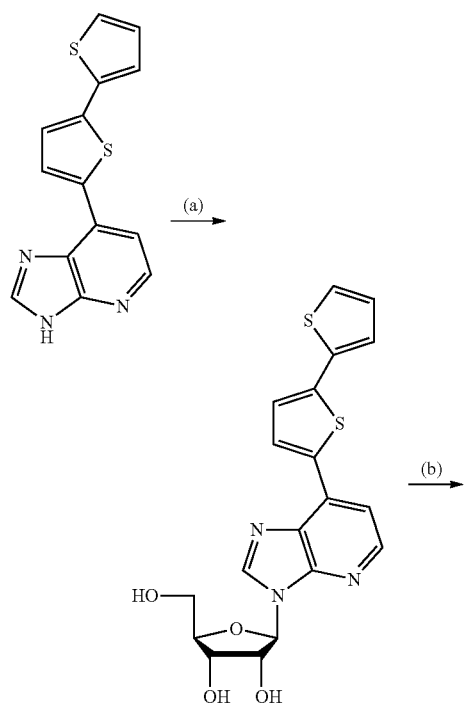

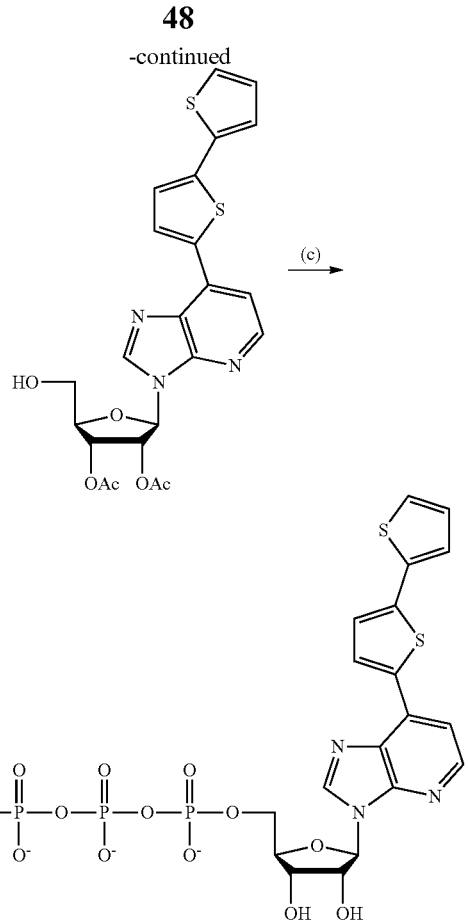

Conditions:
(a) tetra-O-acetyl-β-D-ribofuranose and chloroacetic acid;
(b) (i) DMTrCl and pyridine; (ii) acetic anhydride and pyridine, and then dichloroacetic acid and CH$_2$Cl$_2$;
(c) 2-chloro-4H-1,3,2-benzodioxaphosphorin-4-one, dioxane, pyridine, tri-n-butylamine, bis(tri-n-butylammonium) pyrophosphate, and DMF, and then I$_2$/pyridine/H$_2$O.

(8-1) Synthesis of 7-(2,2'-bithien-5-yl)-3-(β-D-ribofuranosyl)imidazo[4,5-b]pyridine 7-(2,2'-Bithien-5-yl)-3H-imidazo[4,5-b]pyridine (566 mg, 2.0 mmol), tetra-O-acetyl-β-D-ribofuranose (700 mg, 2.2 mmol), and chloroacetic acid (12 mg) were molten at 200° C. for 10 min. After cooling, the mixture was dissolved in methylene chloride and methanol (1:1, v/v, 16 mL), and a solution of 28% sodium methoxide in methanol (2.0 mL) was added thereto, followed by stirring at room temperature for 30 min. The reaction solution was concentrated under reduced pressure, and 7-(2,2'-bithien-5-yl)-3-(β-D-ribofuranosyl)imidazo[4,5-b]pyridine (190 mg, 23%) was obtained through purification by silica gel column chromatography (elution with a solution of 5% methanol in methylene chloride) and C18-HPLC.

$^{1}$H NMR (300 MHz, DMSO-d$_6$) δ 8.80 (s, 1H), 8.36 (d, 1H, J=5.2 Hz), 8.24 (d, 1H, J=3.9 Hz), 7.70 (d, 1H, J=5.2 Hz), 6.60 (dd, 1H, J=1.0, 5.1 Hz), 7.49-7.46 (m, 2H), 7.16 (dd, 1H, J=3.7, 5.1 Hz), 6.09 (d, 1H, J=5.7 Hz), 5.51 (d, 1H, J=6.0 Hz), 5.26 (dd, 1H, J=5.0, 6.4 Hz), 5.21 (d, 1H, J=4.9 Hz), 4.68 (m, 1H), 4.20 (m, 1H), 3.75-3.55 (m, 2H).

$^{13}$C NMR (75 MHz, DMSO-d$_6$) δ 147.25, 144.04, 143.94, 140.10, 136.09, 135.43, 131.58, 130.89, 130.03, 128.57, 126.27, 124.78, 124.57, 113.60, 87.83, 85.57, 73.49, 79.41, 61.41.

HRMS (FAB, 3-NBA matrix) for $C_{19}H_{18}N_3O_4S_2$, $(M+H)^+$ calculated value: 416.0739, observed value: 416.0755. ESI-MS ($C_{19}H_{17}N_3O_4S_2$); calculated value: 416.07 $(M+H)^+$, observed value: 415.86 $(M+H)^+$.

(8-2) Synthesis of 7-(2,2'-bithien-5-yl)-3-(2,3-di-O-acetyl-β-D-ribofuranosyl)imidazo[4,5-b]pyridine 7-(2,2'-Bithien-5-yl)-3-(β-D-ribofuranosyl)imidazo[4,5-b]pyridine (166 mg, 0.4 mmol) was azeotropically dried with pyridine three times and was then dissolved in pyridine (4.0 mL), and 4,4'-dimethoxytrityl chloride (162 mg, 0.48 mmol) was added thereto. After stirring at room temperature for 1 hr, the solution was separated between ethyl acetate and 5% sodium hydrogen carbonate, and the organic layer was washed with water and saturated brine and was concentrated under reduced pressure. The dimethoxytrityl form was purified by silica gel column chromatography (elution with a solution of 1% methanol in methylene chloride) and was azeotropically dried with pyridine three times. Pyridine (4 mL) was added thereto, and acetic anhydride (151 μL, 1.6 mmol) was further added thereto, followed by stirring at room temperature for 12 hr. The reaction solution was separated between ethyl acetate and 5% sodium hydrogen carbonate, and the organic layer was washed with water and saturated brine, dried over anhydrous sodium sulfate, and concentrated under reduced pressure. After azeotropic drying with toluene, the resulting substance was dissolved in methylene chloride (40 mL), and dichloroacetic acid (400 μL) was added thereto at 0° C., followed by stirring for 15 min. The reaction solution was separated with 5% sodium hydrogen carbonate, and the organic layer was washed with an aqueous 5% sodium hydrogen carbonate solution and saturated brine, dried over anhydrous sodium sulfate, and concentrated under reduced pressure. 7-(2,2'-Bithien-5-yl)-3-(2,3-di-O-acetyl-β-D-ribofuranosyl)imidazo[4,5-b]pyridine (178 mg, 89%) was obtained through purification by silica gel column chromatography (elution of 0.5% methanol in methylene chloride).

$^1$H NMR (300 MHz, DMSO-$d_6$) δ 8.83 (s, 1H), 8.38 (d, 1H, J=5.3 Hz), 8.25 (d, 1H, J=4.0 Hz), 7.73 (d, 1H, J=5.3 Hz), 7.61 (dd, 1H, J=1.1, 5.1 Hz), 7.50-7.47 (m, 2H), 7.16 (dd, 1H, J=3.7, 5.1 Hz), 6.39 (d, 1H, J=6.7 Hz), 6.04 (dd, 1H, J=5.7, 6.6 Hz), 5.58-5.53 (m, 2H), 4.28 (m, 1H), 3.81-3.63 (m, 2H) 2.15 (s, 3H), 2.00 (s, 3H).

HRMS (FAB, 3-NBA matrix) for $C_{23}H_{22}N_3O_6S_2$, $(M+H)^+$ calculated value: 500.0950, observed value: 500.0929.

(8-3) Synthesis of 7-(2,2'-bithien-5-yl)-3-(β-D-ribofuranosyl)imidazo[4,5-b]pyridine 5'-triphosphate 7-(2,2'-Bithien-5-yl)-3-(3-O-acetyl-β-D-ribofuranosyl)imidazo[4,5-b]pyridine (50 mg, 0.1 mmol) was azeotropically dried with pyridine and was then dissolved in pyridine (100 μL) and dioxane (100 μL), and a solution of 1 M 2-chloro-1,3,2-benzodioxaphosphorin-4-one in dioxane (110 μL, 0.11 mmol) was added thereto, followed by stirring for 10 min. To this solution, a solution of tributylamine (100 μL) and a solution of bis(tributylammonium)pyrophosphate in 0.5 M DMF (300 μL, 0.15 mmol) was added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 μL) was added thereto. Water (5.0 mL) was further added thereto, followed by stirring for 30 min. Then, 28% aqueous ammonia (20 mL) was added thereto, followed by stirring at room temperature for 4 hr. The reaction solution was concentrated under reduced pressure, and 7-(2,2'-bithien-5-yl)-3-(β-D-ribofuranosyl)imidazo[4,5-b]pyridine 5'-triphosphate (26 μmol, 26%) was obtained through purification by DEAE Sephadex (A-25) column chromatography elution with a solution of 50 mM to 1.0 M TEAB and a solution of 10% acetonitrile in 1 M TEAB) and C18-HPLC (elution with 0% to 50% acetonitrile in 100 mM TEAA).

$^1$H NMR (300 MHz, D$_2$O) δ 8.64 (s, 1H), 8.14 (d, 1H, J=5.4 Hz), 7.75 (d, 1H, J=4.0 Hz), 7.44 (d, 1H, J=5.4 Hz), 7.30 (dd, 1H, J=1.1, 5.1 Hz), 7.15 (dd, 1H, J=1.1, 3.6 Hz), 7.10 (d, 1H, J=3.9 Hz), 6.97 (dd, 1H, J=3.7, 5.1 Hz), 6.12 (d, 1H, J=5.7 Hz), 4.74 (m, 1H, overlapping with D$_2$O), 4.53 (m, 1H), 4.33 (m, 1H), 4.26-4.12 (m, 2H), 3.08 (q, 26H, J=7.4 Hz), 1.16 (t, 38H, J=7.3 Hz).

$^{31}$P NMR (121 MHz, D$_2$O) δ −9.56 (d, 1P, J=19.7 Hz), −10.69 (d, 1P, J=20.0 Hz), −22.44 (t, 1P, J=20.0 Hz).

UV-vis spectral data in 10 mM sodium phosphate buffer (pH 7.0): λmax=264 nm (e 10100), 368 nm (ε31800).

ESI-MS ($C_{19}H_{20}N_3O_{13}S_2P_3$); calculated value: 653.96 $(M-H)^-$, observed value: 653.99 $(M-H)^-$.

Example 9

Synthesis of ribonucleoside 5'-triphosphate (ssTP)

[Formula 38]

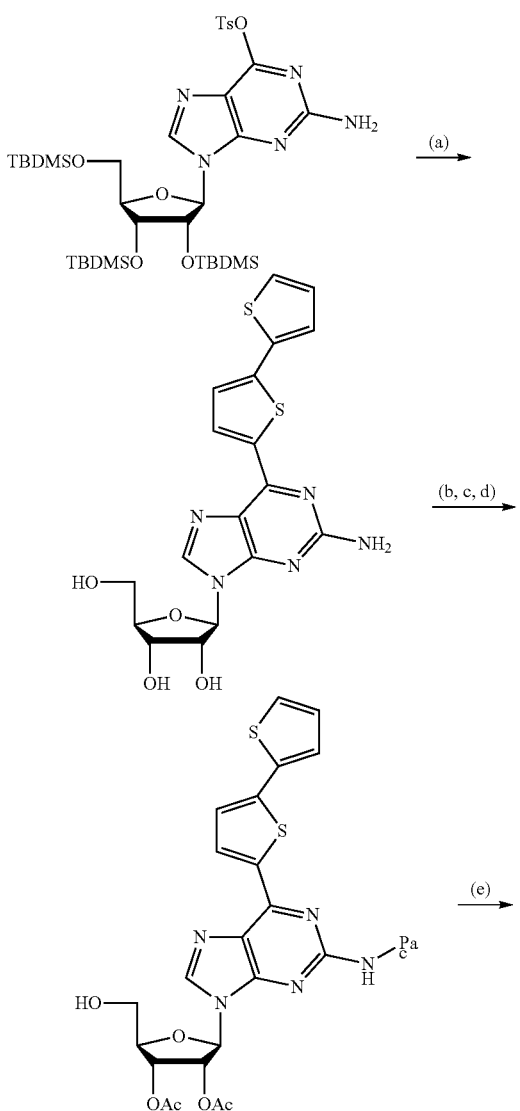

-continued

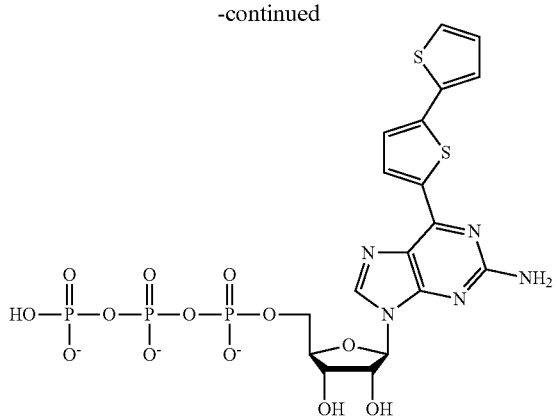

Conditions:
(a) 5-tributylstannyl-2,2'-bithiophene, Pd(PPh$_3$)$_4$, LiCl, and dioxane, and then TBAF and THF;
(b) trimethylsilyl chloride, phenoxyacetyl chloride, hydroxybenzotriazole, pyridine, and CH$_3$CN, and then DMTr-Cl and pyridine;
(c) acetic anhydride and pyridine;
(d) dichloroacetic acid and CH$_2$Cl$_2$;
(e) chloro-1,3,2-benzodioxaphosphorin-4-one, dioxane, pyridine, tri-n-butylamine, bis(tributylammonium)pyrophosphate, I$_2$, H$_2$O, and 28% NH$_4$OH.

(9-1) Synthesis of 2-amino-6-(2,2'-bithien-5-yl)-9-(β-D-ribofuranosyl)purine (ss)

A solution of 6-O-tosyl-2',3',5'-tri-O-tert-butyldimethylsilyl-guanosine (780 mg, 1.0 mmol), tetrakis(triphenylphosphine)palladium (58 mg, 0.05 mmol), lithium chloride (84 mg, 2.0 mmol), and 5-tributylstannyl-2,2'-bithiophene (5.0 mmol) in dioxane was refluxed at 120° C. for 5 hr. The reaction solution was separated between ethyl acetate and water, and the organic layer was washed with water, dried over anhydrous sodium sulfate, and concentrated under reduced pressure. 2',3',5'-Tri-O-tert-butyldimethylsilyl-2-amino-6-(2,2'-bithien-5-yl)-9-(β-D-ribofuranosyl)purine was purified by silica gel column chromatography (elution with methylene chloride). A solution of 1 M tetrabutylammonium fluoride in THF (4.5 mL) was added to a solution of 2',3',5'-tri-O-tert-butyldimethylsilyl-2-amino-6-(2,2'-bithien-5-yl)-9-(β-D-ribofuranosyl)purine in THF (5.5 mL), followed by stirring at room temperature for 30 min. The reaction solution was concentrated, and then 2-amino-6-(2,2'-bithien-5-yl)-9-(β-D-ribofuranosyl)purine (391 mg, 90%, second stage yield) was obtained through purification by silica gel column chromatography and RP-HPLC.

$^1$H NMR (300 MHz, DMSO-d$_6$) δ 8.46 (d, 1H, J=3.9 Hz), 8.41 (s, 1H), 7.61 (dd, 1H, J=1.1, 5.1 Hz), 7.49-7.46 (m, 2H), 7.16 (dd, 1H, J=3.7, 5.1 Hz), 6.58 (bs, 2H), 5.87 (d, 1H, J=5.9 Hz), 5.47 (d, 1H, J=5.9 Hz), 5.47 (d, 1H, J=6.0 Hz), 5.17 (d, 1H, J=4.8 Hz), 5.08 (t, 1H, J=5.6 Hz), 4.53 (m, 1H), 4.15 (m, 1H), 3.93 (m, 1H), 3.70-3.53 (m, 2H).

(9-2) Synthesis of 2-phenoxyacetylamino-6-(2,2'-bithien-5-yl)-9-(2',3'-di-O-acetyl-β-D-ribofuranosyl)purine 2-Amino-6-(2,2'-bithien-5-yl)-9-(β-D-ribofuranosyl)purine (216 mg, 0.5 mmol) was azeotroped with pyridine three times and was dissolved in pyridine (2.5 mL), and trimethylsilyl chloride (635 μL, 5.0 mmol) was added thereto, followed by stirring at room temperature for 30 min (solution A). 1-Hydrorxybenzotriazole (122 mg, 0.9 mmol) was azeotroped with pyridine three times and was then dissolved in pyridine (0.25 mL) and acetonitrile (0.25 mL). The resulting solution was cooled to 0° C., and phenoxyacetyl chloride (104 μL, 0.75 mmol) was added thereto, followed by stirring for 5 min (solution B). Solution A was added to solution B at 0° C., and the mixture was stirred at room temperature for 12 hr. The reaction solution was cooled to 0° C., and 14% aqueous ammonia (0.5 mL) was added thereto, followed by stirring for 10 min. The reaction solution was separated between ethyl acetate and water, and the organic layer was dried over anhydrous sodium sulfate and was then concentrated. 2-Phenoxyacetylamino-6-(2,2'-bithien-5-yl)-9-(β-D-ribofuranosyl)purine (230 mg, 81%) was obtained through purification by silica gel column chromatography (elution with a solution of 5% methanol in methylene chloride). 2-Phenoxyacetylamino-6-(2,2'-bithien-5-yl)-9-(β-D-ribofuranosyl)purine (230 mg, 0.4 mmol) was azeotropically dried with pyridine and was dissolved in pyridine (4.0 mL), and 4,4'-dimethoxytrityl chloride (152 mg, 0.44 mmol) was added thereto. After stirring at room temperature for 1 hr, the solution was separated between ethyl acetate and an aqueous 5% sodium hydrogen carbonate solution. The organic layer was washed with water and saturated brine, dried over anhydrous sodium sulfate, and concentrated under reduced pressure. 2-Phenoxyacetylamino-6-(2,2'-bithien-5-yl)-9-(5-O-dimethoxytrityl-β-D-ribofuranosyl)purine (228 mg, 65%) was obtained through purification by silica gel column chromatography (elution with a solution of 1% methanol in methylene chloride). 2-Phenoxyacetylamino-6-(2,2'-bithien-5-yl)-9-(5-O-dimethoxytrityl-β-D-ribofuranosyl)purine (228 mg, 0.26 mmol) was azeotropically dried with pyridine three times and was then dissolved in pyridine (2.6 mL), and acetic anhydride (99 μL, 1.0 mmol) was added thereto, followed by stirring at room temperature for 12 hr. The reaction solution was separated between ethyl acetate and 5% sodium hydrogen carbonate, and the organic layer was washed with water and saturated brine, dried over anhydrous sodium sulfate, and concentrated under reduced pressure. After azeotropic drying with toluene, the resulting substance was dissolved in methylene chloride (26 mL), and dichloroacetic acid (260 μL) was added thereto at 0° C., followed by stirring for 15 min. The reaction solution was separated with 5% sodium hydrogen carbonate, and the organic layer was washed with an aqueous 5% sodium hydrogen carbonate solution and saturated brine, dried over anhydrous sodium sulfate, and concentrated under reduced pressure. 2-Phenoxyacetylamino-6-(2,2'-bithien-5-yl)-9-(2',3'-di-O-acetyl-β-D-ribofuranosyl)purine (134 mg, 79%, second stage yield) was obtained through purification by silica gel column chromatography (elution of 0.5% methanol in methylene chloride).

$^1$H NMR (300 MHz, DMSO-d$_6$) δ 10.83 (s, 1H), 8.80 (s, 1H), 8.55 (d, 1H, J=1H), 7.66 (d, 1H, J=5.1 Hz), 7.56 (d, 1H, J=4.0 Hz), 7.52 (d, 1H, J=3.5 Hz), 7.32 (m, 2H), 7.18 (m, 1H), 7.02-6.95 (m, 3H), 6.27 (d, 1H, J=6.5 Hz), 5.92 (t, 1H, J=6.2 Hz), 5.57 (dd, 1H, J=2.9, 5.6 Hz), 5.33 (t, 1H, J=5.4 Hz), 5.10 (s, 2H), 4.26 (m, 1H), 3.73 (m, 2H), 2.14 (s, 3H), 1.99 (s, 3H).

(9-3) Synthesis of 2-phenoxyacetylamino-6-(2,2'-bithien-5-yl)-9-(β-D-ribofuranosyl)purine 5'-triphosphate 2-Phenoxyacetylamino-6-(2,2'-bithien-5-yl)-1-(2',3'-di-O-acetyl-β-D-ribofuranosyl)purine (65 mg, 0.1 mmol) was azeotropically dried with pyridine and was then dissolved in pyridine (100 μL) and dioxane (300 μL), and a solution of 2-chloro-1,3,2-benzodioxaphosphorin-4-one in 1 M dioxane (110 μL, 0.11 mmol) was added thereto, followed by stirring for 10 min. To this solution, a solution of tributylamine (100 μL) and a solution of bis(tributylammonium)pyrophosphate in 0.5 M DMF (300 μL, 0.15 mmol) were added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 μL) was added thereto. Water (5.0 mL) was further added thereto, followed by stirring for 30 min. Then, 28% aqueous ammonia (20 mL) was added thereto, followed by stirring at 55° C. for 3 hr. The reaction solution was concentrated under reduced pressure, and 2-phenoxyacetylamino-6-(2,2'-bithien-5-yl-9-(β-D-ribofuranosyl)purine 5'-triphosphate (27.6 μmol, 27%) was obtained through purification by DEAE Sephadex (A-25) column chromatography (elution with a solution of 50 mM to 1.0 M TEAB and a solution of 10% acetonitrile in 1 M TEAB) and C18-HPLC.

$^1$H NMR (300 MHz, D$_2$O) δ 8.42 (s, 1H), 8.10 (d, 1H, J=4.0 Hz), 7.36 (d, 1H, J=5.0 Hz), 7.24 (d, 2H, J=3.9 Hz), 7.01 (dd, 1H, J=3.8, 5.0 Hz), 6.00 (d, 1H, J=5.9 Hz), 4.86 (m, 1H), 4.64 (m, 1H), 4.41 (m, 1H), 4.29 (m, 2H), 3.19 (q, 25H, J=7.4 Hz), 1.28 (t, 37H, J=7.3 Hz).

$^{31}$P NMR (121 MHz, D$_2$O) δ −9.28 (d, 1P, J=19.4 Hz), −10.70 (d, 1P, J=19.7 Hz), −22.41 (t, 1P, J=20.0 Hz).

UV-vis spectral data in 10 mM sodium phosphate buffer (pH 7.0): λmax=388 nm (ε32500).

ESI-MS (C$_{18}$H$_{20}$N$_5$O$_{13}$S$_2$P$_3$); calculated value: 669.97 (M−H)$^-$, observed value: 669.39 (M−H)$^-$.

Example 10

Self-Complementary Ds-Ds Base Pair and Dss-Dss Base Pair

Formation of self-complementary base pairs, a Ds-Ds base pair and a Dss-Dss base pair, was investigated through thermal stability of a double-stranded DNA of 12-mer containing or not containing any of the unnatural bases by measuring the Tm value of the double-stranded DNA.

The 12-mer DNAs having sequences shown in FIG. 3 (SEQ ID NOs: 1 and 2) were chemically synthesized by a phosphoramidite method. The Ds base is a 7-(2-thienyl)imidazo[4,5-b]pyridin-3-yl group, and the Dss base is a 7-(2,2'-bithien-5-yl)imidazo[4,5-b]pyridin-3-yl group.

Changes in absorbance of the double-stranded DNAs were measured with an ultraviolet and visible spectrophotometer UV-2450 (Shimadzu Corporation), and melting temperatures, Tm values, were determined by first-derivative analysis. FIG. 3 shows the results.

The stability of the double-stranded DNA containing a Ds-Ds base pair (Tm=52.0° C.) was only about 1° C. low compared to that of a C-G base pair (Tm=53.1° C.) and was higher than that of a T-A base pair (Tm=48.6° C.).

The Ds-Ds base pair was stable by 8 to 12° C. than the base pairs of Ds and any of the natural bases and thus showed high specificity. Double strands containing the base pair between Ds and any of the natural bases showed substantially the same stability in every base pair between Ds and a natural base. Thus, Ds can be used as a universal base.

The stability of Ds-Pa (Pa: pyrrole-2-carbaldehyde) and Ds-Pn (Pn: 2-nitropyrrole) base pairs, which can function in replication or transcription, was lower than that of the Ds-Ds base pair. Thus, while Ds complements each of Pa and Pn in a template DNA by replication or transcription and, thereby, can be introduced into a specific position of DNA or RNA, a DNA probe complementary to the resulting sequence and containing Ds can dissociate, for example, a Ds-Pn base pair in the double-stranded DNA generated by replication, and hybridizes with the sequence instead of the template DNA.

Similarly, it was confirmed that the Dss-Dss base pair shows high thermal stability and that modifications of Ds show the same effects.

Example 11

Thermal Stability of Double-Stranded DNA Depending on the Natural Base Pair Adjacent to the Self-Complementary Unnatural Ds-Ds Base Pair In order to further investigate the stability of double-stranded DNA containing a Ds-Ds base pair, the thermal stability of DNA fragments was investigated by using various sequence context of the natural base pairs on both sides of a Ds-Ds base pair in a double-stranded DNA. The 12-mer DNAs having sequences shown in FIG. 4 (SEQ ID NOs: 3 to 5) were chemically synthesized by a phosphoramidite method. The Tm value of each double-stranded DNA was determined as in Example 10. FIG. 4 shows the results (including data such as AG separately determined). The results show the order of stability from the highest to the lowest is: 5'-CDsG-3'>5'-CDsA-3'>5'-TDsG-3'>5'-GDsG-3'>5'-TDsA-3'>5'-ADsG-3'>5'-GDsA-3'>5'-GDsC-3'>5'-ADsA-3'>5'-ADsC-3'>5'-ADsT-3'.

Thus, in double-stranded DNAs containing Ds-Ds base pairs, a sequence forming a G-C base pair with three hydrogen bonds on each side of a Ds-Ds base pair is not necessarily stable. Accordingly, a DNA probe exhibiting sequence specificity that is different from the conventional concept can be produced by incorporating a Ds-Ds base pair into DNA (FIG. 5). The results reveal that the thermal stability of double-stranded DNAs is correlated with the order of bases adjacent to the 5' side of a Ds base, C>T>G>A.

Furthermore, in the case of a base pair between Ds and a natural base (Ds-G base pair), the stability of sequences having different natural bases on both sides of the base pair was about 7 to 8° C. lower than that of the Ds-Ds base pair. Accordingly, in the case of base pairs between Ds and any of the natural bases, the stability of the double-stranded DNAs decreases in all different sequences on both sides of the base pair, whereas in the case of a Ds-Ds base pair, the stability of double-stranded DNAs varies depending on the sequences on both sides of the Ds-Ds base pair. The results show that the Ds-Ds base pair is selectively formed in a double-stranded DNA. In addition, the results suggest that the base pairs between Ds and any of the natural bases have a regularity due to adjacent base pairs, similar to that in the Ds-Ds base pair.

Example 12

Figure 6:
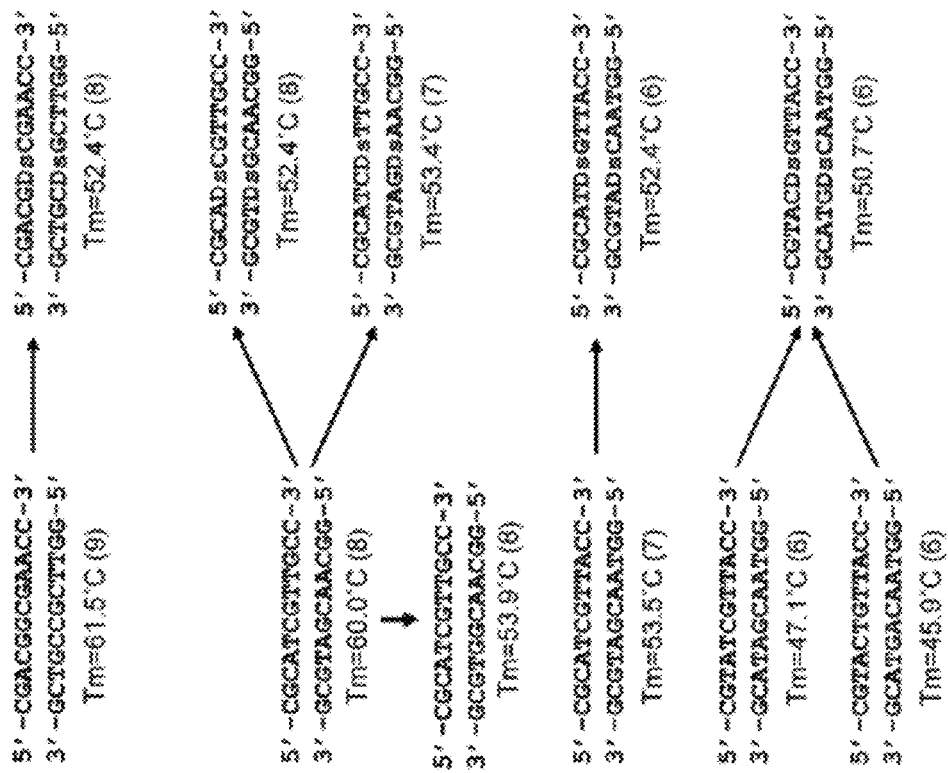
FIG. 6 shows neutralization of thermal stability, which depends on the GC contents in double-stranded DNAs, by a Ds-Ds base pair (each number in parentheses shows the number of G-C base pairs).

Control of Thermal Stability of Double-Stranded DNA by Ds-Ds Base Pair Without Depending on GC Content In a double-stranded DNA composed of only natural bases, the thermal stability of double-stranded DNAs varies depending on a difference in GC content even if the double-stranded DNAs have the same length. That is, the thermal stability of double-stranded DNAs increases with the GC content. For example, as shown in FIG. 6 (fragment on the left), in 12-mer DNA duplexes, the Tm of a duplex having nine G-C base pairs is 61.5° C. whereas the Tm of a duplex having six G-C base pairs decreases to 45 to 47° C. Furthermore, the Tm value of a duplex having eight G-C base pairs decreases from 60.0° C. to 53.9° C. only even if the duplex has one mismatched base pair (T-G base pair in the drawing). Multiplex detection using a plurality of fragments having a different number of G-C base pairs at a constant temperature has a disadvantage that a probe forming a large number of G-C base pairs tend to cause mishybridization.

Accordingly, one site of each 12-mer natural DNA duoplex was substituted by a Ds-Ds base pair, and double-stranded DNAs thereof were produced to investigate the control of thermal stability of double-stranded DNA by introduction of the Ds-Ds base pair.

Figure 7:
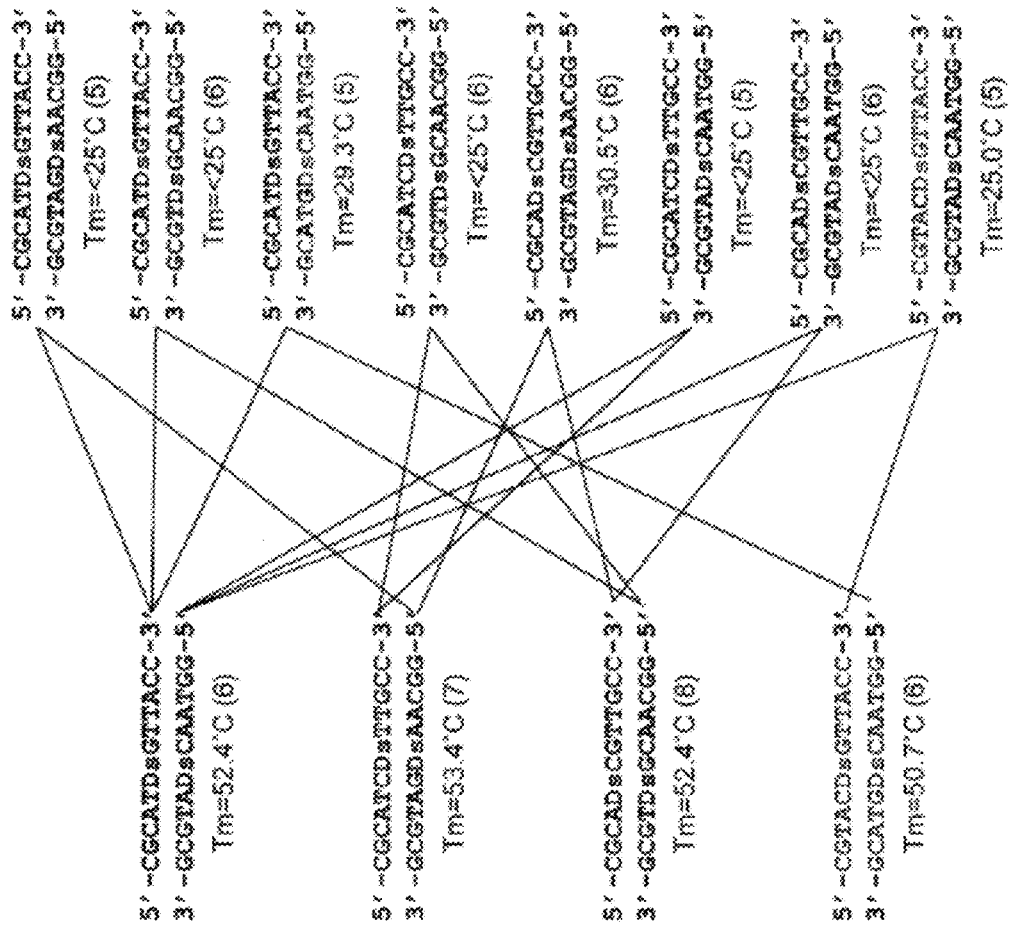
FIG. 7 illustrates four double-stranded DNA tag sequences each containing a Ds-Ds base pair and thermal stability of DNAs by the respective mishybridization processes.

DNA fragments having sequences (SEQ ID NOs: 6 to 27) shown in FIGS. 6 and 7 were chemically synthesized by a phosphoramidite method. The thermal stability of each double-stranded DNA was measured with a Shimadzu UV-2450 UV-Visible spectrophotometer, and the Tm value was determined by primary differentiation using Igor Pro software (WaveMetrics, Inc.). The change in an absorbance of 260 nm by temperature was measured using 5 µM of each double-stranded DNA (length: 12 base pairs) in 100 mM sodium chloride, 10 mM sodium phosphate (pH 7.0), and 0.1 mM EDTA.

As shown in FIG. 6 (fragments on the right), the Tm values of fragments containing six to eight G-C base pairs were controlled to be substantially the same (50.7° C. to 53.4° C.). When each single strand fragment of these double-stranded DNAs was mishybridized with another sequence, the Tm value decreases to 30° C. or less. Accordingly, these fragments can be simultaneously used as probes for multiplex analysis (FIG. 7).

Example 13

Estimation of Melting Temperature (Tm) of Double-Stranded DNA Containing a Ds-Ds Base Pair The stability of double-stranded DNAs containing a Ds-Ds base pair depends on the natural base pair adjacent to the Ds-Ds base pair, and the natural base pairs have a regularity due to their types. Consequently, the Tm value of a double-stranded DNA containing a Ds-Ds base pair can be estimated by a simpler method than a known nearest-neighbor method.

The melting temperature of a double-stranded DNA is generally estimated by a Wallace method, a GC % method, or a nearest-neighbor method. In particular, in the nearest-neighbor method, the melting temperature can be calculated from the sum of nearest-neighbor entropy changes ΔS, the sum of nearest-neighbor enthalpy changes ΔH, the molecular concentration of the DNA fragment, and the Na salt concentration, where the thermodynamic parameters of a nearest-neighbor base pair are known. The free energy ΔG calculated from the Tm measured in this experiment exhibited a high linear positive correlation with the Tm value. The parameters of nearest-neighbor pairs including a Ds-Ds base pair were determined (FIG. 8, the lowest four rows in table) using this, and Tm values were estimated using the theoretical values ΔG calculated from the base sequences. The estimated Tm values were evaluated by comparing with the Tm values experimentally determined based on temperature dependence of UV absorption change (FIG. 9).

Specifically, a melting curve was determined from UV absorption changes of ten different double-stranded DNAs each containing a Ds-Ds base pair and one double-stranded DNA composed of only natural base pairs. The free energy AG at 37° C. of each sequence was calculated by a Hyper-Chromicity method using analysis software Carry WinUV thermal application of Varian, Inc. Subsequently, the parameters of nearest-neighbor base pairs including a Ds-Ds base pair were calculated using the calculation expression and parameter described in Santa Luccia, Proc. Natl. Acad. Sci. USA, Vol. 95, pp. 1460-1465, 1998. FIG. 9 is a graph of the Tm values (estimated values) estimated based on AG calculated from the determined parameter plotted against the Tm values (experimental values) determined from the measured melting curve by primary differentiation. Though some of the fragments deviate from the linear correlation, the calculate results have a high correlation with measured values in most of the cases.

Example 14

Thermal Stability of Double-Stranded DNA Containing a Plurality of Ds-Ds Base Pairs The stability of double-stranded DNAs each containing two Ds-Ds base pairs was investigated. DNAs having sequences (SEQ ID NOs: 20, 21, and 28 to 37) shown in FIG. 10 were chemically synthesized by a phosphoramidite method. The Tm values of the double-stranded DNAs were calculated as in Example 12. FIG. 10 shows the results.

The stability of the double-stranded DNAs (SEQ ID NOs: 28 and 29) each containing adjacent two Ds-Ds base pairs, a 5'-TDsDsG-3' sequence, was 10° C. or more lower than that of the double-stranded DNAs (SEQ ID NOs: 20 and 21) each containing one Ds-Ds base pair. In contrast, the double-stranded DNAs (SEQ ID NOs: 32 and 33) each containing two Ds-Ds base pairs with two natural base pairs therebetween, 5'-CDsGCDsA-3', were about 10° C. stable than the double-stranded DNAs each containing one Ds-Ds base pair. This is comparable to the thermal stability of the double-stranded DNAs (SEQ ID NOs: 34 and 35) composed of only natural base pairs each containing a 5'-CGGCGA-3' sequence, which is a sequence where the Ds-Ds base pair is replaced with a G-C base pair. Thus, a plurality of Ds-Ds base pairs can be introduced into a double-stranded DNA in production of a DNA probe.

Example 15

Identification of Single Base Mismatch by Base Pair (e.g., Ds-G) of Unnatural Base and Natural Base In order to investigate identification of a mismatched base pair adjacent to a base pair of Ds and a natural base in a double-stranded DNA, DNAs having sequences (SEQ ID NOs: 21 and 38 to 45) shown in FIG. 11 were chemically synthesized by a phosphoramidite method. The Tm values of the double-stranded DNAs were calculated as in Example 12. FIG. 11 shows the results.

The unnatural base Ds forms a base pair with any natural base with a certain stability. The inventors have found that the stability of a double-stranded DNA is considerably reduced in the case where the base pair adjacent to a base pair between Ds and a natural base is a mismatched pair (a combination other than A-T and G-C pairs). For example, in the case of a double-stranded DNA containing a G-Ds base pair (FIG. 11), the Tm value of a 12-mer DNA (Tm=45.5° C.) containing a G-Ds base pair about 7° C. decreased compared to that of a G-C base pair (Tm=52.3° C.). The thermal stability of these double-stranded DNAs is further decreased when the adjacent T-A base pair (base pair shown by underlines in FIG. 11) is replaced with a mismatched base pair.

Specifically, the Tm values of double-stranded DNAs in which the T-A base pair adjacent to a G-C base pair was replaced with any of A-A, G-A, and C-A were decreased by 15.0° C., 9.6° C., and 12.6° C., respectively, compared to that in the case of the T-A base pair. On the other hand, in the case of the G-Ds base pair, the Tm values when the adjacent T-A base pair was replaced with any of A-A, G-A, and C-A were decreased by 18.7° C., 16.2° C., and 13.9° C., respectively, compared to that in the case of the T-A base pair.

The results reveal that introduction of the G-Ds base pair into a position adjacent to a mismatched base pair can considerably reduce the stability of the DNA compared to the case where the base pair adjacent to the mismatched base pair is a natural base pair. Accordingly, the SNP can be detected with a DNA having Ds as a probe for hybridization or a primer for PCR in a method of identifying a single-base mutation of a target gene.

Example 16

Thermal Stability of Double-Stranded DNA Containing a Base Pair Between Unnatural Base and Natural Base (Ds-G)

Stability of double-stranded DNAs each containing a Ds-G base pair was investigated. DNAs having sequences (SEQ ID NOs: 10, 11, 14-17, 20, 21, 26, 27, 38, and 42 to 50) shown in FIG. 12 were chemically synthesized by a phosphoramidite method. The Tm values of the double-stranded DNAs were calculated as in Example 12. FIG. 12 shows the results.

In natural base pairs, since a G-C base pair is thermally stable compared to an A-T base pair, the thermal stability of double-stranded DNAs varies depending on a difference in the number of the G-C base pairs even if the DNAs have the same length. As shown on the left column in FIG. 12, 12-mer DNA duplexes containing eight or nine G-C base pairs have Tm values of 60° C. or more, whereas DNAs containing seven G-C base pairs decreased their Tm values to 50° C. The difference in stability between double-stranded DNAs depending on the G-C base pair content leads to a difficulty in designing a primer or probe used in SNP detection or DNA diagnosis. In the present invention, the dependence on the G-C base pair content can be reduced by replacing one G-C base pair in a double-stranded DNA with a Ds-Ds base pair (the center in FIG. 12, and FIG. 6).

Furthermore, the same advantageous effect can be achieved by replacing a G-C base pair with a G-Ds base pair (the right in FIG. 12). Though the replacement by the G-Ds base pair reduces the thermal stability of the double-stranded DNA, it can reduce the denpendence on the G-C content. This result suggests that the introduction of the Ds base is effective in designing of a primer or probe for a target DNA composed of only natural bases. Accordingly, introduction of the G-Ds base pair allows widening of targets: not only DNAs containing unnatural bases but also natural RNAs.

When the complementary base of Ds is G, the base pair is the most stable (see FIG. 12), but Ds may form a base pair with another natural base. That is, base pairs of Ds with natural bases other than G are also useful for reducing the dependence on the G-C content in thermal stability of double-stranded DNAs, as in the use of G-Ds base pair.

INDUSTRIAL APPLICABILITY

The self-complementary base pair of unnatural bases of the present invention can be used as a third base pair in various fields, for example, production of a novel DNA tag for hybridization, use in imaging technology such as a molecular beacon, use in replication or transcription in a combination with a Ds-Pa or Ds-Pn base pair, use in a DNA or RNA computer, and use as a novel codon or anticodon for incorporating a non-natural amino acid into protein. Furthermore, since the unnatural base of the present invention can form a base pair with any natural base with substantially the same thermal stability, a base pair between the unnatural base and a natural base can be used in a DNA probe that can selectively identify a single-base mutation of a target gene.

A base pair containing an unnatural base of the present invention can be a novel base pair, working with the natural A-T and G-C base pairs, and can increase variation of base sequences. Furthermore, the novel base pair can control the thermal stability of different double-stranded DNAs having the same length to be constant regardless of the G-C contents and can therefore reduce mishybridization in methods using a plurality of DNA tags or probes. That is, the accuracy in each practical biotechnology can be enhanced. Furthermore, a probe that can selectively distinguish between match and mismatch with a target DNA at a single-base mutation level can be produced, and thereby the accuracy of a method such as SNP analysis can be enhanced.

SEQUENCE LIST FREE TEXT

SEQ ID NO: 1: DNA fragment for testing thermal stability
SEQ ID NO: 2: DNA fragment for testing thermal stability
SEQ ID NO: 3: DNA fragment for testing thermal stability
SEQ ID NO: 4: DNA fragment for testing thermal stability
SEQ ID NO: 5: DNA fragment for testing thermal stability
SEQ ID NO: 6: DNA fragment for testing thermal stability
SEQ ID NO: 7: DNA fragment for testing thermal stability
SEQ ID NO: 8: DNA fragment for testing thermal stability
SEQ ID NO: 9: DNA fragment for testing thermal stability
SEQ ID NO: 10: DNA fragment for testing thermal stability
SEQ ID NO: 11: DNA fragment for testing thermal stability
SEQ ID NO: 12: DNA fragment for testing thermal stability
SEQ ID NO: 13: DNA fragment for testing thermal stability
SEQ ID NO: 14: DNA fragment for testing thermal stability
SEQ ID NO: 15: DNA fragment for testing thermal stability
SEQ ID NO: 16: DNA fragment for testing thermal stability
SEQ ID NO: 17: DNA fragment for testing thermal stability
SEQ ID NO: 18: DNA fragment for testing thermal stability
SEQ ID NO: 19: DNA fragment for testing thermal stability
SEQ ID NO: 20: DNA fragment for testing thermal stability
SEQ ID NO: 21: DNA fragment for testing thermal stability
SEQ ID NO: 22: DNA fragment for testing thermal stability
SEQ ID NO: 23: DNA fragment for testing thermal stability
SEQ ID NO: 24: DNA fragment for testing thermal stability
SEQ ID NO: 25: DNA fragment for testing thermal stability
SEQ ID NO: 26: DNA fragment for testing thermal stability
SEQ ID NO: 27: DNA fragment for testing thermal stability SEQ ID NO: 28: DNA fragment for testing thermal stability
SEQ ID NO: 29: DNA fragment for testing thermal stability
SEQ ID NO: 30: DNA fragment for testing thermal stability
SEQ ID NO: 31: DNA fragment for testing thermal stability
SEQ ID NO: 32: DNA fragment for testing thermal stability
SEQ ID NO: 33: DNA fragment for testing thermal stability
SEQ ID NO: 34: DNA fragment for testing thermal stability
SEQ ID NO: 35: DNA fragment for testing thermal stability
SEQ ID NO: 36: DNA fragment for testing thermal stability
SEQ ID NO: 37: DNA fragment for testing thermal stability
SEQ ID NO: 38: DNA fragment for testing thermal stability
SEQ ID NO: 39: DNA fragment for testing thermal stability
SEQ ID NO: 40: DNA fragment for testing thermal stability
SEQ ID NO: 41: DNA fragment for testing thermal stability
SEQ ID NO: 42: DNA fragment for testing thermal stability
SEQ ID NO: 43: DNA fragment for testing thermal stability
SEQ ID NO: 44: DNA fragment for testing thermal stability
SEQ ID NO: 45: DNA fragment for testing thermal stability
SEQ ID NO: 46: DNA fragment for testing thermal stability
SEQ ID NO: 47: DNA fragment for testing thermal stability
SEQ ID NO: 48: DNA fragment for testing thermal stability
SEQ ID NO: 49: DNA fragment for testing thermal stability
SEQ ID NO: 50: DNA fragment for testing thermal stability

The invention claimed is:

1. A double-stranded nucleic acid comprising a first nucleic acid strand and a second nucleic acid strand, wherein the first nucleic acid strand contains a nucleotide or nucleotides each having an unnatural base represented by Formula I:

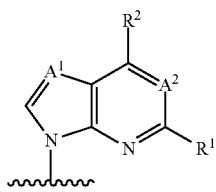

wherein,
$A^1$ represents N or CH;
$A^2$ represents CH;
$R^1$ represents hydrogen or an amino group; and
$R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group
or a derivative thereof as the base, and
the second nucleic acid strand may or may not contain a nucleotide or nucleotides each having an unnatural base represented by Formula I or a derivative thereof as the base; and
the unnatural base represented by Formula I or the derivative thereof in the first nucleic acid strand forms a base pair with any natural base or the unnatural base represented by Formula I or the derivative thereof in the second nucleic acid strand;
wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and
wherein the unnatural base derivative thereof is represented by Formula I further comprising a protecting group selected from a group consisting of: a phenoxyacetyl group, an isobutyryl group, and a dimethyl formamidyl group.

2. The double-stranded nucleic acid according to claim 1, wherein the unnatural base represented by Formula I is an unnatural base in which,
  $A^1$ represents N;
  $A^2$ represents CH;
  $R^1$ represents hydrogen; and
  $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group.

3. The double-stranded nucleic acid according to claim 1, wherein the unnatural base represented by Formula I or the derivative thereof is
  a 7-(2-thienyl)imidazo[4,5-b]pyridin-3-yl group (Ds);
  a 7-(2,2'-bithien-5-yl)imidazo[4,5-b]pyridin-3-yl group (Dss); or
  a derivative thereof,
  wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and
  wherein the unnatural base derivative thereof is represented by Formula I further comprising a protecting group selected from a group consisting of: a phenoxyacetyl group, an isobutyryl group, and a dimethyl formamidyl group.

4. The double-stranded nucleic acid according to claim 1, wherein the derivative of an unnatural base represented by Formula I is a derivative where the substituent shown as $R^2$ in Formula I is further modified by addition of a substituent.

5. The double-stranded nucleic acid according to claim 1, wherein the first nucleic acid strand contains a plurality of nucleotides each having an unnatural base represented by Formula I or a derivative thereof as the bases in such a manner that the nucleotides each having the unnatural base or its derivative as the base are not adjacent to each other in the first nucleic acid strand.

6. The double-stranded nucleic acid according to claim 1, wherein the first nucleic acid strand is a strand where the nucleotide adjacent to the 5' side of the nucleotide having an unnatural base represented by Formula I or a derivative thereof as the base is cytosine (C) or thymine (T) and/or the nucleotide adjacent to the 3' of the nucleotide having the unnatural base or its derivative is guanine (G).

7. A method of hybridizing a nucleic acid containing an unnatural base comprising:
  hybridizing a first nucleic acid strand containing a nucleotide having an unnatural base represented by Formula I:

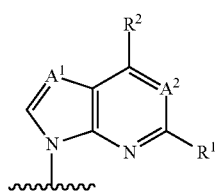

(I)

wherein,
  $A^1$ represents N or CH;
  $A^2$ represents CH;
  $R^1$ represents hydrogen or an amino group; and
  $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof as the base with a second nucleic acid strand which contains or which does not contain a nucleotide having an unnatural base represented by Formula I or a derivative thereof as the base,
  wherein the unnatural base represented by Formula I or the derivative thereof in the first nucleic acid strand forms a base pair with any natural base or the unnatural base represented by Formula I or the derivative thereof in the second nucleic acid strand;
  wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and
  wherein the unnatural base derivative thereof is represented by Formula I further comprising a protecting group selected from a group consisting of: a phenoxyacetyl group, an isobutyryl group, and a dimethyl formamidyl group.

8. The method according to claim 7, wherein the first nucleic acid strand is a probe, tag, or primer for hybridization.

9. The method according to claim 7, wherein the first nucleic acid strand and the second nucleic acid strand are computation devices for a DNA computer.

10. The method according to claim 7, wherein the first nucleic acid strand and the second nucleic acid strand are integrated devices for DNA or RNA origami.

11. The method according to claim 7, wherein hybridization is performed in a multiplex form.

12. A method of identifying a single-base mutation, comprising the steps of:
  (a) preparing a probe complementary to a sequence containing a single-base mutation site to be identified in a target nucleic acid, wherein the probe includes a nucleotide having an unnatural base represented by Formula I:

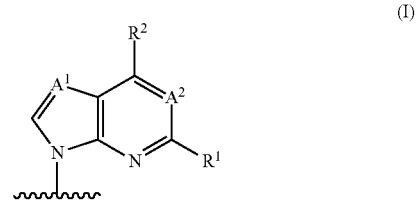

(I)

wherein,
  $A^1$ represents N or CH;
  $A^2$ represents CH;
  $R^1$ represents hydrogen or an amino group; and
  $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof as the base at a position adjacent to the nucleotide complementary to the single-base mutation site to be identified;
  wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and
  wherein the unnatural base derivative thereof is represented by Formula I further comprising a protecting group selected from a group consisting of: a phenoxyacetyl group, an isobutyryl group, and a dimethyl formamidyl group;

(b) hybridizing a target nucleic acid strand with the probe of (a); and (c) identifying that target nucleic acid hybridized with the probe has a base complementary to the probe at the single-base mutation site to be identified.

13. A method of identifying a single-base mutation, comprising the steps of:

(a) preparing a primer complementary to a sequence containing a single-base mutation site to be identified in a target nucleic acid, wherein the primer includes a nucleotide having an unnatural base represented by Formula I:

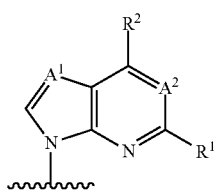

wherein, $A^1$ represents N or CH;

$A^2$ represents CH;

$R^1$ represents hydrogen or an amino group; and $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof as the base at a position adjacent to the nucleotide complementary to the single-base mutation site to be identified;

wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and wherein the unnatural base derivative thereof is represented by Formula I further comprising a protecting group selected from a group consisting of: a phenoxyacetyl group, an isobutyryl group, and a dimethyl formamidyl group;

(b) performing PCR employing a target nucleic acid as the template and using the primer of (a), a nucleotide substrate having an unnatural base represented by Formula I or a derivative thereof as the base, a natural nucleotide substrate, and a DNA polymerase; and (c) identifying that a target nucleic acid amplified by the PCR has a base complementary to the primer at a single-base mutation site to be identified.

14. A method of capturing a nucleic acid using a probe containing an unnatural base, comprising the steps of:

(a) preparing a probe containing a nucleotide having an unnatural base represented by Formula I:

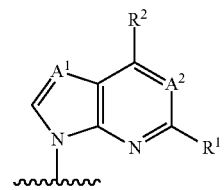

wherein, $A^1$ represents N or CH;

$A^2$ represents CH;

$R^1$ represents hydrogen or an amino group; and $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof as the base, and immobilizing the probe to a solid phase, wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and wherein the unnatural base derivative thereof is represented by Formula I further comprising a protecting group selected from a group consisting of: a phenoxyacetyl group, an isobutyryl group, and a dimethyl formamidyl group;

(b) adding a tag composed of a sequence complementary to the probe of (a) to a nucleic acid to be captured, wherein the tag includes a nucleotide having an unnatural base represented by Formula I or a derivative thereof as the base at a position complementary to the nucleotide having the unnatural base represented by Formula I or the derivative thereof as the base in the probe; and (c) capturing a nucleic acid by hybridizing the probe immobilized to the solid phase in (a) with the nucleic acid provided with the tag in (b).

15. The method according to claim 14, wherein the solid phase is a DNA chip substrate or a bead.

16. A method of synthesizing a peptide by an in vitro translation system, comprising the steps of:

(a) preparing a transfer RNA containing a nucleotide having an unnatural base represented by Formula I:

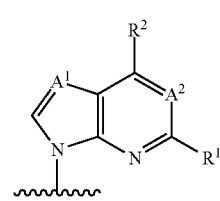

wherein, $A^1$ represents N or CH;

$A^2$ represents CH;

$R^1$ represents hydrogen or an amino group; and $R^2$ represents a substituent selected from the group consisting of a 2-thienyl group, a 2-thiazolyl group, a 2-imidazolyl group, a 2,2'-bithien-5-yl group, a 2-(2-thiazolyl)thien-5-yl group, a 5-(2-thienyl)thiazol-2-yl group, and a 2,2',5',2"-terthien-5-yl group or a derivative thereof as the base at an anticodon position, wherein the unnatural base derivative thereof is represented by Formula I in which the $R^2$ is further modified by addition of $C_1$-$C_3$ alkyl group, a $C_1$-$C_3$ alkenyl group, or a $C_1$-$C_3$ alkynyl group; and wherein the unnatural base derivative thereof is represented by Formula I further comprising a protecting group selected from a group consisting of: a phenoxyacetyl group, an isobutyryl group, and a dimethyl formamidyl group;

(b) preparing a messenger RNA containing a nucleotide having an unnatural base represented by Formula I or a derivative thereof as the base in a coding sequence, where the nucleotide having an unnatural base represented by Formula I or a derivative thereof as the base in the messenger RNA is arranged as a codon corresponding to the anticodon position of the transfer RNA containing the unnatural base so that the nucleotides each having an unnatural base represented by Formula I or a derivative thereof as the base form a base pair in hybridization between codon and anticodon; and (c) synthesizing a peptide by in vitro translation using the transfer RNA of (a), the messenger RNA of (b), and ribosome.

* * * * *